(12) United States Patent
Boshoff et al.

(10) Patent No.: US 9,907,798 B2
(45) Date of Patent: Mar. 6, 2018

(54) METHODS OF TREATING HEAD AND NECK CANCER

(71) Applicants: FOUNDATION MEDICINE, INC., Cambridge, MA (US); UCL Business PLC, London (GB)

(72) Inventors: Chris Hendrik Boshoff, London (GB); Timothy Robert Fenton, Kent (GB); Matthias Alexander Lechner, London (GB); Philip James Stephens, Lexington, MA (US); Matthew J. Hawryluk, Watertown, MA (US); Garrett Michael Frampton, Somerville, MA (US); Roman Yelensky, Newton, MA (US)

(73) Assignees: FOUNDATION MEDICINE, INC., Cambridge, MA (US); UCL Business PLC, London (GB)

( * ) Notice: Subject to any disclaimer, the term of this patent is extended or adjusted under 35 U.S.C. 154(b) by 0 days.

(21) Appl. No.: 15/200,088

(22) Filed: Jul. 1, 2016

(65) Prior Publication Data
US 2016/0375025 A1    Dec. 29, 2016

Related U.S. Application Data

(63) Continuation of application No. 14/177,615, filed on Feb. 11, 2014, now Pat. No. 9,410,954, which is a (Continued)

(51) Int. Cl.
| | | |
|---|---|---|
| *A61K 31/55* | (2006.01) |
| *A61K 31/497* | (2006.01) |
| *A61K 31/52* | (2006.01) |
| *A61K 31/505* | (2006.01) |
| *A61K 31/445* | (2006.01) |
| *A61K 31/40* | (2006.01) |
| *A61K 38/48* | (2006.01) |
| *A61K 39/00* | (2006.01) |
| *C12Q 1/68* | (2006.01) |
| *A61K 31/519* | (2006.01) |
| *C12Q 1/70* | (2006.01) |
| *A61K 31/506* | (2006.01) |
| *A61K 31/454* | (2006.01) |
| *A61K 31/404* | (2006.01) |
| *A61K 31/4196* | (2006.01) |
| *A61K 33/24* | (2006.01) |
| *A61K 31/282* | (2006.01) |
| *A61K 31/337* | (2006.01) |
| *A61K 31/513* | (2006.01) |
| *A61K 39/395* | (2006.01) |
| *A61K 31/436* | (2006.01) |
| *A61K 31/05* | (2006.01) |
| *A61K 31/4709* | (2006.01) |
| *A61K 31/496* | (2006.01) |
| *A61K 31/5377* | (2006.01) |
| *A61K 31/352* | (2006.01) |
| *A61N 5/00* | (2006.01) |
| *A61K 31/366* | (2006.01) |
| *A61K 31/555* | (2006.01) |

(Continued)

(52) U.S. Cl.
CPC ............ *A61K 31/519* (2013.01); *A61K 31/05* (2013.01); *A61K 31/282* (2013.01); *A61K 31/337* (2013.01); *A61K 31/352* (2013.01); *A61K 31/366* (2013.01); *A61K 31/404* (2013.01); *A61K 31/4196* (2013.01); *A61K 31/436* (2013.01); *A61K 31/439* (2013.01); *A61K 31/454* (2013.01); *A61K 31/4709* (2013.01); *A61K 31/4745* (2013.01); *A61K 31/496* (2013.01); *A61K 31/505* (2013.01); *A61K 31/506* (2013.01); *A61K 31/513* (2013.01); *A61K 31/52* (2013.01); *A61K 31/5377* (2013.01); *A61K 31/555* (2013.01); *A61K 33/24* (2013.01); *A61K 39/39558* (2013.01); *A61N 5/00* (2013.01); *A61N 5/10* (2013.01); *C07K 16/2863* (2013.01); *C12Q 1/6883* (2013.01); *C12Q 1/6886* (2013.01); *C12Q 1/708* (2013.01); *G01N 33/571* (2013.01); *A61K 2039/505* (2013.01); *C12Q 2600/106* (2013.01); *C12Q 2600/118* (2013.01); *C12Q 2600/156* (2013.01); *C12Q 2600/158* (2013.01); *C12Q 2600/16* (2013.01)

(58) Field of Classification Search
CPC .. A61K 38/00; A61K 2039/505; A61K 31/55; C07D 239/42; C07D 473/06; C07D 401/12; C07D 401/06; C07D 405/12; C12Q 1/6886
USPC ........... 424/94.63, 133.1; 435/6.14; 514/217, 514/252.12, 263.2, 275, 326, 422
See application file for complete search history.

(56) References Cited

U.S. PATENT DOCUMENTS

| 8,673,972 B2 | 3/2014 | Boshoff et al. |
| 9,410,954 B2 | 8/2016 | Boshoff et al. |

(Continued)

FOREIGN PATENT DOCUMENTS

| EP | 1256578 A1 | 11/2002 |
| WO | 2006/000420 A1 | 1/2006 |

(Continued)

OTHER PUBLICATIONS

Clinical Trial Gov. Identifier NCT00020189.
(Continued)

*Primary Examiner* — Raymond J Henley, III
(74) *Attorney, Agent, or Firm* — Lando & Anastasi, LLP

(57) ABSTRACT

Methods of treating a head and neck cancer are disclosed.

22 Claims, 9 Drawing Sheets

Related U.S. Application Data continuation of application No. 13/958,502, filed on Aug. 2, 2013, now Pat. No. 8,673,972.

(60) Provisional application No. 61/679,354, filed on Aug. 3, 2012.

(51) Int. Cl.
*A61K 31/439* (2006.01)
*A61K 31/4745* (2006.01)
*C07K 16/28* (2006.01)
*G01N 33/571* (2006.01)
*A61N 5/10* (2006.01)

(56) References Cited

U.S. PATENT DOCUMENTS

| 2011/0009353 A1 | 1/2011 | Chen-Kiang et al. |
| 2011/0229876 A1 | 9/2011 | Duerksen-Hughes et al. |
| 2012/0046334 A1 | 2/2012 | Rathos et al. |
| 2013/0150342 A1 | 6/2013 | Brain et al. |
| 2013/0171124 A1 | 7/2013 | Cong et al. |
| 2013/0184285 A1 | 7/2013 | Brain et al. |
| 2014/0037622 A1 | 2/2014 | Boshoff et al. |
| 2015/0030587 A1 | 1/2015 | Boshoff et al. |

FOREIGN PATENT DOCUMENTS

| WO | 2006024945 A1 | 3/2006 |
| WO | 2007/140222 A2 | 12/2007 |
| WO | 2010/020675 A1 | 2/2010 |
| WO | 2011/101409 A1 | 8/2011 |
| WO | 2011/130232 A1 | 10/2011 |
| WO | 2013/006368 A1 | 1/2013 |
| WO | 2013006532 A1 | 1/2013 |

OTHER PUBLICATIONS

Clinical Trial Gov. Identifier NCT01237236.
Clinical Trial Gov. Identifier NCT01394016.
Ding, et al. "Somatic mutations affect key pathways in lung adenocarcinoma", Nature. Oct. 23, 2008; 455(7216): 1069-1075.
Finn, RS et al. "PD 0332991, a selective cyclin D kinase 4/6 inhibitor, preferentially inhibits proliferation of luminal estrogen receptor-positive human breast cancer cell lines in vitro." Breast Cancer Res. 11(5):R77(2009).
International Search Report and Written Opinion dated Mar. 11, 2014 from International Application No. PCT/US2013/053516.
Invitation to Pay Additional Fees and, Where Applicable, Protest Fee from corresponding International Application No. PCT/US2013/053516 dated Dec. 16, 2013.
Kelland et al., "Flavopiridol, the First Cyclin-Dependent Kinase Inhibitor to Enter the Clinic: Current Status" Expert Opinion on Investigational Drugs, Informa Healthcare, UK (2000) vol. 9 No. 12 pp. 2903-2911.
Kies et al., "Induction Chemotherapy and Cetuximab for Locally Advanced Squamous Cell Carcinoma of the Head and Neck: Results From a Ohase II Prospective Trial" Journal of Clinical Oncology (2010) vol. 28 No. 1 pp. 8-14.
Leemans et al., "The Molecular Biology of Head and Neck Cancer", Nature Reviews Cancer, vol. 11, ePub Dec. 16, 2010, Jan. 2011.
Patel et al., "Flavopiridol, a novel cyclin-dependent kinase inhibitor, suppresses the growth of head and neck Squamous cell carcinomas by inducing apoptosis" Journal of Clinical Investigation (1998) vol. 102 No. 9 pp. 1674-1681.
Perrone et al., "Molecular and Cytogenetic Subgroups of Oropharyngeal Squamous Cell Carcinoma", Clin. Cancer Res. 12(22):6643-6651, Nov. 15, 2006.
Perrone, et al., "Molecular and Cytogenetic Subgroups of Oropharyngeal Squamous Cell Carcinoma", Clin Cancer Res., vol. 12, No. 22, pp. 6643-6651, Nov. 15, 2006.
Rothenberg et al., "The Molecular Pathogenesis of Head and Neck Squamous Cell Carcinoma", J. Clin. Invest., 122(6):1951-1957, Jun. 2012.
Shwartz et al., "Phase I Study of the Cyclin-Dependent Kinase Inhibitor Flavopiridol in Combination with Paclitaxel in Patients with Advanced Solid Tumors" Journal of Clinical Oncology (2002) vol. 20 Bo 8 pp. 2157-2170.
Supplementary Partial European Search Report for EP 13 82 5462 dated Feb. 10, 2016.
Zhang, Y. in Proceedings of the AACR-NCI-EORTC International Conference: Molecular Targets and Cancer Therapeutics, 2011:10 (11 Suppl): Abstract nr A236.

Gene Name

| | | | | |
|---|---|---|---|---|
| ABL1 | CDK6 | FLT4 | MEN1 | PTPN11 |
| ABL2 | CDK8 | FOXP4 | MET | PTPRD |
| AKT1 | CDKN2A | GATA1 | MITF | RAF1 |
| AKT2 | CDKN2B | GNA11 | MLH1 | RARA |
| AKT3 | CDKN2C | GNAQ | MLL | RB1 |
| ALK | CEBPA | GNAS | MPL | RET |
| APC | CHEK1 | GPR124 | MRE11A | RICTOR |
| AR | CHEK2 | GUCY1A2 | MSH2 | RPTOR |
| ARAF | CRKL | HOXA3 | MSH6 | RUNX1 |
| ARFRP1 | CRLF2 | HRAS | MTOR | SMAD2 |
| ARID1A | CTNNB1 | HSP90AA1 | MUTYH | SMAD3 |
| ATM | DDR2 | IDH1 | MYC | SMAD4 |
| ATR | DNMT3A | IDH2 | MYCL1 | SMARCA4 |
| AURKA | DOT1L | IGF1R | MYCN | SMARCB1 |
| AURKB | EGFR | IGF2R | NF1 | SMO |
| BAP1 | EPHA3 | IKBKE | NF2 | SOX10 |
| BCL2 | EPHA5 | IKZF1 | NKX2-1 | SOX2 |
| BCL2A1 | EPHA6 | INHBA | NOTCH1 | SRC |
| BCL2L1 | EPHA7 | INSR | NPM1 | STAT3 |
| BCL2L2 | EPHB1 | IRS2 | NRAS | STK11 |
| BCL6 | EPHB4 | JAK1 | NTRK1 | SUFU |
| BRAF | EPHB6 | JAK2 | NTRK2 | TBX22 |
| BRCA1 | ERBB2 | JAK3 | NTRK3 | TET2 |
| BRCA2 | ERBB3 | JUN | PAK3 | TGFBR2 |
| CARD11 | ERBB4 | KDM6A | PAX5 | TNFAIP3 |
| CBL | ERCC2 | KDR | PDGFRA | TNKS |
| CCND1 | ERG | KIT | PDGFRB | TNKS2 |
| CCND2 | ESR1 | KRAS | PHLPP2 | TOP1 |
| CCND3 | EZH2 | LRP1B | PIK3CA | TP53 |
| CCNE1 | FANCA | LRP6 | PIK3CG | TSC1 |
| CD79A | FBXW7 | LTK | PIK3R1 | TSC2 |
| CD79B | FGFR1 | MAP2K1 | PKHD1 | USP9X |
| CDH1 | FGFR2 | MAP2K2 | PLCG1 | VHL |
| CDH2 | FGFR3 | MAP2K4 | PRKDC | WT1 |
| CDH20 | FGFR4 | MCL1 | PTCH1 | |
| CDH5 | FLT1 | MDM2 | PTCH2 | |
| CDK4 | FLT3 | MDM4 | PTEN | |

Fig. 2A

Gene Name

| |
|---|
| ALK |
| BCR |
| BRAF |
| EGFR |
| ETV1 |
| ETV4 |
| ETV5 |
| ETV6 |
| EWSR1 |
| MLL |
| RAF1 |
| RARA |
| RET |
| TMPRSS2 |

Fig. 2B

METHODS OF TREATING HEAD AND NECK CANCER

RELATED APPLICATIONS

This application is a continuation of U.S. patent application Ser. No. 14/177,615, filed Feb. 11, 2014, now U.S. Pat. No. 9,410,954, which is a continuation of U.S. patent application Ser. No. 13/958,502, filed Aug. 2, 2013, now U.S. Pat. No. 8,673,972, issued Mar. 18, 2014, which claims the benefit of U.S. Provisional Application No. 61/679,354, filed Aug. 3, 2012, the contents of which are hereby incorporated by reference in their entirety.

BACKGROUND

Cancer represents the phenotypic end-point of multiple genetic lesions that endow cells with a full range of biological properties required for tumorigenesis. Indeed, a hallmark genomic feature of many cancers, including, for example, cancers of the head and neck, breast cancer, prostate cancer, ovarian cancer, endometrial cancer, and colon cancer, is the presence of numerous complex chromosome structural aberrations, including translocations, intra-chromosomal inversions, point mutations, deletions, gene copy number changes, gene expression level changes, and germline mutations, among others. Whether a cancer will respond to a particular treatment option may depend on the particular genomic features present in the cancer.

The need still exists for identifying effective treatment options for cancer. Identification of genetic features in a cancer can be an effective approach to develop compositions, methods and assays for evaluating and treating the cancer.

SUMMARY

The invention is based, at least in part, on the discovery that subjects with a cancer, such as a head and neck cancer (e.g., a head and neck squamous cell carcinoma (HNSCC)), have certain genetic alterations depending on whether or not they carry the human papillomavirus (HPV). In one embodiment, Applicants have discovered that subjects with a head and neck cancer, who are also HPV-negative (HPV−), are more likely to carry a genomic alteration (e.g., a copy number alteration or a mutation) in a cell cycle gene, such as in one or more of CDKN2A (cyclin dependent kinase inhibitor 2A), CDKN2B (cyclin dependent kinase inhibitor 2B), CCNE1 (Cyclin E1), CCND1 (Cyclin D1), CCND2 (Cyclin D2), CCND3 (Cyclin D3), CDK4 (cyclin dependent kinase 4) or CDK6 (cyclin dependent kinase 6). Thus, a subject with an HPV− status can be treated with a drug that targets the cell cycle gene, or a gene or protein that functions downstream of the cell cycle gene. For example, a HNSCC subject with an HPV− status can be treated with a CDK (cyclin dependent kinase) inhibitor, which will target CDK proteins overexpressed due to a CDKN2A or CDKN2B loss-of-function mutation, such as a CDKN2A or CDKN2B deletion. Further, genomic profiling (e.g., acquiring the sequence of all or part of a cyclin-dependent kinase inhibitor, a cyclin, or a cyclin-dependent kinase, e.g., CDKN2A, CDKN2B, CCNE1, CCND1, CCND2, CCND3, CDK4 or CDK6), is not necessary before making the determination that the HPV−/HNSCC subject is likely to respond to treatment with a CDK inhibitor, or before administering the CDK inhibitor. In other embodiments, Applicants have discovered that subjects with a head and neck cancer, who are HPV-positive (HPV+), tend to have a higher frequency of PI3 Kinase (PI3K) alterations (e.g., copy number alterations or mutations), and a lower frequency of alterations in cell cycle genes. Thus, subjects who are HPV+ are less likely to respond to a treatment with a drug that targets a cell cycle gene, or a gene or protein that functions downstream of the cell cycle gene. For example, a HNSCC subject with an HPV+ status can be treated with a drug other than a CDK (cyclin dependent kinase) inhibitor, or a CCND1 inhibitor. The HPV+ HNSCC patient can alternatively, be treated with a PI3K inhibitor and/or an mTOR inhibitor. In one embodiment, HPV+ HNSCC patient is subjected to genomic profiling to confirm abnormal upregulation of PI3K prior to treatment with the PI3K inhibitor. Thus, evaluation of HPV− status in a subject with a cancer, e.g., a head and neck cancer, can be used to evaluate cancer responsiveness. In other embodiments, identification of an alteration (e.g., a mutation) in a cell cycle gene is indicative that the cancer is more responsive to a CDK inhibitor. Therefore, the invention provides methods, assays and kits for evaluating, identifying, assessing, evaluating, and/or treating a subject having a cancer, e.g., a head and neck cancer.

Accordingly, in one aspect, the invention features a method of treating a subject having a cancer, e.g., a head and neck cancer (e.g., an HNSCC). The method includes:

acquiring knowledge of an HPV− status (e.g., the presence or absence of HPV) in a subject, and responsive to the determination that the subject is HPV⁻, administering to the subject an inhibitor that targets a cell-cycle gene, such as a CDK inhibitor. In one embodiment, the subject is further administered radiation therapy, or is further administered a surgery to treat the cancer.

In certain embodiments, the method further includes evaluating the subject for the presence or absence of an alteration (e.g., a mutation or a copy number alteration) in a cell cycle gene, e.g., a CDKN2A gene, a CDKN2B gene, CCNE1 gene, CCND1 gene, CCND2 gene, CCND3 gene, CDK4 gene or CDK6 gene.

In one embodiment, the subject, e.g., an HPV− patient, is administered a CDK inhibitor that inhibits one or both of CDK4 or CDK6 (e.g., an inhibitor that inhibits both CDK4 and CDK6, i.e., a CDK4/6 inhibitor). In one embodiment, the CDK4/6 inhibitor is LEE011 (Novartis), LY-2835219, or PD 0332991 (Pfizer). In one embodiment, the CDK inhibitor inhibits CDK1, CDK2, CDK7, and/or CDK9. In certain embodiments, the CDK inhibitor is flavopiridol, indisulam, AZD5438, SNS-032, SCH 727965 (Dinaciclib), JNJ-7706621, indirubin, or seliciclib. In one embodiment, the CDK inhibitor is not flavopiridol.

In one embodiment, the subject is HPV−, and has a mutation in a cell cycle gene, such as the CDKN2A gene or CDKN2B gene, or the CCND1 gene. In another embodiment, the mutation in the CDKN2A gene is a loss-of-function mutation. For example, the mutant CDKN2A gene has a deletion, such as a homozygous deletion, or one or more point mutations. In another embodiment, the mutation in the CCND1 gene is a gain-of-function mutation. For example, the CCND1 gene can be amplified. In one embodiment, the cell cycle gene has a mutation as described in Table 4.

In certain embodiments, the subject has a localized cancer, e.g., a localized cancer of the head or neck. In other embodiments, the subject has metastatic cancer. In certain embodiments, the subject is further evaluated for the presence of one or more of the alterations, e.g., mutations, disclosed herein. In one embodiment, the treatment of the subject is modified, e.g., decreased, discontinued, or otherwise altered, in response to the detection of one or more of the alterations, e.g., mutations, described herein.

In one embodiment, the step of acquiring knowledge of the HPV status in the method includes detecting or identifying an HPV molecule in the subject, e.g., in a sample from the subject. In one embodiment, the HPV molecule is an HPV nucleic acid or HPV protein in the subject, e.g., the sample. In some embodiments, an HPV nucleic acid is identified by in situ hybridization (ISH), PCR, Northern blot analysis, or sequencing of nucleic acids in the sample. HPV protein can be identified, e.g., immunohistochemistry (IHC), by Western blot analysis. In one embodiment, HPV is detected by IHC to detect p16 protein (encoded by CDKN2A), which is strongly and diffusely expressed in about 93% of HPV-associated squamous cell carcinomas (SCCs). A sample from a subject can be, for example, a blood or serum sample, or a urine sample, or a tissue sample, such as a tumor tissue sample (such as from a biopsy), or a buccal swab. The sample can be fresh or frozen.

In one embodiment, determination that the subject is HPV− is sufficient to conclude that the subject is a candidate to receive treatment with a CDK inhibitor, e.g., a CDK4/6 inhibitor. Further genomic profiling is not necessary before making the determination that the subject is likely to respond to treatment with a CDK inhibitor, or before administering the CDK inhibitor.

In one embodiment, the alteration of the cell cycle gene is detected in a nucleic acid molecule or polypeptide in a biological sample from the subject. For example, the sample can include a fluid, such as blood, plasma, saliva, or urine; cells, such as from a buccal swab; or a tissue, such as a tumor tissue, such as from a biopsy. The biological sample can be acquired from a subject, or from a depository, for example.

In one embodiment, the sample includes tissue or a nucleic acid, such as from a tumor biopsy or a circulating tumor cell.

In one embodiment, a mutant cell cycle polypeptide is detected. For example, in certain embodiments, the mutant cell cycle polypeptide is a mutant CDKN2A polypeptide, a mutant CDKN2B polypeptide, a mutant CCNE1 polypeptide, a mutant CCND1 polypeptide, a mutant CCND2 polypeptide, a mutant CCND3 polypeptide, a mutant CDK4 polypeptide or a mutant CDK6 polypeptide. In one embodiment, a biological sample is positive for CCND1 immunohistochemistry, and the positive staining is greater than in a non-tumor control sample. In one embodiment, a change in levels of a protein upstream or downstream of a mutant cell cycle gene is detected. For example, detection of increased levels of CDK protein (e.g., a CDK4 or CDK6 protein) is indicative of a loss-of-function mutation in a CDKN2A or CDKN2B gene.

In one embodiment, a mutant cell-cycle gene is detected in a nucleic acid molecule, such as a nucleic acid molecule isolated from a tumor tissue or a circulating tumor cell. The mutation in the cell-cycle gene can be detected by a method known in the art, such as a nucleic acid hybridization assay, an amplification-based assay, a PCR-RFLP assay, real-time PCR, sequencing, screening analysis, FISH (fluorescence in situ hybridization), spectral karyotyping or MFISH (multicolor FISH), comparative genomic hybridization, in situ hybridization, SSP (sequence specific primers), HPLC (high performance liquid chromatography) or mass-spectrometric genotyping.

In another embodiment, the level or activity of the mutant cell-cycle gene is evaluated.

A mutation in the cell cycle gene can be detected, for example, prior to initiating, during, or after, treatment of a subject. In one embodiment, the mutation in the cell cycle gene is detected at the time of diagnosis with a cancer.

In one embodiment, the subject is HPV$^+$, and the subject is administered an agent (e.g., an anti-cancer agent) other than a CDK (cyclin-dependent kinase) inhibitor, e.g., other than a CDK4/6 inhibitor. For example, the HPV+ patient is administered 4-hydroxyperoxycyclophosphoramide, 5-fluorouracil (5-FU), 5-fluorodeoxyuridine (5-FUdR), 5-azacytidine, 6-mercaptopurine, 6-thioguanine, actinomycin D, amsacrine, bis-chloroethylnitrosurea, bleomycin, bryostatin-1, busulfan, carboplatin (Paraplatin®), chlorambucil, cisplatin (Platinol®), cetuximab (Erbitux®), colchicine, cyclophosphamide, cytarabine, cytosine arabinoside, dacarbazine, daunorubicin, daunomycin, dactinomycin, deoxycoformycin, diethylstilbestrol (DES), doxorubicin, etoposide (VP-16), epirubicin, esorubicin, fluorouracil (5-FU, Adrucil), gemcitabine, hexamethylmelamine, hydroxyprogesterone, hydroxyurea, idarubicin, ifosfamide, irinotecan, mafosfamide, melphalan, methotrexate (MTX), methylcyclohexylnitrosurea, mithramycin, mitomycin C, mitoxantrone, nitrogen mustards, paclitaxel (Taxol®), pentamethylmelamine, prednisone, procarbazine, tamoxifen, taxol, teniposide, testosterone, trimetrexate, topotecan, vincristine, and vinblastine.

In one embodiment, the subject is HPV+, and the subject has an alteration (e.g., a mutation) in a gene in the PI3K (Phosphatidylinositol-3 kinase) pathway, such as mutation in a PIK3CA (phosphoinositide-3-kinase, catalytic, alpha polypeptide) gene, a PTEN (phosphatase and tensin homolog) gene, or an STK11 (serine/threonine kinase 11) gene. In one embodiment, said HPV+ patient can be treated with an inhibitor of a protein in the PI3K pathway, such as a PIK3CA protein, a PTEN protein, or an STK11 protein, or a protein whose expression is altered (e.g., upregulated) as a result of a mutation in a gene of the PI3K pathway. For example, the patient can be treated with an mTOR (mammalian Target of Rapamycin) inhibitor, such as rapamycin (sirolimus) or a rapamycin derivative (40-O-(2-hydroxyethyl) rapamycin, 40-[3-hydroxy-2-(hydroxymethyl)-2-methylpropanoate]-rapamycin or 40-epi-(tetrazolyl)-rapamycin); a PI3K inhibitor, such as BKM120 (Novartis, Basel, Switzerland), LY294002, or wortmannin; or a PI3K-mTOR inhibitor, such as BEZ235 (Novartis, Basel, Switzerland), BGT226 (Novartis, Basel, Switzerland) or XL765 (Exelixis, San Francisco, Calif.). In one embodiment, the subject is tested by genomic profiling to confirm upregulation of a PIK3CA gene or PTEN gene or STK11 gene prior to treatment with an mTOR inhibitor or PI3K inhibitor.

In one embodiment, the HPV− subject is determined to have an alteration in a gene in the PI3K pathway, such as mutation in a PIK3CA gene, a PTEN (phosphatase and tensin homolog) gene, or an STK11 (serine/threonine kinase 11) gene, and the subject is treated with an mTOR inhibitor, a PI3K inhibitor, or a PI3K-mTOR inhibitor. The mutation in the gene in the PI3K pathway can be determined, for example, by genomic profiling.

In one aspect, the invention features a method of treating a subject having a cancer, e.g., a head and neck cancer (e.g., an HNSCC). The method includes:

acquiring knowledge of a presence of HPV in the subject, and responsive to a determination of the presence or absence of HPV in the subject, selecting one or more of:

(1) identifying or selecting the subject as likely or unlikely to respond to a treatment;

(2) selecting a treatment option, such as treatment with a CDK inhibitor, such as a CDK4/6 inhibitor; and/or (3) treating the subject, e.g., with the CDK inhibitor.

In one embodiment, the subject is determined to be HPV−, and responsive to the determination that the patient is HPV−, the patient is identified as likely to respond to treatment with a CDK inhibitor. In another embodiment, the subject is determined to be HPV−, and responsive to the determination that the patient is HPV−, a cell-cycle inhibitor is selected as a treatment option. The cell-cycle inhibitor can be, for example, a cyclin-dependent kinase (CDK) inhibitor, such as a CDK4 or CDK6 inhibitor, e.g., a CDK4/6 inhibitor, such as LEE011 (Novartis), LY-2835219 or PD 0332991 (Pfizer). In one embodiment, the CDK inhibitor inhibits CDK1, CDK2, CDK7, and/or CDK9. In certain embodiments, the CDK inhibitor is flavopiridol, indisulam, AZD5438, SNS-032, SCH 727965 (Dinaciclib), JNJ-7706621, indirubin, or seliciclib. A CDK4/6 inhibitor can inhibit both CDK4 and CDK6 activity. In one embodiment, the CDK inhibitor is not flavopiridol.

In another embodiment, the subject is further administered the selected treatment option.

In one embodiment, the subject is determined to be HPV+, and responsive to the determination that the patient is HPV+, the patient is identified as unlikely to respond to treatment with a cell-cycle inhibitor. In one embodiment, the subject is determined to be HPV+, and responsive to the determination that the patient is HPV+, an anti-cancer agent other than a CDK inhibitor is selected as a treatment option. For example, the anti-cancer agent is one or more of 4-hydroxyperoxycyclophosphoramide, 5-fluorouracil (5-FU), 5-fluorodeoxyuridine (5-FUdR), 5-azacytidine, 6-mercaptopurine, 6-thioguanine, actinomycin D, amsacrine, bis-chloroethylnitrosurea, bleomycin, bryostatin-1, busulfan, carboplatin (Paraplatin®), chlorambucil, cisplatin (Platinol®), cetuximab (Erbitux®), colchicine, cyclophosphamide, cytarabine, cytosine arabinoside, dacarbazine, daunorubicin, daunomycin, dactinomycin, deoxycoformycin, diethylstilbestrol (DES), doxorubicin, etoposide (VP-16), epirubicin, esorubicin, fluorouracil (5-FU, Adrucil), gemcitabine, hexamethylmelamine, hydroxyprogesterone, hydroxyurea, idarubicin, ifosfamide, irinotecan, mafosfamide, melphalan, methotrexate (MTX), methylcyclohexylnitrosurea, mithramycin, mitomycin C, mitoxantrone, nitrogen mustards, paclitaxel (Taxol®), pentamethylmelamine, prednisone, procarbazine, tamoxifen, taxol, teniposide, testosterone, trimetrexate, topotecan, vincristine, and vinblastine.

In one embodiment, the subject, e.g., an HPV+ patient, is administered radiation therapy, or is administered a surgery to treat the cancer. In some embodiments, the patient is administered one or more of a radiation therapy, a surgery to treat a cancer or an anti-cancer agent that is not a CDK inhibitor.

In one embodiment, the HPV− patient is further administered radiation therapy, or is further administered a surgery to treat the cancer.

In certain embodiments, the subject has a localized cancer, e.g., a localized cancer of the head or neck. In other embodiments, the subject has metastatic cancer. In certain embodiments, the subject is further evaluated for the presence of one or more of the alterations, e.g., mutations, disclosed herein. In one embodiment, the treatment of the subject is modified, e.g., decreased, discontinued, or otherwise altered, in response to the detection of one or more of the alterations, e.g., mutations, described herein.

In one embodiment, the HPV− patient is further determined to have an alteration, e.g., a mutation, in a cell cycle gene, such as a CDKN2A, CDKN2B or CCND1 gene. In one embodiment, the HPV− patient has a loss-of-function mutation in one or both of the CDKN2A gene or the CDKN2B gene, and in another embodiment, the HPV− patient has a gain-of-function mutation in the CCND1 gene.

In one embodiment, the subject, e.g., the HPV+ patient, is further determined to have a mutation in the PI3K pathway. For example, the HPV+ patient can be determined to have a mutation in a PIK3CA gene, a PTEN gene, or an STK11 gene. The determination can be made, for example, by genomic profiling. In one embodiment, an HPV+ patient determined to have a mutation in a PIK3CA gene, a PTEN gene, or an STK11 gene can be treated with an inhibitor of a PIK3CA gene, a PTEN gene, or an STK11 gene. For example, the patient can be treated with an mTOR inhibitor, a PI3K inhibitor, or a dual PI3K-mTOR inhibitor In one embodiment, an HPV− patient, is determined to have a mutation in the PI3K pathway, e.g., a mutation in a PIK3CA gene, a PTEN gene, or an STK11 gene, and the HPV− patient is treated with an inhibitor of a PIK3CA gene, a PTEN gene, or an STK11 gene. The determination is made, for example, by genomic profiling.

In one aspect, the invention features a method of treating a subject having a cancer, such as a head and neck cancer, e.g., an HNSCC. The method includes, for example, selecting a subject having a squamous cell carcinoma of the head and neck on the basis of whether the subject is HPV− or HPV+, and if the subject is HPV−, then the subject is administered a CDK inhibitor, and if the subject is HPV+, then the subject is administered an anti-cancer agent other than a CDK inhibitor.

In one embodiment, the subject is HPV− and the CDK inhibitor is a CDK4 or CDK6 inhibitor, e.g., a CDK4/6 inhibitor, such as LEE011 (Novartis), LY2835219, or PD 0332991 (Pfizer). In another embodiment, the CDK inhibitor inhibits CDK1, CDK2, CDK7, and/or CDK9. In certain embodiments, the CDK inhibitor is flavopiridol, indisulam, AZD5438, SNS-032, SCH 727965 (Dinaciclib), JNJ-7706621, indirubin or seliciclib. In one embodiment, the CDK inhibitor is not flavopiridol.

In another embodiment, the subject is HPV+, and one or more of the following anti-cancer agents is administered to the subject: 4-hydroxyperoxycyclophosphoramide, 5-fluorouracil (5-FU), 5-fluorodeoxyuridine (5-FUdR), 5-azacytidine, 6-mercaptopurine, 6-thioguanine, actinomycin D, amsacrine, bis-chloroethylnitrosurea, bleomycin, bryostatin-1, busulfan, carboplatin (Paraplatin®), chlorambucil, cisplatin (Platinol®), cetuximab (Erbitux®), colchicine, cyclophosphamide, cytarabine, cytosine arabinoside, dacarbazine, daunorubicin, daunomycin, dactinomycin, deoxycoformycin, diethylstilbestrol (DES), doxorubicin, etoposide (VP-16), epirubicin, esorubicin, fluorouracil (5-FU, Adrucil), gemcitabine, hexamethylmelamine, hydroxyprogesterone, hydroxyurea, idarubicin, ifosfamide, irinotecan, mafosfamide, melphalan, methotrexate (MTX), methylcyclohexylnitrosurea, mithramycin, mitomycin C, mitoxantrone, nitrogen mustards, paclitaxel (Taxol®), pentamethylmelamine, prednisone, procarbazine, tamoxifen, taxol, teniposide, testosterone, trimetrexate, topotecan, vincristine, or vinblastine.

In one embodiment, the HPV+ patient is administered radiation therapy, or is administered a surgery to treat the cancer. In some embodiments, the patient is administered one or more of a radiation therapy, a surgery to treat a cancer or an anti-cancer agent that is not a CDK inhibitor.

In one embodiment, the HPV− patient is further administered radiation therapy, or is further administered a surgery to treat the cancer.

In certain embodiments, the subject has a localized cancer, e.g., a localized cancer of the head or neck. In other embodiments, the subject has metastatic cancer. In certain embodiments, the subject is further evaluated for the presence of one or more of the alterations, e.g., mutations, disclosed herein. In one embodiment, the treatment of the subject is modified, e.g., decreased, discontinued, or otherwise altered, in response to the detection of one or more of the alterations, e.g., mutations, described herein.

In one embodiment, the HPV− patient is further determined to have a genomic alteration in a cell cycle gene, such as a CDKN2A gene, CDKN2B gene, CCNE1 gene, CCND1 gene, CCND2 gene, CCND3 gene, CDK4 gene or CDK6 gene. The genomic alteration can be, for example, a base substitution, a small insertion, a gene amplification, or a gene deletion, such as a deletion of an entire gene, or both alleles of a gene, as in a homozygous deletion. In one embodiment, the alteration in the CDKN2A or CDKN2B gene is a loss-of-function mutation, and in another embodiment, the alteration in the CCND1 gene is a gain-of-function mutation. In certain embodiments, the alteration is an alteration listed in Table 4.

In one embodiment, the subject, e.g., HPV+ patient, is further determined to have a genomic alteration (e.g., a mutation) in the PI3K pathway. For example, the HPV+ patient can be determined to have a mutation in a PIK3CA gene, a PTEN gene, or an STK11 gene. In one embodiment, said HPV+ patient can be treated with an inhibitor of a PIK3CA gene, a PTEN gene, or an STK11 gene. For example, the patient can be treated with an mTOR inhibitor, a PI3K inhibitor, or a PI3K-mTOR inhibitor.

In one embodiment, an HPV− subject is determined to have an alteration in a gene in the PI3K pathway, such as a mutation in a PIK3CA gene, a PTEN (phosphatase and tensin homolog) gene, or an STK11 (serine/threonine kinase 11) gene, and the subject is further administered an mTOR inhibitor, a PI3K inhibitor, or a PI3K-mTOR inhibitor.

In one aspect, the invention features a method of treating subject having a cancer, such as head and neck cancer, e.g., an HNSCC. The method includes, for example, selecting a subject having a cancer on the basis of whether the subject is HPV+ or HPV−; acquiring knowledge of whether a subject has a mutation in a cell-cycle gene; and if the subject has a mutation in a cell cycle gene, administering a CDK inhibitor to the subject. If the subject does not have a mutation in a cell-cycle gene, then an anti-cancer drug other than a CDK inhibitor is administered to the subject.

In one embodiment, the CDK inhibitor inhibits one or both of a CDK4 or CDK6 inhibitor, e.g., an inhibitor that inhibits CDK4 and CDK6, e.g., a CDK4/6 inhibitor. Exemplary CDK4/6 inhibitors include, e.g., LEE011 (Novartis), LY-2835219, and PD 0332991 (Pfizer). In one embodiment, the CDK inhibitor inhibits CDK1, CDK2, CDK7, and/or CDK9. In certain embodiments, the CDK inhibitor is flavopiridol, indisulam, AZD5438, SNS -032, SCH 727965 (Dinaciclib), JNJ-7706621, indirubin, or seliciclib. In one embodiment, the CDK inhibitor is not flavopiridol.

In one embodiment, the anti-cancer agent other than a cell-cycle inhibitor is 4-hydroxyperoxycyclophosphoramide, 5-fluorouracil (5-FU), 5-fluorodeoxyuridine (5-FUdR), 5-azacytidine, 6-mercaptopurine, 6-thioguanine, actinomycin D, amsacrine, bis-chloroethylnitrosourea, bleomycin, bryostatin-1, busulfan, carboplatin (Paraplatin®), chlorambucil, cisplatin (Platinol®), cetuximab (Erbitux®), colchicine, cyclophosphamide, cytarabine, cytosine arabinoside, dacarbazine, daunorubicin, daunomycin, dactinomycin, deoxycoformycin, diethylstilbestrol (DES), doxorubicin, etoposide (VP-16), epirubicin, esorubicin, fluorouracil (5-FU, Adrucil), gemcitabine, hexamethylmelamine, hydroxyprogesterone, hydroxyurea, idarubicin, ifosfamide, irinotecan, mafosfamide, melphalan, methotrexate (MTX), methylcyclohexylnitrosourea, mithramycin, mitomycin C, mitoxantrone, nitrogen mustards, paclitaxel (Taxol®), pentamethylmelamine, prednisone, procarbazine, tamoxifen, taxol, teniposide, testosterone, trimetrexate, topotecan, vincristine, or vinblastine.

In one embodiment, the HPV+ patient is administered radiation therapy, or is administered a surgery to treat the cancer. In some embodiments, the patient is administered one or more of a radiation therapy, a surgery to treat a cancer or an anti-cancer agent that is not a CDK inhibitor.

In one embodiment, the HPV− patient is further administered radiation therapy, or is further administered a surgery to treat the cancer.

In certain embodiments, the subject has a localized cancer, e.g., a localized cancer of the head or neck. In other embodiments, the subject has metastatic cancer. In certain embodiments, the subject is further evaluated for the presence of one or more of the alterations, e.g., mutations, disclosed herein. In one embodiment, the treatment of the subject is modified, e.g., decreased, discontinued, or otherwise altered, in response to the detection of one or more of the alterations, e.g., mutations, described herein.

In one embodiment, the HPV− patient is further determined to have a mutation in a cell cycle gene, such as a CDKN2A or CDKN2B gene or a CCND1 gene. In one embodiment, the HPV− patient has a loss-of-function mutation in a CDKN2A gene or a CDKN2B gene, and in another embodiment, the HPV− patient has a gain-of-function mutation in a CCND1 gene. In one embodiment, the HPV− patient has a mutation listed in Table 4.

In one embodiment, the HPV+ patient is further determined to have a mutation in the PI3K pathway. For example, the HPV+ patient can be determined to have a mutation in a PIK3CA gene, a PTEN gene, or an STK11 gene. In one embodiment, the patient is treated with an mTOR inhibitor, a PI3K inhibitor, or a PI3K-mTOR inhibitor.

In one embodiment, an HPV− subject is determined to have an alteration in a gene in the PI3K pathway, such as a mutation in a PIK3CA gene, a PTEN (phosphatase and tensin homolog) gene, or an STK11 (serine/threonine kinase 11) gene, and the subject is further administered an mTOR inhibitor, a PI3K inhibitor, or a PI3K-mTOR inhibitor. In another aspect, the invention features a method of evaluating a subject (e.g., a patient) who has a cancer, such as a head and neck cancer, e.g., an HNSCC, e.g., for an appropriate therapy to treat the cancer. The method includes: acquiring information or knowledge of the presence of HPV in the subject (e.g., acquiring information from a sample from the subject that identifies a HPV as being present in the subject); wherein:

the presence of HPV indicates that the patient is less likely to respond to treatment with an agent that targets a cell cycle gene, e.g., a CDK inhibitor; and/or the absence of HPV indicates that the patient is more likely to respond to treatment with an agent that targets a cell cycle gene, e.g., a CDK inhibitor.

The method can further include the step(s) of identifying (e.g., evaluating, diagnosing, screening, and/or selecting) the subject as being positively correlated with increased risk for, or having, a cancer associated with the mutant cell cycle gene. In one embodiment, the subject is identified or selected as likely or unlikely to respond to a treatment, e.g., treatment with a cell-cycle inhibitor.

The method can further include treating the subject with an anti-cancer agent, e.g., an anti-cancer agent as described herein.

In one embodiment, the CDK inhibitor inhibits one or both of a CDK4 or CDK6 inhibitor, e.g., inhibits CDK4 and CDK6, e.g., a CDK4/6 inhibitor. Exemplary CDK4/6 inhibitors include, e.g., LEE011 (Novartis), LY-2835219 and PD 0332991 (Pfizer). In one embodiment, the CDK inhibitor inhibits CDK1, CDK2, CDK7, and/or CDK9. In certain embodiments, the CDK inhibitor is flavopiridol, indisulam, AZD5438, SNS -032, SCH 727965 (Dinaciclib), JNJ-7706621, indirubin, or seliciclib. In one embodiment, the CDK inhibitor is not flavopiridol.

In one embodiment, the anti-cancer agent other than a cell-cycle inhibitor is 4-hydroxyperoxycyclophosphoramide, 5-fluorouracil (5-FU), 5-fluorodeoxyuridine (5-FUdR), 5-azacytidine, 6-mercaptopurine, 6-thioguanine, actinomycin D, amsacrine, bis-chloroethylnitrosurea, bleomycin, bryostatin-1, busulfan, carboplatin (Paraplatin®), chlorambucil, cisplatin (Platinol®), cetuximab (Erbitux®), colchicine, cyclophosphamide, cytarabine, cytosine arabinoside, dacarbazine, daunorubicin, daunomycin, dactinomycin, deoxycoformycin, diethylstilbestrol (DES), doxorubicin, etoposide (VP-16), epirubicin, esorubicin, fluorouracil (5-FU, Adrucil), gemcitabine, hexamethylmelamine, hydroxyprogesterone, hydroxyurea, idarubicin, ifosfamide, irinotecan, mafosfamide, melphalan, methotrexate (MTX), methylcyclohexylnitrosurea, mithramycin, mitomycin C, mitoxantrone, nitrogen mustards, paclitaxel (Taxol®), pentamethylmelamine, prednisone, procarbazine, tamoxifen, taxol, teniposide, testosterone, trimetrexate, topotecan, vincristine, or vinblastine.

The method can further include acquiring, e.g., directly or indirectly, a sample from a patient and evaluating the sample for the presence of a mutant gene as described herein.

In one embodiment, a subject having a cancer, e.g., a head and neck squamous cell carcinoma (HNSCC), is evaluated for the responsiveness to an agent that targets a cell-cycle gene. For example, a subject identified as HPV– who is administered a CDK inhibitor can be monitored at regular intervals, e.g., monthly, or once every three, six, 8 or 12 months, or at shorter or longer intervals, for a response to the cancer treatment. If during the course of therapy, the subject fails to respond to therapy, the patient can be administered an alternative, course of therapy.

In one embodiment, a subject having a cancer, e.g., a head and neck squamous cell carcinoma (HNSCC), who is positive or negative of HPV, is evaluated for the presence of a mutant gene, such as a mutant cell cycle gene. A subject identified as HPV– and as not having a mutant cell cycle gene can be administered a chemotherapeutic agent other than an agent that targets a mutant cell cycle gene, or a gene or gene product downstream of the cell cycle gene, and the patient can be monitored at regular intervals, e.g., monthly, or once every three, six, 8 or 12 months, or at shorter or longer intervals, for the presence of a mutant cell cycle gene. If during the course of therapy, the subject is found to carry a mutation in a cell cycle gene, the subject can stop receiving the first therapy, or can be administered a decreased dose of the first therapy.

In certain embodiments, the subject is a patient or patient population that has participated in a clinical trial. In one embodiment, the subject has participated in a clinical trial for evaluating a CDK inhibitor. In one embodiment, the clinical trial is discontinued or terminated. In one embodiment, the subject responded favorably to the clinical trial, e.g., experienced an improvement in at least one symptom of a cancer (e.g., decreased in tumor size, rate of tumor growth, increased survival). In other embodiments, the subject did not respond in a detectable way to the clinical trial. In one embodiment, the presence or absence of HPV identifies the patient as being a candidate to receive treatment with a CDK inhibitor, or an anti-cancer agent that is not a CDK inhibitor. For example, if a patient is HPV–, the patient is identified as a candidate to receive treatment with a CDK inhibitor. In another embodiment, the further identification of the presence of a mutant cell cycle gene, such as a mutant CDKN2A gene or CDKN2B gene, or a mutant CCND1 gene, further confirms that the patient is a candidate to receive treatment with a CDK inhibitor.

In a related aspect, a method of evaluating a patient or a patient population is provided. The method includes: identifying, selecting, or obtaining information or knowledge that the patient or patient population has participated in a clinical trial; acquiring information or knowledge of the presence of HPV in the patient or patient population; optionally acquiring genotype information of the subject that identifies a mutant gene, e.g., a cell cycle gene or PI3K pathway gene as being present in the subject; optionally acquiring a sequence for a nucleic acid molecule identified herein (e.g., a nucleic acid molecule that includes a mutant sequence in a cell cycle gene); or detecting the presence of a mutant nucleic acid or polypeptide in the subject, wherein the absence of HPV in the patient identifies the patient or patient population as a candidate to receive treatment with a CDK inhibitor, and wherein the presence of HPV identifies the patient or patient population as a candidate to receive treatment with an anti-cancer agent other than a CDK inhibitor.

In certain embodiments, the subject is a patient or patient population that has participated in a clinical trial. In one embodiment, the subject has participated in a clinical trial for evaluating a cell-cycle inhibitor. In one embodiment, the clinical trial is discontinued or terminated. In one embodiment, the subject responded favorably to the clinical trial, e.g., experienced an improvement in at least one symptom of a cancer (e.g., decreased in tumor size, rate of tumor growth, increased survival). In other embodiments, the subject did not respond in a detectable way to the clinical trial.

In some embodiments, the method further includes identifying the patient as HPV– and treating the subject with a cell cycle inhibitor, e.g., an inhibitor of CDK4 or CDK6, such as described herein, or identifying the patient as HPV+ and treating the subject with an anti-cancer agent other than a cell cycle inhibitor, such as cisplatin (Platinol), Cetuximab (Erbitux), fluorouracil (5-FU, Adrucil), carboplatin (Paraplatin), or paclitaxel (Taxol).

In yet another aspect, the invention features a method of evaluating a patient. The method includes:

selecting a patient on the basis that the patient has participated in a clinical trial or has been treated for a cancer, such as a head and neck cancer (e.g., HNSCC);

acquiring information that identifies the patient as HPV+ or HPV–, where (i) identification of the subject as being HPV– identifies the patient as more likely to have improved cancer symptoms following treatment with a CDK inhibitor, and/or (ii) identification of the subject as being HPV+ identifies the patient as being less likely to have improved cancer symptoms following treatment with a CDK inhibitor.

In one embodiment, the subject is determined to be HPV–, and the subject is further administered a CDK inhibitor. In another embodiment, the subject is determined to be HPV+, and the subject is further administered an anti-cancer agent other than a CDK inhibitor.

In one embodiment, the CDK inhibitor inhibits one or both of a CDK4 or CDK6 inhibitor, e.g., inhibits CDK4 and CDK6, e.g., a CDK4/6 inhibitor. Exemplary CDK4/6 inhibitors include, e.g., LEE011 (Novartis), LY-2835219 and PD 0332991 (Pfizer). In one embodiment, the CDK inhibitor inhibits CDK1, CDK2, CDK7, and/or CDK9. In certain embodiments, the CDK inhibitor is flavopiridol, indisulam, AZD5438, SNS -032, SCH 727965 (Dinaciclib), JNJ-7706621, indirubin, or seliciclib.

In one embodiment, the anti-cancer agent other than a cell-cycle inhibitor is 4-hydroxyperoxycyclophosphoramide, 5-fluorouracil (5-FU), 5-fluorodeoxyuridine (5-FUdR), 5-azacytidine, 6-mercaptopurine, 6-thioguanine, actinomycin D, amsacrine, bis-chloroethylnitrosurea, bleomycin, bryostatin-1, busulfan, carboplatin (Paraplatin®), chlorambucil, cisplatin (Platinol®), cetuximab (Erbitux®), colchicine, cyclophosphamide, cytarabine, cytosine arabinoside, dacarbazine, daunorubicin, daunomycin, dactinomycin, deoxycoformycin, diethylstilbestrol (DES), doxorubicin, etoposide (VP-16), epirubicin, esorubicin, fluorouracil (5-FU, Adrucil), gemcitabine, hexamethylmelamine, hydroxyprogesterone, hydroxyurea, idarubicin, ifosfamide, irinotecan, mafosfamide, melphalan, methotrexate (MTX), methylcyclohexylnitrosurea, mithramycin, mitomycin C, mitoxantrone, nitrogen mustards, paclitaxel (Taxol®), pentamethylmelamine, prednisone, procarbazine, tamoxifen, taxol, teniposide, testosterone, trimetrexate, topotecan, vincristine, or vinblastine.

In one embodiment, the HPV+ patient is administered radiation therapy, or is administered a surgery to treat the cancer. In some embodiments, the patient is administered one or more of a radiation therapy, a surgery to treat a cancer or an anti-cancer agent that is not a CDK inhibitor.

In one embodiment, the HPV− patient is further administered radiation therapy, or is further administered a surgery to treat the cancer.

In one embodiment, the HPV− patient is further determined to have a mutation in a cell cycle gene, such as a CDKN2A or CDKN2B gene, or a CCND1 gene. In one embodiment, the HPV− patient has a mutation in the CDKN2A gene or CDKN2B gene, and in another embodiment, the HPV− patient has a gain-of-function mutation in the CCND1 gene. In one embodiment, the HPV− patient is determined to have a mutation listed in Table 4.

In one embodiment, the HPV+ patient is further determined to have a mutation in the PI3K pathway. For example, the HPV+ patient can be determined to have a mutation in a PIK3CA gene, a PTEN gene, or an STK11 gene. In one embodiment, the patient is treated with an mTOR inhibitor, a PI3K inhibitor, or a PI3K-mTOR inhibitor.

In one embodiment, an HPV− subject is determined to have an alteration in a gene in the PI3K pathway, such as a mutation in a PIK3CA gene, a PTEN (phosphatase and tensin homolog) gene, or an STK11 (serine/threonine kinase 11) gene, and the subject is further administered an mTOR inhibitor, a PI3K inhibitor, or a PI3K-mTOR inhibitor.

Methods described herein can include providing a report, such as in electronic, web-based, or paper form, to the cancer patient, e.g. to the HNSCC patient, or to another person or entity, e.g., a caregiver, e.g., a physician, e.g., an oncologist, a hospital, clinic, third-party payor, insurance company or government office. The report can include output from the method, e.g., the indication of presence or absence of a HPV in a patient with HNSCC as described herein. In one embodiment, a report is generated, such as in paper or electronic form, which identifies the presence or absence of HPV in a patient, and optionally, a recommended course of therapy. In one embodiment, the report includes an identifier for the patient from which the sequence was obtained. In one embodiment, the report is in web-based form.

The report can also include information on the HPV status and/or the role of a sequence, e.g., a mutant gene, such as a mutant cell cycle gene, as described herein. Such information can include information on prognosis, resistance, or potential or suggested therapeutic options. The report can include information on the likely effectiveness of a therapeutic option, the acceptability of a therapeutic option, or the advisability of applying the therapeutic option to a patient, e.g., a patient having a sequence, alteration or mutation identified in the test, and in embodiments, identified in the report. For example, the report can include information, or a recommendation on, the administration of a drug, e.g., the administration of a preselected dosage or in a preselected treatment regimen, e.g., in combination with other drugs, to the patient. In an embodiment, not all mutations identified in the method are identified in the report. For example, the report can be limited to mutations in genes having a preselected level of correlation with the occurrence, prognosis, stage, or susceptibility of the cancer to treatment, e.g., with a preselected therapeutic option. The report can be delivered, e.g., to an entity described herein, within 7, 14, or 21 days from receipt of the sample by the entity practicing the method.

Thus, in yet another aspect, the invention features a method for generating a personalized cancer treatment report. The method includes:

acquiring, e.g., obtaining, a sample from a subject having a cancer, e.g., a head and neck cancer (e.g., an HNSCC), for example, by determining whether the subject is HPV− or HPV+, and selecting a treatment based on the whether the subject is HPV− or HPV+. In one embodiment, the subject is HPV−, and a CDK inhibitor is selected as a treatment. In another embodiment, the subject is HPV+, and an anti-cancer agent other than a CDK inhibitor is selected as a treatment. In another embodiment, the subject, e.g., a patient, is further administered the selected method of treatment.

In one embodiment, the method further includes providing a report to another party. The other party can be, for example, the subject, a caregiver, a physician, an oncologist, a hospital, clinic, third-party payor, insurance company or a government office. In some embodiments, the report is in electronic, web-based, or paper form. In one embodiment, the report, or a separate report, identifies the presence or absence of HPV in the subject, and optionally includes an identifier for the subject from which the information was obtained. For example, the report can contain one or more of the following: (i) information on the HPV status of the subject; (ii) information on prognosis, resistance, or potential or suggested therapeutic options; (iii) information on the likely effectiveness of a therapeutic option, (iv) the acceptability of a therapeutic option, or the advisability of applying the therapeutic option to a patient; or (v) information, or a recommendation on, the administration of a drug.

In one embodiment, the subject is determined to be HPV− and a CDK inhibitor is selected for treating the subject. In another embodiment, the subject is determined to be HPV+ and an anti-cancer agent other than a CDK inhibitor is selected for treating the subject.

Alternatively, or in combination with, the aforesaid method of generating a report, the method includes:

acquiring (e.g., obtaining) a sample, e.g., a tumor sample, from a subject having HNSCC, for example, detecting the presence of an alteration as described herein in the sample, and selecting a treatment based on the alteration (e.g., the mutation) identified. In one embodiment, the report is generated that annotates the selected treatment, or that lists, e.g., in order of preference, two or more treatment options based on the mutation identified. In another embodiment, the subject, e.g., a patient, is further administered the selected method of treatment.

In one embodiment, a report is generated to memorialize each time a patient is tested for the presence of HPV, or for the presence of a mutation in a cell cycle gene. For example, a patient who is determined not to have HPV can be administered a cell cycle inhibitor, such as a CDK inhibitor to treat an HNSCC. The patient can be reevaluated at intervals, such as every month, every two months, every six months or every year, or more or less frequently, to monitor the patient for an improvement in cancer symptoms. In some embodiments, if the patient does not respond to treatment with the CDK inhibitor, the patient's therapy can be adjusted to incorporate or substitute alternative cancer therapies. The report can record at least the treatment history of the patient.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and the example are illustrative only and not intended to be limiting.

The details of one or more embodiments featured in the invention are set forth in the accompanying drawings and the description below. Other features, objects, and advantages featured in the invention will be apparent from the description and drawings, and from the claims.

BRIEF DESCRIPTION OF DRAWING

FIGS. 2A and 2B are a list of 182 genes sequenced across the entire coding sequence (FIG. 2A), and 14 genes sequenced across selected introns (FIG. 2B).

DETAILED DESCRIPTION

Figure 1:
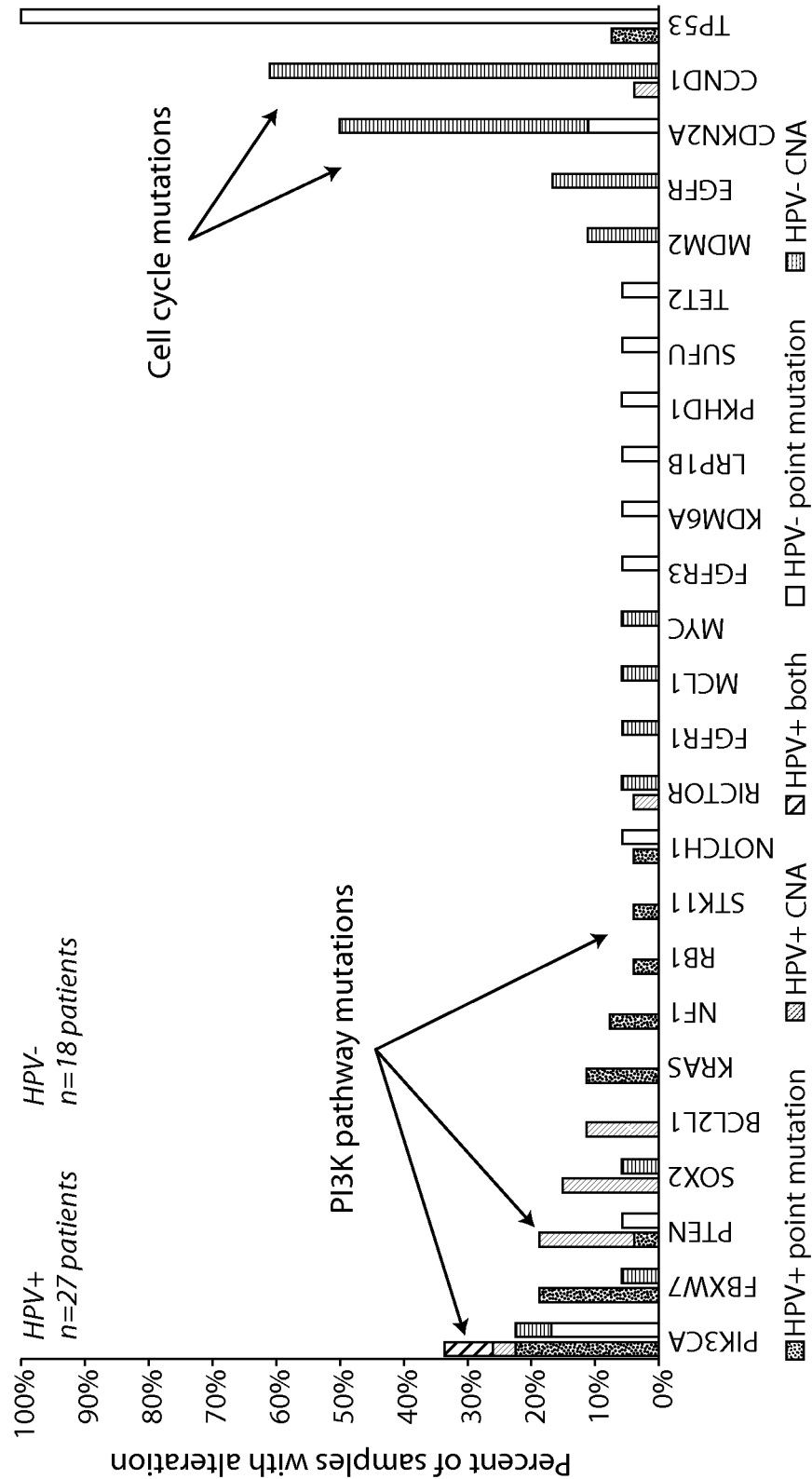
FIG. 1 is a graph depicting the correlation between HPV status and classes of gene mutations.

The invention is based, at least in part, on the discovery that HPV status is predictive of the underlying genotype in subjects having a cancer, such as a cancer of the head and neck, e.g., a head and neck squamous cell carcinoma (HNSCC). HNSCC patients who are HPV− are more likely to carry mutations in cell cycle genes such as CDKN2A, CDKN2B, CCNE1, CCND1, CCND2, CCND3, CDK4 or CKD6, and are therefore more likely to respond to treatment with a cell cycle inhibitor, such as a CDK inhibitor. Determination that the subject is HPV− is sufficient to conclude that the subject is a candidate to receive treatment with a CDK inhibitor, e.g., a CDK4/6 inhibitor. Further genomic profiling is not necessary before making the determination that the subject is likely to respond to treatment with a CDK inhibitor, or before administering the CDK inhibitor.

Cancers known collectively as head and neck cancers usually begin in the squamous cells that line the moist, mucosal surfaces inside the head and neck (for example, inside the mouth, the nose, and the throat). These squamous cell cancers are often referred to as squamous cell carcinomas of the head and neck (or head and neck squamous cell carcinomas, HNSCC, which term is used herein). HNSCC includes squamous cell carcinomas of the mouth, nasopharynx (where the nasal cavity and the eustacian tubes connect with the upper part of the throat), oropharynx (the middle part of the throat that includes the soft palate, the base of the tongue, and the tonsils), hypopharynx (the pyriform sinuses, the posterior pharyngeal wall and the postcricoid area), larynx, and trachea.

Squamous cell carcinomas of the mouth include, for example, cancers of the inner lip, tongue, floor of the mouth, gingivae, and hard palate. Squamous cell carcinomas of the head and neck can also begin in the salivary glands.

There are more than 100 different types of human papillomaviruses (HPVs) and the genomes of over 80 different types have been completely sequenced. The current classification system for HPV is based on similarities in genomic sequence, and divides the HPVs into three clinical categories: (i) anogenital or mucosal; (ii) nongenital cutaneous; (iii) epidermodysplasia verruciformis (EV). The majority of HPV-related HNSCCs are associated with type 16 HPV, with types 18, 31 and 33 accounting for almost all of the remaining cases (Snow et al., Adv. Anat. Pathol. 17:394-403, 2010).

The mucosal HPV infections are classified further as latent (asymptomatic), subclinical, or clinical. Clinical lesions are grossly apparent, whereas latent infections are detected only with tests for viral DNA. Subclinical lesions are identified by application of 3-5% acetic acid and inspection under magnification. Most HPV infections are latent; clinically apparent infections usually result in warts rather than malignancies.

Nongenital cutaneous infections include common warts, plantar warts, flat warts and other skin lesions.

Epidermodysplasia verruciformis (EV) is a rare, inherited disorder that predisposes patients to widespread human papillomavirus (HPV) infection and cutaneous squamous cell carcinomas.

HPV can be detected by assays known in the art such as in situ hybridization (ISH), immunohistochemistry (IHC), PCR, dot blot, reverse line blot, DNA enzyme immunoassay, Southern blot, sequencing, Northern blot, or Western blot analysis. The detection method can detect HPV protein, DNA or RNA, e.g., mRNA, and specimen types evaluated can be frozed, fresh or FFPE (formalin fixed paraffin embedded) tissue; saliva; or cytological preparations.

In one embodiment, HPV is detected by IHC to detect the p16 protein (encoded by CDKN2A), a component of the retinoblastoma tumor suppressor pathway. The protein p16 is strongly and diffusely expressed in about 93% of HPV-associated squamous cell carcinomas (SCCs) but is absent in HPV-negative carcinomas.

In other embodiments, PCR (polymerase chain reaction) or RFLP (restriction fragment length polymorphism) is performed to detect a specific HPV type in a subject.

Accordingly, the invention provides, at least in part, methods of treating a cancer, such as HNSCC, according to whether a subject is HPV− or HPV+. If the subject is HPV−, the subject is administered an anti-cancer agent that targets a cell cycle gene, such as a CDK inhibitor, to treat the cancer.

In one aspect, the invention features compositions and methods to identify new CDK inhibitors; to treat or prevent a cancer, e.g., an HNSCC; as well as to methods and assays for evaluating a cancer (e.g., evaluating one or more of: cancer progression, cancer treatment response or resistance to cancer treatment; selection of a treatment option, stratification of a patient population, and/or more effective monitoring, treatment or prevention of cancer).

The cell cycle gene CDKN2A (Cyclin Dependent Kinase Inhibitor 2A) inhibits CDK4 in vivo. The invention is based, at least in part, on the discovery that 50% to 60% of HNSCC patients who are HPV− also carry a loss-of-function mutation in the CDKN2A gene, which results in aberrant cell-cycle activity. Thus, HNSCC patients who are HPV− can be administered a CDK inhibitor, such as a CDK4 or CDK6 inhibitor. The HNSCC patient can optionally be tested for the presence of a mutation in the CDKN2A gene. Without being bound by theory, loss-of-function mutations in CDKN2A frequently resulted from copy number alterations, but a low frequency of point mutations was also observed.

The cell cycle gene CCND1 (Cyclin D1) encodes a protein that binds CDK4 and inhibits CDK4/cyclin D1 enzymes in vivo. The invention is based, at least in part, on the discovery that 60% to 70% of HNSCC patients who are HPV− also carry a gain-of-function mutation in the CCND1 gene, which results in aberrant cell-cycle activity. Thus, HNSCC patients who are HPV− can be administered a CDK inhibitor, such as a CDK4 or CDK6 inhibitor. The HNSCC patient can optionally be tested for the presence of mutation in the CCND1 gene. The gain-of-function mutations in CCND1 are typically the result of copy number alterations, but on rare occasions, a point mutation may also cause a gain of function phenotype.

Other mutations found to correlate with HPV status are described in Tables 1 and 4. The invention therefore also provides, at least in part, isolated nucleic acid molecules containing a mutation described in Table 1 or Table 4, nucleic acid constructs, and host cells containing the nucleic acid molecules; purified mutant polypeptides comprising a mutation described in Table 1 or Table 4, and binding agents, e.g., antibodies and small molecule compounds that specifically bind the mutant proteins. The invention also provides detection reagents (e.g., probes, primers, antibodies, kits); screening assays for identifying novel inhibitors; as well as methods, assays and kits for evaluating, identifying, assessing and/or treating a subject having a cancer, e.g., a cancer having a mutation disclosed herein.

Certain terms are defined. Additional terms are defined throughout the specification.

As used herein, the articles "a" and "an" refer to one or to more than one (e.g., to at least one) of the grammatical object of the article.

The term "or" is used herein to mean, and is used interchangeably with, the term "and/or," unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

"Acquire" or "acquiring" as the terms are used herein, refer to obtaining possession of a physical entity, e.g., a sample, or a value, e.g., a numerical value, or nucleic acid sequence or amino acid sequence, by "directly acquiring" or "indirectly acquiring" the physical entity or value. "Directly acquiring" means performing a process (e.g., performing a synthetic or analytical method, e.g., a sequencing reaction) to obtain the physical entity or value. "Indirectly acquiring" refers to receiving the physical entity or value from another party or source (e.g., a third party laboratory that directly acquired the physical entity or value). Directly acquiring a physical entity includes performing a process that includes a physical change in a physical substance, e.g., a starting material, or a nucleic acid sample. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent.

"Acquiring a sequence" as the term is used herein, refers to obtaining possession of a nucleotide sequence or amino acid sequence, by "directly acquiring" or "indirectly acquiring" the sequence. "Directly acquiring a sequence" means performing a process (e.g., performing a synthetic or analytical method) to obtain the sequence, such as performing a sequencing method (e.g., a Next Generation Sequencing (NGS) method). "Indirectly acquiring a sequence" refers to receiving information or knowledge of, or receiving, the sequence from another party or source (e.g., a third party laboratory that directly acquired the sequence). The sequence acquired need not be a full sequence, e.g., sequencing of at least one nucleotide, or obtaining information or knowledge, that identifies a mutation disclosed herein as being present in a subject constitutes acquiring a sequence.

Directly acquiring a sequence includes performing a process that includes a physical change in a physical substance, e.g., a starting material, such as a tissue sample, e.g., a biopsy, or an isolated nucleic acid (e.g., DNA or RNA) sample. Exemplary changes include making a physical entity from two or more starting materials, shearing or fragmenting a substance, such as a genomic DNA fragment; separating or purifying a substance (e.g., isolating a nucleic acid sample from a tissue); combining two or more separate entities into a mixture, performing a chemical reaction that includes breaking or forming a covalent or non-covalent bond. Directly acquiring a value includes performing a process that includes a physical change in a sample or another substance as described above.

"Acquiring a sample" as the term is used herein, refers to obtaining possession of a sample, e.g., a tissue sample or nucleic acid sample, by "directly acquiring" or "indirectly acquiring" the sample. "Directly acquiring a sample" means performing a process (e.g., performing a physical method such as a surgery or extraction) to obtain the sample. "Indirectly acquiring a sample" refers to receiving the sample from another party or source (e.g., a third party laboratory that directly acquired the sample). Directly acquiring a sample includes performing a process that includes a physical change in a physical substance, e.g., a starting material, such as a tissue, e.g., a tissue in a human patient or a tissue that has was previously isolated from a patient. Exemplary changes include making a physical entity from a starting material, dissecting or scraping a tissue; separating or purifying a substance (e.g., a sample tissue or a nucleic acid sample); combining two or more separate entities into a mixture; performing a chemical reaction that includes breaking or forming a covalent or non-covalent bond. Directly acquiring a sample includes performing a process that includes a physical change in a sample or another substance, e.g., as described above.

"Binding entity" means any molecule to which molecular tags can be directly or indirectly attached that is capable of specifically binding to an analyte. The binding entity can be an affinity tag on a nucleic acid sequence. In certain embodiments, the binding entity allows for separation of the nucleic acid from a mixture, such as an avidin molecule, or an antibody that binds to the hapten or an antigen-binding fragment thereof. Exemplary binding entities include, but are not limited to, a biotin molecule, a hapten, an antibody, an antibody binding fragment, a peptide, and a protein.

"Complementary" refers to sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In certain embodiments, the first region comprises a first portion and the second region comprises a second portion, whereby, when the first and second portions are arranged in an antiparallel fashion, at least about 50%, at least about 75%, at least about 90%, or at least about 95% of the nucleotide residues of the first portion are capable of base pairing with nucleotide residues in the second portion. In other embodiments, all nucleotide residues of the first portion are capable of base pairing with nucleotide residues in the second portion.

The term "cancer" or "tumor" is used interchangeably herein. These terms refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell, such as a leukemia cell. These terms include a solid tumor, a soft tissue tumor, or a metastatic lesion. As used herein, the term "cancer" includes premalignant, as well as malignant cancers.

Cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

"Chemotherapeutic agent" means a chemical substance, such as a cytotoxic or cytostatic agent, that is used to treat a condition, particularly cancer.

As used herein, "cancer therapy" and "cancer treatment" are synonymous terms.

As used herein, "chemotherapy" and "chemotherapeutic" and "chemotherapeutic agent" are synonymous terms.

As used herein, a "cell-cycle gene" is a gene whose activity affects regulation of the cell cycle, or whose expression levels vary periodically with the cell-cycle.

The terms "homology" or "identity," as used interchangeably herein, refer to sequence similarity between two polynucleotide sequences or between two polypeptide sequences, with identity being a more strict comparison. The phrases "percent identity or homology" and "% identity or homology" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value there between. Identity or similarity can be determined by comparing a position in each sequence that can be aligned for purposes of comparison. When a position in the compared sequence is occupied by the same nucleotide base or amino acid, then the molecules are identical at that position. A degree of similarity or identity between polynucleotide sequences is a function of the number of identical or matching nucleotides at positions shared by the polynucleotide sequences. A degree of identity of polypeptide sequences is a function of the number of identical amino acids at positions shared by the polypeptide sequences. A degree of homology or similarity of polypeptide sequences is a function of the number of amino acids at positions shared by the polypeptide sequences. The term "substantially identical," as used herein, refers to an identity or homology of at least 75%, at least 80%, at least 85%, at least 90%, 91%, 92%, 93%, 94%, 95%, 96%, 97%, 98%, 99%, or more.

"Likely to" or "increased likelihood," as used herein, refers to an increased probability that an item, object, thing or person will occur. Thus, in one example, a subject that is likely to respond to treatment with a cell cycle inhibitor, such as a CDK inhibitor, has an increased probability of responding to treatment with the cell cycle inhibitorCDK inhibitor relative to a reference subject or group of subjects.

"Unlikely to" refers to a decreased probability that an event, item, object, thing or person will occur with respect to a reference. Thus, a subject that is unlikely to respond to treatment with a cell cycle inhibitor, such as a CDK inhibitor, has a decreased probability of responding to treatment with the cell cycle inhibitor relative to a reference subject or group of subjects.

As used herein, "genomic profiling" means sequencing all or a part of the genome of a subject, such as to identify the nucleotide sequence of genes or a subset of genes in the subject, such as to identify genomic alterations (e.g., mutations) that would identify the subject as a candidate to receive certain drugs or other therapeutic agents. Genomic profiling can be performed by a method described herein, such as by a next-generation sequencing method, or a massively parallel sequencing method.

"Sequencing" a nucleic acid molecule requires determining the identity of at least 1 nucleotide in the molecule. In embodiments, the identity of less than all of the nucleotides in a molecule are determined. In other embodiments, the identity of a majority or all of the nucleotides in the molecule is determined.

"Next-generation sequencing or NGS or NG sequencing" as used herein, refers to any sequencing method that determines the nucleotide sequence of either individual nucleic acid molecules (e.g., in single molecule sequencing) or clonally expanded proxies for individual nucleic acid molecules in a highly parallel fashion (e.g., greater than $10^5$ molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. (2010) *Nature Biotechnology Reviews* 11:31-46, incorporated herein by reference. Next generation sequencing can detect a variant present in less than 5% of the nucleic acids in a sample.

"Sample," "tissue sample," "patient sample," "patient cell or tissue sample" or "specimen" each refers to a collection of similar cells obtained from a tissue of a subject or patient. The source of the tissue sample can be solid tissue as from a fresh, frozen and/or preserved organ, tissue sample, biopsy, or aspirate; blood or any blood constituents; bodily fluids such as cerebral spinal fluid, amniotic fluid, peritoneal fluid or interstitial fluid; or cells from any time in gestation or development of the subject. The tissue sample can contain compounds that are not naturally intermixed with the tissue in nature such as preservatives, anticoagulants, buffers, fixatives, nutrients, antibiotics or the like. In one embodiment, the sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample.

A "tumor nucleic acid sample" as used herein, refers to nucleic acid molecules from a tumor or cancer sample. Typically, it is DNA, e.g., genomic DNA, or cDNA derived from RNA, from a tumor or cancer sample. In certain embodiments, the tumor nucleic acid sample is purified or isolated (e.g., it is removed from its natural state).

A "control" or "reference" "nucleic acid sample" as used herein, refers to nucleic acid molecules from a control or reference sample. Typically, it is DNA, e.g., genomic DNA, or cDNA derived from RNA, not containing the alteration or variation in the gene or gene product, e.g., not containing a mutation in a cell cycle gene. In certain embodiments, the reference or control nucleic acid sample is a wild-type or a non-mutated sequence. In certain embodiments, the reference nucleic acid sample is purified or isolated (e.g., it is removed from its natural state). In other embodiments, the reference nucleic acid sample is from a non-tumor sample, e.g., a blood control, a normal adjacent tumor (NAT), or any other non-cancerous sample from the same or a different subject.

Headings, e.g., (a), (b), (i) etc, are presented merely for ease of reading the specification and claims. The use of headings in the specification or claims does not require the steps or elements be performed in alphabetical or numerical order or the order in which they are presented.

Various aspects of the invention are described in further detail below. Additional definitions are set out throughout the specification.

Evaluation of Subjects

Subjects, e.g., patients, can be evaluated for the presence of an HPV molecule. For example, a sample from a subject, such as a blood or urine sample, can be evaluated to identify an HPV nucleic acid or HPV protein in the sample. For example, an HPV nucleic acid can be identified by PCR, Northern blot analysis, or sequencing of nucleic acids in the sample. HPV protein can be identified, e.g., by Western blot analysis. A sample from a subject can be, for example, a blood or serum sample, or a urine sample, or a tissue sample, such as a tumor tissue sample, such as from a biopsy, or a buccal swab.

In some embodiments, subjects, e.g., patients, can be evaluated for the presence of a mutant gene. A patient can be evaluated, for example, by determining the genomic sequence of the patient, e.g., by an NGS method. Alternatively, or in addition, evaluation of a patient can include directly assaying for the presence of a mutant gene in the patient, such as by an assay to detect a mutant nucleic acid (e.g., DNA or RNA), such as by, Southern blot, Northern blot, or RT-PCR, e.g., qRT-PCR. Alternatively, or in addition, a patient can be evaluated for the presence of a mutant protein, such as by immunohistochemistry, Western blot, immunoprecipitation, or immunomagnetic bead assay.

Evaluation of a patient can also include a cytogenetic assay, such as by fluorescence in situ hybridization (FISH), to identify the chromosomal rearrangement resulting in the mutant gene. For example, to perform FISH, at least a first probe tagged with a first detectable label can be designed to target a sequence in a functional domain of a gene.

Additional methods for mutant gene detection are provided below.

In one aspect, the results of a clinical trial, e.g., a successful or unsuccessful clinical trial, can be repurposed to identify agents that target a mutant gene. By one exemplary method, a candidate agent used in a clinical trial can be reevaluated to determine if the agent in the trial targets a mutant gene, or is effective to treat a tumor containing a mutant gene. For example, subjects who participated in a clinical trial for an agent, e.g., a CDK inhibitor, can be identified. Patients who experienced an improvement in symptoms, e.g., HSNCC symptoms, such as decreased tumor size, or decreased rate of tumor growth, can be evaluated for the presence of a mutation in the ligand binding domain of the gene. Patients who did not experience an improvement in cancer symptoms can also be evaluated for the presence of a mutation, such as in a cell cycle gene. Where patients carrying a mutation in a functional domain of the gene are found to have been more likely to respond to the test agent than patients who did not carry a mutation in the ligand binding domain, then the agent is determined to be an appropriate treatment option for a patient carrying the mutant gene.

"Reevaluation" of patients can include, for example, determining the genomic sequence of the patients, or a subset of the clinical trial patients, e.g., by an NGS method. Alternatively, or in addition, reevaluation of the patients can include directly assaying for the presence of a gene mutation in the patient, such as by an assay to detect a mutant nucleic acid (e.g., RNA), such as by RT-PCR, e.g., qRT-PCR. Alternatively, or in addition, a patient can be evaluated for the presence of a mutant protein, such as by immunohistochemistry, Western blot, immunoprecipitation, or immunomagnetic bead assay.

Clinical trials suitable for repurposing as described above include trials that tested CDK inhibitors, such as CDK4 or CKD6 inhibitors.

In one embodiment, the HPV molecule and/or mutant gene is detected prior to initiating, during, or after, a treatment in a subject. In one embodiment, the HPV molecule and/or mutant gene is detected at the time of diagnosis with a cancer. In other embodiments, the HPV molecule and/or mutant gene is detected at a pre-determined interval, e.g., a first point in time and at least at a subsequent point in time.

In certain embodiments, responsive to a determination of the presence of the HPV molecule and/or mutant gene, the method further includes one or more of:

(1) stratifying a patient population (e.g., assigning a subject, e.g., a patient, to a group or class);

(2) identifying or selecting the subject as likely or unlikely to respond to a treatment, e.g., a treatment as described herein;

(3) selecting a treatment option, e.g., administering or not administering a preselected therapeutic agent, e.g., an agent described herein; or (4) prognosticating the time course of the disease in the subject (e.g., evaluating the likelihood of increased or decreased patient survival).

In certain embodiments, the therapeutic agent is a cell cycle inhibitor, such as flavopiridol; indisulam; AZD5438; SNS-032; PD 0332991; SCH 727965 (Dinaciclib); LY-2835219; Seliciclib; LEE011 (Novartis); JNJ-7706621; indirubin; or PD 0332991 (Pfizer). In other embodiments, the cell-cycle inhibitor is a CDK inhibitor, such as flavopiridol; indisulam; AZD5438; SNS-032; PD 0332991; SCH 727965 (Dinaciclib); Seliciclib; JNJ-7706621; or indirubin. In yet other embodiments, the cell-cycle inhibitor is an inhibitor of CDK4 and/or CDK6, such as LEE011 (Novartis); LY-2835219; or PD 0332991 (Pfizer).

In some embodiments, the therapeutic agent is other than a cell-cycle inhibitor, such as cisplatin (Platinol), Cetuximab (Erbitux), fluorouracil (5-FU, Adrucil), carboplatin (Paraplatin), or paclitaxel (Taxol).

In certain embodiments, responsive to the determination of the presence of the mutant gene, the subject is classified as a candidate to receive treatment with an anti-cancer agent.

In one embodiment, responsive to the determination of the presence of the HPV molecule and/or the mutant gene, the subject, e.g., a patient, can further be assigned to a particular class if a mutant gene is identified in a sample of the patient. In one embodiment, the subject, e.g., a patient, is assigned to a second class if the HPV molecule and/or the mutation is not present.

In another embodiment, responsive to the determination of the presence of the HPV molecule and/or mutant gene, the subject is identified as likely to respond to a treatment as described herein.

In yet another embodiment, responsive to the determination of the presence of the HPV molecule and/or mutant gene, the method includes administering an anti-cancer agent as described herein to the subject.

In one embodiment, a subject who is determined not to carry the HPV molecule and/or a mutant gene is reevaluated at intervals, such as every month, every two months, every six months or every year, or more or less frequently, to monitor the patient for the development of a mutation in gene, e.g., in a cell-cycle gene. For example, if a patient is determined not to carry a mutant gene, then the patient can be determined to be a candidate for treatment with a first agent, such as an anti-cancer agent that acts other than by inhibiting the cell cycle. If the patient is subsequently determined to have a mutant gene, administration of the first agent to the patient can be stopped, and the patient can be administered a second agent, such as a cell-cycle inhibitor. In some embodiments, the patient continues to receive treatment with the first agent, and optionally, the patient can receive more frequent monitoring for a worsening of cancer symptoms.

Therapeutic Methods

In one embodiment, the invention features a method of treating a patient, such as an HPV– patient having a cancer, e.g., an HNSCC. The patient can have a tumor harboring a mutant gene as described herein, e.g., a mutant cell cycle gene such as a mutant CDKN2A or CDKN2B or CCND1 gene as described herein. The methods include administering an anti-cancer agent, e.g., a CDK inhibitor, alone or in combination, e.g., in combination with other chemotherapeutic agents or procedures, in an amount sufficient to reduce or inhibit the tumor cell growth, and/or treat or prevent the cancer(s), in the subject.

"Treat," "treatment," and other forms of this word refer to the administration of a CDK inhibitor, alone or in combination with a second agent to impede growth of a cancer, to cause a cancer to shrink by weight or volume, to extend the expected survival time of the subject and or time to progression of the tumor or the like. In those subjects, treatment can include, but is not limited to, inhibiting tumor growth, reducing tumor mass, reducing size or number of metastatic lesions, inhibiting the development of new metastatic lesions, prolonged survival, prolonged progression-free survival, prolonged time to progression, and/or enhanced quality of life.

As used herein, unless otherwise specified, the terms "prevent," "preventing" and "prevention" contemplate an action that occurs before a subject begins to suffer from the re-growth of the cancer and/or which inhibits or reduces the severity of the cancer.

As used herein, and unless otherwise specified, a "therapeutically effective amount" of a compound is an amount sufficient to provide a therapeutic benefit in the treatment or management of the cancer, or to delay or minimize one or more symptoms associated with the cancer. A therapeutically effective amount of a compound means an amount of therapeutic agent, alone or in combination with other therapeutic agents, which provides a therapeutic benefit in the treatment or management of the cancer. The term "therapeutically effective amount" can encompass an amount that improves overall therapy, reduces or avoids symptoms or causes of the cancer, or enhances the therapeutic efficacy of another therapeutic agent.

As used herein, and unless otherwise specified, a "prophylactically effective amount" of a compound is an amount sufficient to prevent re-growth of the cancer, or one or more symptoms associated with the cancer, or prevent its recurrence. A prophylactically effective amount of a compound means an amount of the compound, alone or in combination with other therapeutic agents, which provides a prophylactic benefit in the prevention of the cancer. The term "prophylactically effective amount" can encompass an amount that improves overall prophylaxis or enhances the prophylactic efficacy of another prophylactic agent.

As used herein, the term "patient" or "subject" refers to an animal, typically a human (i.e., a male or female of any age group, e.g., a pediatric patient (e.g., infant, child, adolescent) or adult patient (e.g., young adult, middle-aged adult or senior adult) or other mammal, such as a primate (e.g., cynomolgus monkey, rhesus monkey). When the term is used in conjunction with administration of a compound or drug, then the patient has been the object of treatment, observation, and/or administration of the compound or drug.

In certain embodiments, the cancer includes, but is not limited to, a solid tumor, a soft tissue tumor, and a metastatic lesion (e.g., a cancer as described herein). In one embodiment, the cancer is a squamous cell carcinoma of the head and neck (HNSCC).

In other embodiments, the cancer is chosen from uterine or cervical cancer or a tumor of the genitalia, such as the vulva, vagina or penis. In other embodiments the cancer is a testicular cancer, urinary bladder cancer, lung cancer, thyroid cancer, colorectal cancer, adenocarcinoma, melanoma, B cell cancer, bronchus cancer, cancer of the oral cavity or pharynx, cancer of hematological tissues, esophageal cancer, esophageal-gastric cancer, gastric cancer, kidney cancer, liver cancer, multiple myeloma, pancreatic cancer, salivary gland cancer, small bowel or appendix cancer, stomach cancer, inflammatory myofibroblastic tumors, gastrointestinal stromal tumor (GIST), and the like.

In certain embodiments, the cancer, e.g., HNSCC, is treated with a CDK inhibitor. In one embodiment, the CDK inhibitor inhibits one or both of CDK4 or CDK6. In embodiments, the CDK inhibitor is an orally active, selective CDK4/6 inhibitor with ability to block retinoblastoma (Rb) phosphorylation. Exemplary CDK4/6 inhibitors are described in, e.g., WO 2007/140222, WO 2010/020675, WO 2013/006368, WO 2013/006532, WO 2011/130232, US 2013/0150342, W2011/101409, US 2013/184285, WO2006024945, WO2006024945, and EP1256578B1, all of which are hereby incorporated by reference in their entirety.

In one embodiment, the CDK inhibitor is chosen from flavopiridol, indisulam, AZD5438, SNS-032, SCH 727965 (Dinaciclib), Seliciclib, JNJ-7706621, or indirubin. In other embodiments, the CDK inhibitor is not flavopiridol.

In another embodiment, the CDK4/6 inhibitor is chosen from LEE011 (Novartis); LY-2835219 (Eli Lilly); or PD 0332991 (Pfizer).

In one embodiment, the CDK 4/6 inhibitor has the following structure:

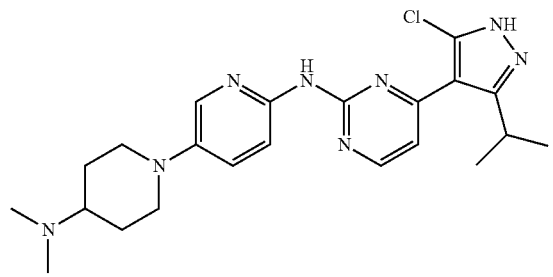

$C_{22}H_{29}ClN_8$
Mol. Wt.: 440.97 also referred to herein as LEE011. In one embodiment, the CDK 4/6 inhibitor has the following chemical name: 4-(5-chloro-3-isopropyl-1H-pyrazol-4-yl)-N-(5-(4-(dimethylamino)piperidin-1-yl)pyridin-2-yl)pyrimidin-2-amine.

In another embodiment, the CDK 4/6 inhibitor has the following structure:

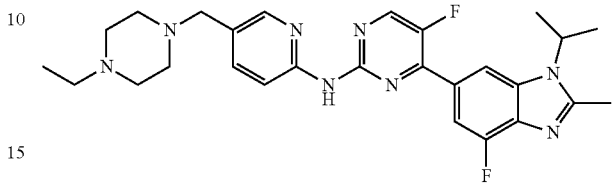

also referred to herein as LY-2835219. In one embodiment, the CDK 4/6 inhibitor has the following chemical name: (N-(5-((4-ethylpiperazin-1-yl)methyl)pyridin-2-yl)-5-fluoro-4-(4-fluoro-1-isopropyl-2-methyl-1H-benzo[d]imidazol-6-yl)pyrimidin-2-amine).

In yet another embodiment, the CDK 4/6 inhibitor has the following structure:

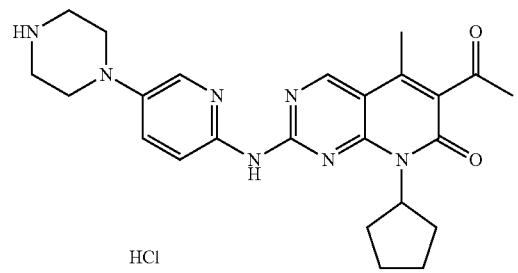 [SMILES: CC(=O)c1c(C)c2cnc(Nc3ccc(N4CCNCC4)cn3)nc2n(C2CCCC2)c1=O ; Cl]

HCl also referred to herein as PD 0332991. In one embodiment, the CDK 4/6 inhibitor has the following chemical name: 6-acetyl-8-cyclopentyl-5-methyl-2-(5-(piperazin-1-yl)pyridin-2-ylamino)pyrido[2,3-d]pyrimidin-7(8H)-one hydrochloride.

Further examples of publications describing the aforesaid inhibitors and their activities include Finn, R S et al. (2009) *Breast Cancer Res.* 11(5):R77; Zhang, Y. in Proceedings of the AACR-NCI-EORTC International Conference: Molecular Targets and Cancer Therapeutics, 2011:10 (11 Suppl): Abstract nr A236; Clinical Trial Gov. Identifier NCT01237236; and Clinical Trial Gov. Identifier NCT01394016, incorporated herein by reference.

In another embodiment, the CDK inhibitor is BAY1000394. BAY1000394 is an orally bioavailable CDK inhibitor. It inhibits the activity of cell-cycle CDKs, including CDK1, CDK2, CDK3, CDK4, and of transcriptional CDKs CDK7 and CDK9 with IC50 values in the range between 5 and 25 nM. BAY1000394 has the chemical name: 2-Butanol, 3-[[2-[[4-[[S(R)]-S-cyclopropylsulfonimidoyl]phenyl]amino]-5-(trifluoromethyl)-4-pyrimidinyl]oxy]-, (2R,3R)-; and has the following structure:

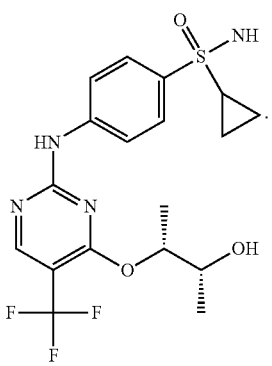

BAY 1000394 Chemical Structure
Molecular Weight: 430.44

In another embodiment, the CDK inhibitor is ZK-304709. ZK-304709 is a potent multi-target tumor growth inhibitor. ZK-304709 inhibits the activity of cell-cycle CDKs, including CDK1, CDK2, CDK4, and of transcriptional CDKs CDK7 and CDK9, with IC50 values in the nanomolar range. ZK-304709 also inhibits the activity of vascular endothelial growth factor receptor tyrosine kinases (VEGFRs), including VEGFR 1, VEGFR 2, and VEGFR3 and of platelet-derived growth factor receptor beta tyrosine kinase (PDGFR). ZK-304709 has the chemical name: (Z)-3,3-dimethyl-2'-oxo-[2,3'-biindolinylidene]-5'-sulfonamide; and has the following structure:

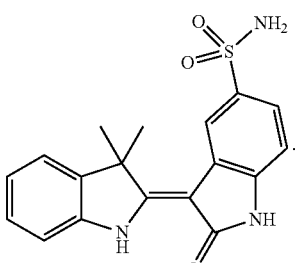

ZK-304709 Chemical Structure
Molecular Weight: 355.41

In another embodiment, the CDK inhibitor is SNS032. SNS032 inhibits the activity of cell-cycle CDKs, including CDK1, CDK2, and of transcriptional CDKs CDK4, CDK7 and CDK9. SNS-032 has low sensitivity to CDK1 and CDK4 with IC50 of 480 nM and 925 nM, respectively. SNS032 has the chemical name: N-(5-((5-tert-butyloxazol-2-yl)methylthio)thiazol-2-yl)piperidine-4-carboxamide; and has the following structure:

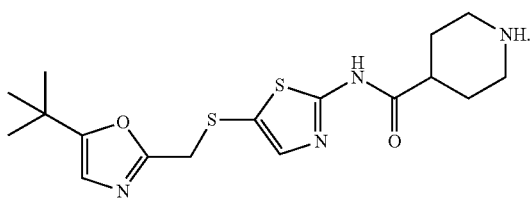

SNS032 Chemical Structure
Molecular Weight: 380.53

In another embodiment, the CDK inhibitor is seliciclib. Seliciclib inhibits the activity of CDKs, including CDK2 and CDK5. Seliciclib has the chemical name: N-(5-((5-tert-butyloxazol-2-yl)methylthio)thiazol-2-yl)piperidine-4-carboxamide; and has the following structure:

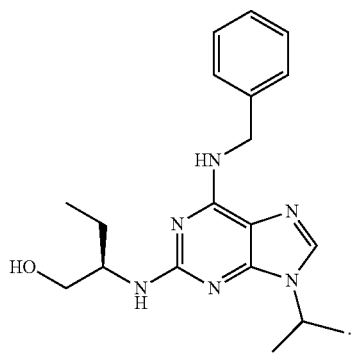

Seliciclib Chemical Structure
Molecular Weight: 354.45

In another embodiment, the CDK inhibitor is NC381. NC381 inhibits the activity of cell-cycle CDKs, including CDK4. NC381 has the following structure:

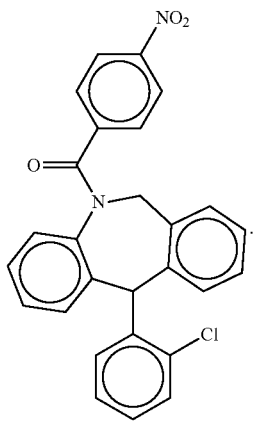

NC381 Chemical Structure
Molecular Weight: 454

In another embodiment, the CDK inhibitor is Milciclib. Milciclib is an orally bioavailable inhibitor of cyclin-dependent kinases (CDKs) and thropomyosin receptor kinase A (TRKA). Milciclib inhibits the activity of cell-cycle CDKs, including CDK1, CDK2, and CDK4. Milciclib has the chemical name: N,1,4,4-tetramethyl-8-((4-(4-methylpiperazin-1-yl)phenyl)amino)-4,5-dihydro-1H-pyrazolo[4,3-h]quinazoline-3-carboxamide; and has the following structure:

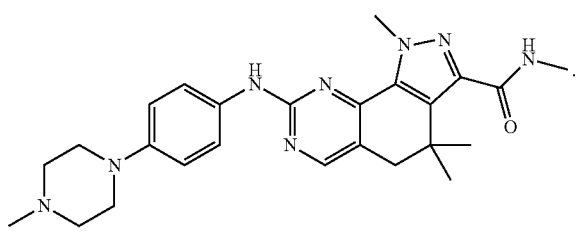

Milciclib Chemical Structure
Molecular Weight: 460.57

In another embodiment, the CDK inhibitor is ON123300. ON123300 inhibits the activity of cell-cycle CDKs, including CDK4. ON123300 has the chemical name: NH—(N—CH3piperazino)phenyl; and has the following structure:

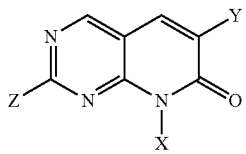

ON123300 Chemical Structure

In another embodiment, the CDK inhibitor is PD0332991/palbociclib. PD0332991/palbociclib inhibits the activity of CDKs, including CDK4 and CDK6, with IC50 of 11 nM and 16 nM, respectively. PD0332991/palbociclib has the chemical name: Ethanesulfonic acid, 2-hydroxy-, compd. with 6-acetyl-8-cyclopentyl-5-methyl-2-[[5-(1-piperazinyl)-2-pyridinyl]amino]pyrido[2,3-d]pyrimidin-7(8H)-one (1:1); and has the following structure:

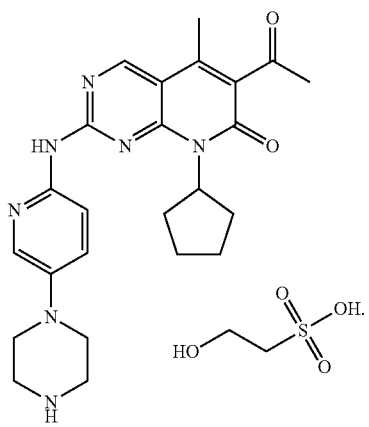

PD0332991/palbociclib Chemical Structure
Molecular Weight: 573.66

In some embodiments, an anti-cancer agent is other than a CDK inhibitor. Exemplary anti-cancer agents that are not CDK inhibitors, include, e.g., 4-hydroxyperoxycyclophosphor-amide, 5-fluorouracil (5-FU), 5-fluorodeoxyuridine (5-FUdR), 5-azacytidine, 6-mercaptopurine, 6-thioguanine, actinomycin D, amsacrine, bis-chloroethylnitrosurea, bleomycin, bryostatin-1, busulfan, carboplatin (Paraplatin®), chlorambucil, cisplatin (Platinol®), cetuximab (Erbitux®), colchicine, cyclophosphamide, cytarabine, cytosine arabinoside, dacarbazine, daunorubicin, daunomycin, dactinomycin, deoxycoformycin, diethylstilbestrol (DES), doxorubicin, etoposide (VP-16), epirubicin, esorubicin, fluorouracil (5-FU, Adrucil), gemcitabine, hexamethylmelamine, hydroxyprogesterone, hydroxyurea, idarubicin, ifosfamide, irinotecan, mafosfamide, melphalan, methotrexate (MTX), methylcyclohexylnitrosurea, mithramycin, mitomycin C, mitoxantrone, nitrogen mustards, paclitaxel (Taxol®), pentamethylmelamine, prednisone, procarbazine, tamoxifen, taxol, teniposide, testosterone, trimetrexate, topotecan, vincristine, and vinblastine.

In some embodiments, a patient is HPV+, and the patient is administered an agent to treat the HPV infection, such as interferon or Famvir.

In other embodiments, the CDK inhibitor or other inhibitor is administered in combination with a second therapeutic agent or a different therapeutic modality, e.g., an anti-cancer agent, and/or in combination with surgical and/or radiation procedures. In other embodiments, the CDK inhibitor is administered in combination with a second therapeutic agent or a different therapeutic modality, e.g., to treat a symptom of chemotherapy such as for treatment of nausea or headache.

By "in combination with," it is not intended to imply that the therapy or the therapeutic agents must be administered at the same time and/or formulated for delivery together, although these methods of delivery are within the scope of the invention. The pharmaceutical compositions can be administered concurrently with, prior to, or subsequent to, one or more other additional therapies or therapeutic agents. In general, each agent will be administered at a dose and/or on a time schedule determined for that agent. It will further be appreciated that the additional therapeutic agent utilized in this combination can be administered together in a single composition or administered separately in different compositions. The particular combination to employ in a regimen will take into account compatibility of the inventive pharmaceutical composition with the additional therapeutically active agent and/or the desired therapeutic effect to be achieved.

For example, the second therapeutic agent can be a cytotoxic or a cytostatic agent. Exemplary cytotoxic agents include antimicrotubule agents, topoisomerase inhibitors, or taxanes, antimetabolites, mitotic inhibitors, alkylating agents, intercalating agents, agents capable of interfering with a signal transduction pathway, agents that promote apoptosis and radiation. In yet other embodiments, the methods can be used in combination with immunodulatory agents, e.g., IL-1, 2, 4, 6, or 12, or interferon α or γ, or immune cell growth factors such as GM-CSF.

In certain embodiments, the CDK inhibitor, e.g., the CDK 4/6 inhibitor, is administered in combination with another agent, e.g., one or more anti-cancer agents. Exemplary anti-cancer agent combinations with the CDK include, but are not limited to, a PI3K inhibitor (e.g., a PI3K inhibitor as described herein and in, e.g., WO 2013/006532); an mTOR inhibitor (e.g., an mTOR inhibitor as described herein and in, e.g., WO 2011/130232); and a fibroblast growth factor receptor inhibitor, e.g., a pan-FGFR inhibitor or an FGFR3 inhibitor as described in, e.g., WO 2006/000420 and WO 2013/006368, incorporated herein by reference.

In some embodiments, the anti-cancer agent inhibits expression of a nucleic acid encoding a mutant gene, such as a mutant gene described herein. Examples of such antagonists include nucleic acid molecules, for example, antisense molecules, ribozymes, RNAi, triple helix molecules that hybridize to a nucleic acid encoding a cell cycle gene, or a transcription regulatory region, and block or reduce mRNA expression of a mutant cell cycle gene.

In some embodiments, the anti-cancer agent is a nucleic acid molecule, such as an antisense molecule, a ribozyme, an siRNA, or a triple helix molecule that hybridizes to a nucleic acid encoding a mutant gene, such as a mutant cell-cycle gene, or a transcription regulatory region, and blocks or reduces mRNA expression of the mutant gene.

An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire mutant gene coding strand, or to only a portion thereof. For example, the antisense nucleic acid can be complementary to the sequence in the ligand-binding domain that carries the mutation, e.g., can be complementary to the fusion junction in the ligand-binding domain created by the six-nucleotide deletion described herein. In another embodiment, the antisense nucleic acid molecule is antisense to a "noncoding region" of the coding strand of a nucleotide sequence encoding a mutant gene (e.g., the 5' and 3' untranslated regions). Anti-sense agents can include, for example, from about 8 to about 80 nucleobases (i.e. from about 8 to about 80 nucleotides), e.g., about 8 to about 50 nucleotides, or about 12 to about 30 nucleobases. Anti-sense compounds include ribozymes, external guide sequence (EGS) oligonucleotides (oligozymes), and other short catalytic RNAs or catalytic oligonucleotides which hybridize to the target nucleic acid and modulate its expression. Anti-sense compounds can include a stretch of at least eight consecutive nucleobases that are complementary to a sequence in the target gene. An oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA can interfere with one or more of the normal functions of mRNA. The functions of mRNA to be interfered with include all key functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

Exemplary antisense compounds include DNA or RNA sequences that specifically hybridize to the target nucleic acid, e.g., the mRNA encoding the mutant gene. The complementary region can extend for between about 8 to about 80 nucleobases. The compounds can include one or more modified nucleobases. Modified nucleobases are known in the art. Descriptions of modified nucleic acid agents are also available. See, e.g., U.S. Pat. Nos. 4,987,071; 5,116,742; and 5,093,246; Woolf et al. (1992) *Proc Natl Acad Sci USA; Antisense RNA and DNA*, D.A. Melton, Ed., Cold Spring Harbor Laboratory, Cold Spring Harbor, N.Y. (1988); 89:7305-9; Haselhoff and Gerlach (1988) *Nature* 334:585-59; Helene, C. (1991) *Anticancer Drug Des.* 6:569-84; Helene (1992) *Ann. N.Y. Acad. Sci.* 660:27-36; and Maher (1992) *Bioassays* 14:807-15.

siRNAs are small double stranded RNAs (dsRNAs) that optionally include overhangs. For example, the duplex region of an siRNA is about 18 to 25 nucleotides in length, e.g., about 19, 20, 21, 22, 23, or 24 nucleotides in length. Typically, the siRNA sequences are exactly complementary to the target mRNA. dsRNAs and siRNAs in particular can be used to silence gene expression in mammalian cells (e.g., human cells). siRNAs also include short hairpin RNAs (shRNAs) with 29-base-pair stems and 2-nucleotide 3' overhangs. See, e.g., Clemens et al. (2000) *Proc. Natl. Acad. Sci. USA* 97:6499-6503; Billy et al. (2001) *Proc. Natl. Sci. USA* 98:14428-14433; Elbashir et al. (2001) *Nature.* 411:494-8; Yang et al. (2002) *Proc. Natl. Acad. Sci. USA* 99:9942-9947; Siolas et al. (2005), *Nat. Biotechnol.* 23(2):227-31; 20040086884; U.S. 20030166282; 20030143204; 20040038278; and 20030224432.

A ribozyme having specificity for a mutant gene-encoding nucleic acid can include one or more sequences complementary to the nucleotide sequence of a mutant gene cDNA disclosed herein, and a sequence having known catalytic sequence responsible for mRNA cleavage (see U.S. Pat. No. 5,093,246 or Haselhoff and Gerlach (1988) *Nature* 334:585-591). For example, a derivative of a Tetrahymena L-19 IVS RNA can be constructed in which the nucleotide sequence of the active site is complementary to the nucleotide sequence to be cleaved in a mutant gene-encoding mRNA. See, e.g., Cech et al. U.S. Pat. No. 4,987,071; and Cech et al. U.S. Pat. No. 5,116,742. Alternatively, a mutant gene mRNA can be used to select a catalytic RNA having a specific ribonuclease activity from a pool of RNA molecules. See, e.g., Bartel, D. and Szostak, J. W. (1993) *Science* 261:1411-1418.

Mutant gene expression can also be inhibited by targeting nucleotide sequences complementary to the regulatory region of the mutant gene to form triple helical structures that prevent transcription of the mutant gene in target cells. See generally, Helene, C. (1991) *Anticancer Drug Des.* 6:569-84; Helene, C. i (1992) *Ann. N.Y. Acad. Sci.* 660:27-36; and Maher, L. J. (1992) *Bioassays* 14:807-15. The potential sequences that can be targeted for triple helix formation can be increased by creating a so-called "switchback" nucleic acid molecules. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

In some embodiments, an anti-cancer agent is a peptide nucleic acid (PNA). For example, PNAs can be used as antisense or antigene agents for sequence-specific modulation of gene expression by, for example, inducing transcription or translation arrest or inhibiting replication. PNAs of mutant nucleic acid molecules can also be used in the analysis of single base pair mutations in a gene (e.g., by PNA-directed PCR clamping); as 'artificial restriction enzymes' when used in combination with other enzymes (e.g., S1 nucleases (Hyrup B. et al. (1996) supra)).

In other embodiments, an anti-cancer agent that is a nucleic acid may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; WO88/09810) or the blood-brain barrier (see, e.g., WO 89/10134). In addition, oligonucleotides can be modified with hybridization-triggered cleavage agents (see, e.g., Krol et al. (1988) *Bio-Techniques* 6:958-976) or intercalating agents (See, e.g., Zon (1988) *Pharm. Res.* 5:539-549). To this end, the anti-cancer agent may be conjugated to another molecule, e.g., a peptide, hybridization triggered cross-linking agent, transport agent, or hybridization-triggered cleavage agent.

Methods for Detecting Viral and Mutant Nucleic Acids and Polypeptides

In another aspect, the invention features a method of determining the presence of an HPV nucleic acid, and/or a mutant gene, e.g., a mutant gene as described herein. In one embodiment, the HPV nucleic acid and/or the mutant gene (e.g., a mutant cell cycle gene) is identified by detection of an HPV nucleic acid molecule or polypeptide, and/or a mutant nucleic acid molecule or polypeptide. The method includes detecting whether a mutant nucleic acid molecule or polypeptide is present in a cell (e.g., a circulating cell), a tissue (e.g., a tumor), or a sample, e.g., a tumor sample, from a subject. In one embodiment, the sample is a nucleic acid sample. In one embodiment, the nucleic acid sample comprises DNA, e.g., genomic DNA or cDNA, or RNA, e.g., mRNA. In other embodiments, the sample is a protein sample.

In one embodiment, the sample is, or has been, classified as non-malignant using other diagnostic techniques, e.g., immunohistochemistry.

In one embodiment, the sample is, or has been, classified as malignant using other diagnostic techniques, e.g., immunohistochemistry.

In one embodiment, the sample is acquired from a subject (e.g., a subject, e.g., a patient, having or at risk of having a cancer, e.g., a patient), or alternatively, the method further includes acquiring a sample from the subject. The sample can be chosen from one or more of: tissue, e.g., cancerous tissue (e.g., a tissue biopsy), whole blood, serum, plasma, buccal scrape, sputum, saliva, cerebrospinal fluid, urine, stool, circulating tumor cells, circulating nucleic acids, or bone marrow. In certain embodiments, the sample is a tissue (e.g., a tumor biopsy), a circulating tumor cell or nucleic acid.

In embodiments, the tumor is from a cancer described herein, e.g., head and neck cancer, such as an HNSCC. In other embodiments, the cancer is a metastasis.

In one embodiment, the subject is at risk of having, or has a squamous cell carcinoma of the head and neck.

In other embodiments, the HPV and/or mutant gene is detected in a nucleic acid molecule by a method chosen from one or more of: nucleic acid hybridization assay, amplification-based assays (e.g., polymerase chain reaction (PCR)), PCR-RFLP assay, real-time PCR, sequencing, screening analysis (including metaphase cytogenetic analysis by standard karyotype methods, FISH (e.g., break away FISH), spectral karyotyping or MFISH, comparative genomic hybridization), in situ hybridization, SSP, HPLC or mass-spectrometric genotyping.

In one embodiment, the method includes: contacting a nucleic acid sample, e.g., a genomic DNA sample (e.g., a chromosomal sample or a fractionated, enriched or otherwise pre-treated sample) or a gene product (mRNA, cDNA), obtained from the subject, with a nucleic acid fragment (e.g., a probe or primer as described herein (e.g., an exon-specific probe or primer) under conditions suitable for hybridization, and determining the presence or absence of the mutant nucleic acid molecule. The method can, optionally, include enriching a sample for the gene or gene product.

In a related aspect, a method for determining the presence of an HPV and/or mutant nucleic acid molecule is provided.

The method includes: acquiring a sequence for a position in a nucleic acid molecule, e.g., by sequencing at least one nucleotide of the nucleic acid molecule (e.g., sequencing at least one nucleotide in the nucleic acid molecule that comprises the mutant gene), thereby determining that the mutant gene is present in the nucleic acid molecule. Optionally, the sequence acquired is compared to a reference sequence, or a wild type reference sequence. In one embodiment, the nucleic acid molecule is from a cell (e.g., a circulating cell), a tissue (e.g., a tumor), or any sample from a subject (e.g., blood or plasma sample). In other embodiments, the nucleic acid molecule from a tumor sample (e.g., a tumor or cancer sample) is sequenced. In one embodiment, the sequence is determined by a next generation sequencing method. The method further can further include acquiring, e.g., directly or indirectly acquiring, a sample, e.g., a tumor or cancer sample, from a subject (e.g., a patient). In certain embodiments, the cancer is an HNSCC.

In another aspect, the invention features a method of analyzing a tumor or a circulating tumor cell. The method includes acquiring a nucleic acid sample from the tumor or the circulating cell; and sequencing, e.g., by a next generation sequencing method, a nucleic acid molecule, e.g., a nucleic acid molecule that includes a mutant gene described herein. In one embodiment the invention features a method of analyzing a metastasis, e.g., in a tissue separate from the site of the primary tumor.

In one embodiment, probes or primers can be designed to detect a mutation in a cell cycle gene, such as a CDKN2A or CDKN2B or CCND1. In other embodiment, probes or primers can be design to detect an HPV strain.

In one embodiment, amplification-based assays can be used to measure the presence or absence of a gene, or copy number. In such amplification-based assays, the nucleic acid sequences act as a template in an amplification reaction (e.g., Polymerase Chain Reaction (PCR)). In a quantitative amplification, the amount of amplification product will be proportional to the amount of template in the original sample. Comparison to appropriate controls, e.g., healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that can be used to calibrate the PCR reaction. Detailed protocols for quantitative PCR are provided in Innis, et al. (1990) PCR Protocols, *A Guide to Methods and Applications,* Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR can also be used in the methods of the invention. In fluorogenic quantitative PCR, quantitation is based on amount of fluorescence signals, e.g., TaqMan® and SYBR® green.

In one embodiment, a TaqMan® assay is used to identify a mutation in a gene, e.g., a mutation as described herein, such as by utilizing a probe that binds specifically to the mutation, and a control probe that binds to the wildtype sequence, and probes that bind outside of the mutated sequence for PCR amplification.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Chromosomal probes are typically about 50 to about $10^5$ nucleotides in length. Longer probes typically comprise smaller fragments of about 100 to about 500 nucleotides in length. Probes that hybridize with centromeric DNA and locus-specific DNA are available commercially, for example, from Vysis, Inc. (Downers Grove, Ill.), Molecular Probes, Inc. (Eugene, Oreg.) or from Cytocell (Oxfordshire, UK). Alternatively, probes can be made non-commercially from chromosomal or genomic DNA through standard techniques. For example, sources of DNA that can be used include genomic DNA, cloned DNA sequences, somatic cell hybrids that contain one, or a part of one, chromosome (e.g., human chromsome) along with the normal chromosome complement of the host, and chromosomes purified by flow cytometry or microdis section. The region of interest can be isolated through cloning, or by site-specific amplification via the polymerase chain reaction (PCR). See, for example, Nath and Johnson, Biotechnic Histochem., 1998, 73(1):6-22, Wheeless et al., Cytometry 1994, 17:319-326, and U.S. Pat. No. 5,491,224.

Additional exemplary methods include, traditional "direct probe" methods such as Southern blots or in situ hybridization (e.g., fluorescence in situ hybridization (FISH) and FISH plus SKY), and "comparative probe" methods such as comparative genomic hybridization (CGH), e.g., cDNA-based or oligonucleotide-based CGH, can be used. The methods can be used in a wide variety of formats including, but not limited to, substrate (e.g., membrane or glass) bound methods or array-based approaches.

Additional protocols for FISH detection are described below.

The probes to be used hybridize to a specific region of a chromosome to determine whether a cytogenetic abnormality is present in this region. One type of cytogenetic abnormality is a deletion. Although deletions can be of one or more entire chromosomes, deletions normally involve loss of part of one or more chromosomes. If the entire region of a chromosome that is contained in a probe is deleted from a cell, hybridization of that probe to the DNA from the cell will normally not occur and no signal will be present on that chromosome. If the region of a chromosome that is partially contained within a probe is deleted from a cell, hybridization of that probe to the DNA from the cell can still occur, but less of a signal can be present. For example, the loss of a signal is compared to probe hybridization to DNA from control cells that do not contain the genetic abnormalities which the probes are intended to detect. In some embodiments, at least 1, 5, 10, 20, 30, 40, 50, 60, 70, 80, 90, 100, 110, 120, 130, 140, 150, 160, 170, 180, 190, 200, or more cells are enumerated for presence of the cytogenetic abnormality.

Cytogenetic abnormalities to be detected can include, but are not limited to, non-reciprocal translocations, intra-chromosomal inversions, point mutations, deletions, gene copy number changes, gene expression level changes, and germ line mutations. In particular, one type of cytogenetic abnormality is a duplication. Duplications can be of entire chromosomes, or of regions smaller than an entire chromosome. If the region of a chromosome that is contained in a probe is duplicated in a cell, hybridization of that probe to the DNA from the cell will normally produce at least one additional signal as compared to the number of signals present in control cells with no abnormality of the chromosomal region contained in the probe.

Chromosomal probes are labeled so that the chromosomal region to which they hybridize can be detected. Probes typically are directly labeled with a fluorophore, an organic molecule that fluoresces after absorbing light of lower wavelength/higher energy. The fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, U.S. Pat. No. 5,491,224.

U.S. Pat. No. 5,491,224 describes probe labeling as a number of the cytosine residues having a fluorescent label covalently bonded thereto. The number of fluorescently labeled cytosine bases is sufficient to generate a detectable fluorescent signal while the individual so labeled DNA segments essentially retain their specific complementary binding (hybridizing) properties with respect to the chromosome or chromosome region to be detected. Such probes are made by taking the unlabeled DNA probe segment, transaminating with a linking group a number of deoxycytidine nucleotides in the segment, covalently bonding a fluorescent label to at least a portion of the transaminated deoxycytidine bases.

Probes can also be labeled by nick translation, random primer labeling or PCR labeling. Labeling is done using either fluorescent (direct)-or haptene (indirect)-labeled nucleotides. Representative, non-limiting examples of labels include: AMCA-6-dUTP, CascadeBlue-4-dUTP, Fluorescein-12-dUTP, Rhodamine-6-dUTP, TexasRed-6-dUTP, Cy3-6-dUTP, Cy5-dUTP, Biotin(BIO)-11-dUTP, Digoxygenin(DIG)-11-dUTP or Dinitrophenyl (DNP)-11-dUTP.

Probes also can be indirectly labeled with biotin or digoxygenin, or labeled with radioactive isotopes such as $^{32}P$ and $^{3}H$, although secondary detection molecules or further processing then is required to visualize the probes. For example, a probe labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

Probes can also be prepared such that a fluorescent or other label is not part of the DNA before or during the hybridization, and is added after hybridization to detect the probe hybridized to a chromosome. For example, probes can be used that have antigenic molecules incorporated into the DNA. After hybridization, these antigenic molecules are detected using specific antibodies reactive with the antigenic molecules. Such antibodies can themselves incorporate a fluorochrome, or can be detected using a second antibody with a bound fluorochrome.

However treated or modified, the probe DNA is commonly purified in order to remove unreacted, residual products (e.g., fluorochrome molecules not incorporated into the DNA) before use in hybridization.

Prior to hybridization, chromosomal probes are denatured according to methods well known in the art. Probes can be hybridized or annealed to the chromosomal DNA under hybridizing conditions. "Hybridizing conditions" are conditions that facilitate annealing between a probe and target chromosomal DNA. Since annealing of different probes will vary depending on probe length, base concentration and the like, annealing is facilitated by varying probe concentration, hybridization temperature, salt concentration and other factors well known in the art.

Hybridization conditions are facilitated by varying the concentrations, base compositions, complexities, and lengths of the probes, as well as salt concentrations, temperatures, and length of incubation. For example, in situ hybridizations are typically performed in hybridization buffer containing 1× to 2×SSC, 50% to 65% formamide and blocking DNA to suppress non-specific hybridization. In general, hybridization conditions, as described above, include temperatures of about 25° C. to about 55° C., and incubation lengths of about 0.5 hours to about 96 hours.

Non-specific binding of chromosomal probes to DNA outside of the target region can be removed by a series of washes. Temperature and concentration of salt in each wash are varied to control stringency of the washes. For example, for high stringency conditions, washes can be carried out at about 65° C. to about 80° C., using 0.2× to about 2×SSC, and about 0.1% to about 1% of a non-ionic detergent such as Nonidet P-40 (NP40). Stringency can be lowered by decreasing the temperature of the washes or by increasing the concentration of salt in the washes. In some applications it is necessary to block the hybridization capacity of repetitive sequences. Thus, in some embodiments, tRNA, human genomic DNA, or Cot-I DNA is used to block non-specific hybridization. After washing, the slide is allowed to drain and air dry, then mounting medium, a counterstain such as DAPI, and a coverslip are applied to the slide. Slides can be viewed immediately or stored at −20° C. before examination.

For fluorescent probes used in fluorescence in situ hybridization (FISH) techniques, fluorescence can be viewed with a fluorescence microscope equipped with an appropriate filter for each fluorophore, or by using dual or triple bandpass filter sets to observe multiple fluorophores. See, for example, U.S. Pat. No. 5,776,688. Alternatively, techniques such as flow cytometry can be used to examine the hybridization pattern of the chromosomal probes.

In CGH methods, a first collection of nucleic acids (e.g., from a sample, e.g., a possible tumor) is labeled with a first label, while a second collection of nucleic acids (e.g., a control, e.g., from a healthy cell/tissue) is labeled with a second label. The ratio of hybridization of the nucleic acids is determined by the ratio of the two (first and second) labels binding to each fiber in the array. Where there are chromosomal deletions or multiplications, differences in the ratio of the signals from the two labels will be detected and the ratio will provide a measure of the copy number. Array-based CGH can also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays.

Hybridization protocols suitable for use with the methods of the invention are described, e.g., in Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology,* Vol. 33: In situ Hybridization Protocols, Choo, ed., Humana Press, Totowa, N.J. (1994), etc. In one embodiment, the hybridization protocol of Pinkel, et al. (1998) *Nature Genetics* 20: 207-211, or of Kallioniemi (1992) *Proc. Natl Acad Sci USA* 89:5321-5325 (1992) is used. Array-based CGH is described in U.S. Pat. No. 6,455,258, the contents of each of which are incorporated herein by reference.

In yet another embodiment, the level (e.g., expression level) or activity of the mutant gene is evaluated. For example, the level (e.g., expression level) or activity of the mutant gene (e.g., mRNA or polypeptide) is detected and (optionally) compared to a pre-determined value, e.g., a reference value (e.g., a control sample).

In yet other embodiments, a viral or mutant polypeptide is detected. The method includes: contacting a protein sample with a reagent which specifically binds to a viral polypeptide or mutant polypeptide; and detecting the formation of a complex of the polypeptide and the reagent. In one embodiment, the reagent is labeled with a detectable group to facilitate detection of the bound and unbound reagent. In one embodiment, the reagent is an antibody molecule, e.g., is selected from the group consisting of an antibody, and antibody derivative, and an antibody fragment.

The activity or level of a viral polypeptide or mutant polypeptide can also be detected and/or quantified by detecting or quantifying the expressed polypeptide. The polypeptide can be detected and quantified by any of a number of means known to those of skill in the art. These can include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, immunohistochemistry (IHC) and the like. A skilled artisan can adapt known protein/antibody detection methods.

Another agent for detecting a viral polypeptide or mutant polypeptide is an antibody molecule capable of binding to the polypeptide, e.g., an antibody with a detectable label. Techniques for generating antibodies are described herein. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

In another embodiment, the antibody is labeled, e.g., a radio-labeled, chromophore-labeled, fluorophore-labeled, or enzyme-labeled antibody. In another embodiment, an antibody derivative (e.g., an antibody conjugated with a substrate or with the protein or ligand of a protein-ligand pair (e.g., biotin-streptavidin)), or an antibody fragment (e.g., a single-chain antibody, an isolated antibody hypervariable domain, etc.) which binds specifically with a mutant protein, is used.

Mutant polypeptides from cells can be isolated using techniques that are known to those of skill in the art. The protein isolation methods employed can, for example, be such as those described in Harlow and Lane (Harlow and Lane, 1988, *Antibodies: A Laboratory Manual*, Cold Spring Harbor Laboratory Press, Cold Spring Harbor, N.Y.).

Means of detecting proteins using electrophoretic techniques are well known to those of skill in the art (see generally, R. Scopes (1982) *Protein Purification*, Springer-Verlag, N.Y.; Deutscher, (1990) *Methods in Enzymology* Vol. 182: *Guide to Protein Purification*, Academic Press, Inc., N.Y.).

In another embodiment, Western blot (immunoblot) analysis is used to detect and quantify the presence of a polypeptide in the sample.

In another embodiment, the polypeptide is detected using an immunoassay. As used herein, an immunoassay is an assay that utilizes an antibody to specifically bind to the analyte. The immunoassay is thus characterized by detection of specific binding of a polypeptide to an anti-antibody as opposed to the use of other physical or chemical properties to isolate, target, and quantify the analyte.

The mutant polypeptide is detected and/or quantified using any of a number of immunological binding assays (see, e.g., U.S. Pat. Nos. 4,366,241; 4,376,110; 4,517,288; and 4,837,168). For a review of the general immunoassays, see also Asai (1993) *Methods in Cell Biology* Volume 37: *Antibodies in Cell Biology*, Academic Press, Inc. New York; Stites & Terr (1991) *Basic and Clinical Immunology* 7th Edition.

HPV Molecule and/or Mutant Gene Expression Level

In certain embodiments, HPV molecule and/or mutant gene expression levels (e.g., mutant cell cycle gene expression levels) can also be assayed. Gene expression can be assessed by any of a wide variety of methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In certain embodiments, activity of a particular gene is characterized by a measure of gene transcript (e.g., mRNA), by a measure of the quantity of translated protein, or by a measure of gene product activity. Mutant gene expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

Methods of detecting and/or quantifying the HPV molecule and/or mutant gene transcript (mRNA or cDNA made therefrom) using nucleic acid hybridization techniques are known to those of skill in the art (see Sambrook et al. supra). For example, one method for evaluating the presence, absence, or quantity of cDNA involves a Southern transfer as described above. Briefly, the mRNA is isolated (e.g., using an acid guanidinium-phenol-chloroform extraction method, Sambrook et al. supra.) and reverse transcribed to produce cDNA. The cDNA is then optionally digested and run on a gel in buffer and transferred to membranes. Hybridization is then carried out using the nucleic acid probes specific for the mutant cDNA, e.g., using the probes and primers described herein.

In other embodiments, HPV molecule and/or mutant gene expression is assessed by preparing genomic DNA or mRNA/cDNA (i.e., a transcribed polynucleotide) from cells in a subject sample, and by hybridizing the genomic DNA or mRNA/cDNA with a reference polynucleotide which is a complement of a polynucleotide comprising the mutant gene, and fragments thereof. cDNA can, optionally, be amplified using any of a variety of polymerase chain reaction methods prior to hybridization with the reference polynucleotide. Expression of a mutant gene can likewise be detected using quantitative PCR (QPCR) to assess the level of mutant gene expression.

Detection of HPV and/or Mutant Polypeptides

In another aspect, the invention features a mutant polypeptide (e.g., a purified mutant polypeptide), a biologically active or antigenic fragment thereof, as well as reagents (e.g., antibody molecules that bind to a mutant polypeptide), methods for modulating a mutant polypeptide activity and detection of a mutant polypeptide, e.g., a mutant cell-cycle polypeptide.

In one embodiment, the mutant polypeptide has at least one biological activity, e.g., a role in cell-cycle regulation. In one embodiment, at least one biological activity of a mutant polypeptide is reduced or inhibited by an anti-cancer agent, e.g., cell cycle inhibitor, such as a CDK inhibitor, such as an inhibitor of one or both of CDK4 or CDK6.

In other embodiments, the mutant polypeptide includes a fragment of a mutant polypeptide containing a mutation described herein.

In yet other embodiments, the mutant polypeptide is encoded by a nucleic acid molecule described herein.

In another embodiment, the mutant polypeptide or fragment thereof is a peptide, e.g., an immunogenic peptide or protein that contains a mutation described herein. Such immunogenic peptides or proteins can be used to raise antibodies specific to the mutant protein. In other embodiments, such immunogenic peptides or proteins can be used for vaccine preparation. The vaccine preparation can include other components, e.g., an adjuvant.

In another aspect, the invention features antibody molecules that bind to a mutant polypeptide or fragment described herein. In embodiments the antibody can distinguish a wild-type from a mutant polypeptide.

In one aspect, the invention features a polypeptide comprising a mutation identified in Table 1.

Kits

In one aspect, the invention features, a kit, e.g., containing methods for determining whether a subject is HPV+ or HPV−, and to accordingly identify an appropriate therapeutic agent to treat the a cancer, e.g., a HNSCC, in the subject. For example, in some embodiments the kit contains primers, such as for PCR, or one or more probes for detecting an HPV in a sample from the subject. In other embodiment, the kit contains an antibody for detecting an HPV protein in a sample from the subject.

Optionally, the kit also contains an oligonucleotide having a mutation described herein, e.g., an oligonucleiotide that hybridizes specifically to a mutation in a functional domain of a mutant gene, such as a mutant cell cycle gene. Optionally, the kit can also contain an oligonucleotide that is the wildtype counterpart of the mutant oligonucleotide.

A kit featured in the invention can include a carrier, e.g., a means being compartmentalized to receive in close confinement one or more container means. In one embodiment the container contains an oligonucleotide, e.g., a primer or probe as described above. The components of the kit are useful, for example, to identify a mutation in a tumor sample in a patient. The probe or primer of the kit can be used in any sequencing or nucleotide detection assay known in the art, e.g., a sequencing assay, e.g., an NGS method, RT-PCR, or in situ hybridization.

A kit featured in the invention can include, e.g., assay positive and negative controls, nucleotides, enzymes (e.g., RNA or DNA polymerase or ligase), solvents or buffers, a stabilizer, a preservative, a secondary antibody, e.g., an anti-HRP antibody (IgG) and a detection reagent.

An oligonucleotide can be provided in any form, e.g., liquid, dried, semi-dried, or lyophilized, or in a form for storage in a frozen condition.

Typically, an oligonucleotide, and other components in a kit are provided in a form that is sterile. When an oligonucleotide, e.g., an oligonucleotide that contains a mutation in a gene, e.g., a mutation in a functional domain of a gene as described herein, or an oligonucleotide complementary to a mutation, is provided in a liquid solution, the liquid solution generally is an aqueous solution, e.g., a sterile aqueous solution. When the oligonucleotide is provided as a dried form, reconstitution generally is accomplished by the addition of a suitable solvent. The solvent, e.g., sterile buffer, can optionally be provided in the kit.

The kit can include one or more containers for the composition containing an oligonucleotide in a concentration suitable for use in the assay or with instructions for dilution for use in the assay. In some embodiments, the kit contains separate containers, dividers or compartments for the oligonucleotide and assay components, and the informational material. For example, the oligonucleotides can be contained in a bottle or vial, and the informational material can be contained in a plastic sleeve or packet. In other embodiments, the separate elements of the kit are contained within a single, undivided container. For example, an oligonucleotide composition is contained in a bottle or vial that has attached thereto the informational material in the form of a label. In some embodiments, the kit includes a plurality (e.g., a pack) of individual containers, each containing one or more unit forms (e.g., for use with one assay) of an oligonucleotide. For example, the kit includes a plurality of ampoules, foil packets, or blister packs, each containing a single unit of oligonucleotide for use in a sequencing or detecting a mutation in a tumor sample. The containers of the kits can be air tight and/or waterproof. The container can be labeled for use.

For antibody-based kits, the kit can include: (1) a first antibody (e.g., attached to a solid support) which binds specifically to an HPV protein, or a mutant polypeptide associated with the HNSCC, such as a polypeptide that functions in the cell cycle; and, optionally, (2) a second, different antibody which binds to either the polypeptide or the first antibody and is conjugated to a detectable agent.

In one embodiment, the kit can include informational material for performing and interpreting the sequencing or diagnostic. In another embodiment, the kit can provide guidance as to where to report the results of the assay, e.g., to a treatment center or healthcare provider. The kit can include forms for reporting the results of a sequencing or diagnostic assay described herein, and address and contact information regarding where to send such forms or other related information; or a URL (Uniform Resource Locator) address for reporting the results in an online database or an online application (e.g., an app). In another embodiment, the informational material can include guidance regarding whether a patient should receive treatment with a particular chemotherapeutic drug, depending on the results of the assay.

The informational material of the kits is not limited in its form. In many cases, the informational material, e.g., instructions, is provided in printed matter, e.g., a printed text, drawings, and/or photographs, e.g., a label or printed sheet. However, the informational material can also be provided in other formats, such as computer readable material, video recording, or audio recording. In another embodiment, the informational material of the kit is contact information, e.g., a physical address, email address, website, or telephone number, where a user of the kit can obtain substantive information about the sequencing or diagnostic assay and/or its use in the methods described herein. The informational material can also be provided in any combination of formats.

In some embodiments, a biological sample is provided to an assay provider, e.g., a service provider (such as a third party facility) or a healthcare provider, who evaluates the sample in an assay and provides a read out. For example, in one embodiment, an assay provider receives a biological sample from a subject, such as a blood or tissue sample, e.g., a biopsy sample, and evaluates the sample using an assay described herein, e.g., a sequencing assay or in situ hybridization assay, and determines that the sample contains a nucleic acid containing a mutation described in Table 1. The assay provider, e.g., a service provider or healthcare provider, can then conclude that the subject is, or is not, a candidate for a particular drug or a particular cancer treatment regimen.

The assay provider can provide the results of the evaluation, and optionally, conclusions regarding one or more of diagnosis, prognosis, or appropriate therapy options to, for example, a healthcare provider, or patient, or an insurance company, in any suitable format, such as by mail or electronically, or through an online database. The information collected and provided by the assay provider can be stored in a database.

The invention is further illustrated by the following example, which should not be construed as further limiting.

Systems or Devices

In another aspect, the invention features a system or a device (e.g., a sequencing device) for producing a report, e.g., a report for recording the presence or absence of HPV in a patient. The system or device can include a component for containing a sample (e.g., a blood or serum sample, or tumor sample from a patient); a detection component capable of identifying the presence or absence of a HPV, e.g., a sequence of an HPV gene or gene fragment as described herein; and a means for outputting a report, e.g., a report as described herein. For example, the detection component can include a probe or primer for detecting a sequence of an HPV, such as by a sequencing method, such as by PCR.

In another aspect, the invention features a system or a device (e.g., a sequencing device) for producing a report, e.g., a genotype report. The system or device can include a component for containing a sample (e.g., a tumor nucleic acid or polypeptide); a detection component capable of identifying the presence or absence of a mutant gene, e.g., a mutant cell cycle gene as described herein; and a means for outputting a report, e.g., a report as described herein.

In one embodiment, the component for containing a tumor sample is configured in a way to contain or hold the sample, e.g., a tumor nucleic acid or polypeptide sample.

In another embodiment, the detection component produces and/or analyzes a signal according to the presence or absence of the mutant gene in the sample.

In another embodiment, the means for outputting a report provides a system for annotating the association of the detected mutant gene to the sample. The report can include, e.g., the identification of nucleotide values, the indication of presence or absence of a mutant gene as described herein, or sequence, and whether the sample was obtained from an HPV+ or HPV− patient. In one embodiment, a report is generated, such as in paper or electronic form, which identifies the presence or absence of an alteration described herein, and optionally includes an identifier for the patient from which the sequence was obtained.

The report can also include information on the role of a sequence, e.g., a mutant cell cycle gene as described herein, or wild-type sequence, in disease. Such information can include information on prognosis, resistance, or potential or suggested therapeutic options. The report can include information on the likely effectiveness of a therapeutic option, the acceptability of a therapeutic option, or the advisability of applying the therapeutic option to a patient, e.g., a patient having a sequence, alteration or mutation identified in the test, and in embodiments, identified in the report.

Nucleic Acid Detection and Capturing Reagents

The invention also features a nucleic acid molecule, e.g., nucleic acid fragment, suitable as probe, primer, bait or library member that includes, flanks, hybridizes to, and which are useful for identifying, or are otherwise based on, the mutants described herein. In certain embodiments, the probe, primer or bait molecule is an oligonucleotide that allows capture, detection or isolation of a mutant nucleic acid molecule, e.g., a mutant cell cycle gene or gene of the PI3K gene described herein.

In one embodiment, the nucleic acid fragment is a probe or primer that includes an oligonucleotide between about 5 and 25, e.g., between 10 and 20, or 10 and 15 nucleotides in length. In other embodiments, the nucleic acid fragment is a bait that includes an oligonucleotide between about 100 to 300 nucleotides, 130 and 230 nucleotides, or 150 and 200 nucleotides, in length.

In one embodiment, the nucleic acid fragment can be used to identify or capture, e.g., by hybridization, a mutant cell cycle gene. For example, the nucleic acid fragment can be a probe, a primer, or a bait, for use in identifying or capturing, e.g., by hybridization, a mutant cell cycle gene described herein.

The probes or primers described herein can be used, for example, for FISH detection or PCR amplification. In one exemplary embodiment where detection is based on PCR, amplification of an cell cycle gene mutation, can be performed using a primer or a primer pair, e.g., for amplifying a mutant sequence described herein. In one embodiment, a pair of isolated oligonucleotide primers can amplify a region containing or adjacent to an mutation.

In another embodiment, the nucleic acid fragments can be used to identify, e.g., by hybridization, a mutant gene.

In other embodiments, the nucleic acid fragment includes a bait that comprises a nucleotide sequence that hybridizes to a mutant nucleic acid molecule described herein, and thereby allows the capture or isolation of said nucleic acid molecule. In one embodiment, a bait is suitable for solution phase hybridization. In other embodiments, a bait includes a binding entity, e.g., an affinity tag, that allows capture and separation, e.g., by binding to a binding entity, of a hybrid formed by a bait and a nucleic acid hybridized to the bait.

In other embodiments, the nucleic acid fragment includes a library member comprising a mutant nucleic acid molecule described herein.

The nucleic acid fragment can be detectably labeled with, e.g., a radiolabel, a fluorescent label, a bioluminescent label, a chemiluminescent label, an enzyme label, a binding pair label, or can include an affinity tag; a tag, or identifier (e.g., an adaptor, barcode or other sequence identifier).

One aspect of the invention pertains to isolated nucleic acid molecules that include a mutation, including nucleic acids which encode a polypeptide that contains a mutation in a structural domain, or a portion of such a polypeptide. The nucleic acid can include a cell cycle gene, such as a CDKN2A, CDKN2B or CCND1 gene. The nucleic acid molecules include those nucleic acid molecules which reside in genomic regions identified herein. As used herein, the term "nucleic acid molecule" includes DNA molecules (e.g., cDNA or genomic DNA) and RNA molecules (e.g., mRNA) and analogs of the DNA or RNA generated using nucleotide analogs. The nucleic acid molecule can be single-stranded or double-stranded; in certain embodiments the nucleic acid molecule is double-stranded DNA.

Isolated nucleic acid molecules also include nucleic acid molecules sufficient for use as hybridization probes or primers to identify nucleic acid molecules that contain a mutation in a gene, e.g., a cell cycle gene, e.g., nucleic acid molecules suitable for use as PCR primers for the amplification or mutation of nucleic acid molecules.

An "isolated" nucleic acid molecule is one which is separated from other nucleic acid molecules which are present in the natural source of the nucleic acid molecule. In certain embodiments, an "isolated" nucleic acid molecule is free of sequences (such as protein-encoding sequences) which naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

The language "substantially free of other cellular material or culture medium" includes preparations of nucleic acid molecule in which the molecule is separated from cellular components of the cells from which it is isolated or recombinantly produced. Thus, nucleic acid molecule that is substantially free of cellular material includes preparations of nucleic acid molecule having less than about 30%, less than about 20%, less than about 10%, or less than about 5% (by dry weight) of other cellular material or culture medium.

A nucleic acid molecule containing a mutation in a cell cycle gene can be isolated using standard molecular biology techniques and the sequence information in the database records described herein. Using all or a portion of such nucleic acid sequences, mutant nucleic acid molecules can be isolated using standard hybridization and cloning techniques (e.g., as described in Sambrook et al., ed., *Molecular Cloning: A Laboratory Manual*, 2nd ed., Cold Spring Harbor Laboratory Press, Cold Spring Harbor, N.Y., 1989).

Probes based on the sequence of a mutant nucleic acid molecule can be used to detect transcripts or genomic sequences corresponding to one or more markers featured in the invention. The probe comprises a label group attached thereto, e.g., a radioisotope, a fluorescent compound, an enzyme, or an enzyme co-factor. Such probes can be used as part of a test kit for identifying cells or tissues which express a mutant protein, such as by measuring levels of a nucleic acid molecule encoding the protein in a sample of cells from a subject, e.g., detecting mRNA levels or determining whether a gene encoding the protein has been mutated or deleted.

Probes featured in the invention include those that will specifically hybridize to a gene sequence described in the Table 1, e.g., a cell cycle gene, such as CDKN2A or CDKN2B, or CCND1. In some embodiments, probes featured in the invention will specifically hybridize to a gene rearrangement described in Table 4. Typically these probes are 12 to 20, e.g., 17 to 20 nucleotides in length (longer for large insertions) and have the nucleotide sequence corresponding to the region of the mutations at their respective nucleotide locations on the gene sequence. Such molecules can be labeled according to any technique known in the art, such as with radiolabels, fluorescent labels, enzymatic labels, sequence tags, biotin, other ligands, etc. As used herein, a probe that "specifically hybridizes" to a mutant gene sequence will hybridize under high stringency conditions.

A probe will typically contain one or more of the specific mutations described herein. Typically, a nucleic acid probe will encompass only one mutation. Such molecules may be labeled and can be used as allele-specific probes to detect the mutation of interest.

The term "primer" as used herein refers to a sequence comprising two or more deoxyribonucleotides or ribonucleotides, e.g., more than three, and more than eight, or at least 20 nucleotides of a gene described in Table 1 or Table 4, where the sequence corresponds to a sequence flanking one of the mutations or a wildtype sequence of a gene identified in Table 1 or Table 4, e.g., a CDKN2A or CDKN2B gene or a CCND1 gene. Primers may be used to initiate DNA synthesis via the PCR (polymerase chain reaction) or a sequencing method. Primers featured in the invention include the sequences recited and complementary sequences which would anneal to the opposite DNA strand of the sample target. Since both strands of DNA are complementary and mirror images of each other, the same segment of DNA will be amplified.

Primers can be used to sequence a nucleic acid, e.g., an isolated nucleic acid described herein, such as by an NGS method, or to amplify a gene described in Table 1 or Table 4, such as by PCR. The primers can specifically hybridize, for example, to the ends of the exons or to the introns flanking the exons. The amplified segment can then be further analyzed for the presence of the mutation such as by a sequencing method, or by a size separation technique such as by electrophoresis on a gel. The primers are useful in directing amplification of a target polynucleotide prior to sequencing. Such primers are useful in directing amplification of a target region that includes a mutation, e.g., prior to sequencing. The primer typically contains 12 to 20, or 17 to 20, or more nucleotides, although a primer may contain fewer nucleotides.

A primer is typically single stranded, e.g., for use in sequencing or amplification methods, but may be double stranded. If double stranded, the primer may first be treated to separate its strands before being used to prepare extension products. A primer must be sufficiently long to prime the synthesis of extension products in the presence of the inducing agent for polymerization. The exact length of primer will depend on many factors, including applications (e.g., amplification method), temperature, buffer, and nucleotide composition. A primer typically contains 12-20 or more nucleotides, although a primer may contain fewer nucleotides.

Primers are typically designed to be "substantially" complementary to each strand of a genomic locus to be amplified. Thus, the primers must be sufficiently complementary to specifically hybridize with their respective strands under conditions which allow the agent for polymerization to perform. In other words, the primers should have sufficient complementarity with the 5' and 3' sequences flanking the mutation to hybridize therewith and permit amplification of the genomic locus.

The term "substantially complementary to" or "substantially the sequence" refers to sequences that hybridize to the sequences provided under stringent conditions and/or sequences having sufficient homology with a sequence comprising a mutation, e.g., a point mutation or fusion junction, or the wildtype counterpart sequence, such that the allele specific oligonucleotides hybridize to the sequence. In one embodiment, a sequence is substantially complementary to a fusion junction created by a deletion event or a translocation. "Substantially the same" as it refers to oligonucleotide sequences also refers to the functional ability to hybridize or anneal with sufficient specificity to distinguish between the presence or absence of the mutation. This is measurable by the temperature of melting being sufficiently different to permit easy identification of whether the oligonucleotide is binding to the normal or mutant gene sequence identified in the Example.

In one aspect, the invention features a primer or primer set for amplifying a nucleic acid comprising a mutation in a cell cycle gene.

Nucleic Acid Samples

A variety of tissue samples can be the source of the nucleic acid samples used in the present methods, e.g., the source of the nucleic acid sample to assay for the presence of an HPV nucleic acid or a mutation in a gene described herein, such as a gene or gene alteration described in Table 1 or Table 4. Genomic or subgenomic DNA fragments can be isolated from a subject's sample (e.g., a tumor sample, a normal adjacent tissue (NAT), a blood sample or any normal control)). In certain embodiments, the tissue sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample. The isolating step can include flow-sorting of individual chromosomes; and/or micro-dissecting a subject's sample (e.g., a tumor sample, a NAT, a blood sample).

Protocols for DNA isolation from a tissue sample are known in the art. Additional methods to isolate nucleic acids (e.g., DNA) from formaldehyde- or paraformaldehyde-fixed, paraffin-embedded (FFPE) tissues are disclosed, e.g., in Cronin M. et al., (2004) *Am J Pathol.* 164(1):35-42; Masuda N. et al., (1999) *Nucleic Acids Res.* 27(22):4436-4443; Specht K. et al., (2001) *Am J Pathol.* 158(2):419-429, Ambion RecoverAll™ Total Nucleic Acid Isolation Protocol (Ambion, Cat. No. AM1975, September 2008), and QIAamp® DNA FFPE Tissue Handbook (Qiagen, Cat. No. 37625, October 2007). RecoverAll™ Total Nucleic Acid Isolation Kit uses xylene at elevated temperatures to solubilize paraffin-embedded samples and a glass-fiber filter to capture nucleic acids. QIAamp® DNA FFPE Tissue Kit uses QIAamp® DNA Micro technology for purification of genomic and mitochondrial DNA.

The isolated nucleic acid samples (e.g., genomic DNA samples) can be fragmented or sheared by practicing routine techniques. For example, genomic DNA can be fragmented by physical shearing methods, enzymatic cleavage methods, chemical cleavage methods, and other methods well known to those skilled in the art. The nucleic acid library can contain all or substantially all of the complexity of the genome. The term "substantially all" in this context refers to the possibility that there can in practice be some unwanted loss of genome complexity during the initial steps of the procedure. The methods described herein also are useful in cases where the nucleic acid library is a portion of the genome, i.e., where the complexity of the genome is reduced by design. In some embodiments, any selected portion of the genome can be used with the methods described herein. In certain embodiments, the entire exome or a subset thereof is isolated.

Methods can further include isolating a nucleic acid sample to provide a library (e.g., a nucleic acid library). In certain embodiments, the nucleic acid sample includes whole genomic, subgenomic fragments, or both. The isolated nucleic acid samples can be used to prepare nucleic acid libraries. Thus, in one embodiment, the methods featured in the invention further include isolating a nucleic acid sample to provide a library (e.g., a nucleic acid library as described herein). Protocols for isolating and preparing libraries from whole genomic or subgenomic fragments are known in the art (e.g., Illumina's genomic DNA sample preparation kit). In certain embodiments, the genomic or subgenomic DNA fragment is isolated from a subject's sample (e.g., a tumor sample, a normal adjacent tissue (NAT), a blood sample or any normal control)). In one embodiment, the sample (e.g., the tumor or NAT sample) is a preserved. For example, the sample is embedded in a matrix, e.g., an FFPE block or a frozen sample. In certain embodiments, the isolating step includes flow-sorting of individual chromosomes; and/or microdissecting a subject's sample (e.g., a tumor sample, a NAT, a blood sample). In certain embodiments, the nucleic acid sample used to generate the nucleic acid library is less than 5, less than 1 microgram, less than 500 ng, less than 200 ng, less than 100 ng, less than 50 ng or less than 20 ng (e.g., 10 ng or less).

In still other embodiments, the nucleic acid sample used to generate the library includes RNA or cDNA derived from RNA. In some embodiments, the RNA includes total cellular RNA. In other embodiments, certain abundant RNA sequences (e.g., ribosomal RNAs) have been depleted. In some embodiments, the poly(A)-tailed mRNA fraction in the total RNA preparation has been enriched. In some embodiments, the cDNA is produced by random-primed cDNA synthesis methods. In other embodiments, the cDNA synthesis is initiated at the poly(A) tail of mature mRNAs by priming by oligo(dT)-containing oligonucleotides. Methods for depletion, poly(A) enrichment, and cDNA synthesis are well known to those skilled in the art.

The method can further include amplifying the nucleic acid sample (e.g., DNA or RNA sample) by specific or non-specific nucleic acid amplification methods that are well known to those skilled in the art. In some embodiments, certain embodiments, the nucleic acid sample is amplified, e.g., by whole-genome amplification methods such as random-primed strand-displacement amplification.

In other embodiments, the nucleic acid sample is fragmented or sheared by physical or enzymatic methods and ligated to synthetic adapters, size-selected (e.g., by preparative gel electrophoresis) and amplified (e.g., by PCR). In other embodiments, the fragmented and adapter-ligated group of nucleic acids is used without explicit size selection or amplification prior to hybrid selection.

In other embodiments, the isolated DNA (e.g., the genomic DNA) is fragmented or sheared. In some embodiments, the library includes less than 50% of genomic DNA, such as a subfraction of genomic DNA that is a reduced representation or a defined portion of a genome, e.g., that has been subfractionated by other means. In other embodiments, the library includes all or substantially all genomic DNA.

In some embodiments, the library includes less than 50% of genomic DNA, such as a subfraction of genomic DNA that is a reduced representation or a defined portion of a genome, e.g., that has been subfractionated by other means. In other embodiments, the library includes all or substantially all genomic DNA. Protocols for isolating and preparing libraries from whole genomic or subgenomic fragments are known in the art (e.g., Illumina's genomic DNA sample preparation kit). Alternative DNA shearing methods can be more automatable and/or more efficient (e.g., with degraded FFPE samples). Alternatives to DNA shearing methods can also be used to avoid a ligation step during library preparation.

The methods described herein can be performed using a small amount of nucleic acids, e.g., when the amount of source DNA is limiting (e.g., even after whole-genome amplification). In one embodiment, the nucleic acid comprises less than about 5 µg, 4 µg, 3 µg, 2 µg, 1 µg, 0.8 µg, 0.7 µg, 0.6 µg, 0.5 µg, or 400 ng, 300 ng, 200 ng, 100 ng, 50 ng, or 20 ng or less of nucleic acid sample. For example, to prepare 500 ng of hybridization-ready nucleic acids, one typically begins with 3 µg of genomic DNA. One can start with less, however, if one amplifies the genomic DNA (e.g., using PCR) before the step of solution hybridization. Thus it is possible, but not essential, to amplify the genomic DNA before solution hybridization.

In some embodiments, a library is generated using DNA (e.g., genomic DNA) from a sample tissue, and a corresponding library is generated with RNA (or cDNA) isolated from the same sample tissue.

Design of Baits

A bait can be a nucleic acid molecule, e.g., a DNA or RNA molecule, which can hybridize to (e.g., be complementary to), and thereby allow capture of a target nucleic acid. In one embodiment, a bait is an RNA molecule. In other embodiments, a bait includes a binding entity, e.g., an affinity tag, that allows capture and separation, e.g., by binding to a binding entity, of a hybrid formed by a bait and a nucleic acid hybridized to the bait. In one embodiment, a bait is suitable for solution phase hybridization.

Baits can be produced and used by methods and hybridization conditions as described in US 2010/0029498 and Gnirke, A. et al. (2009) *Nat Biotechnol.* 27(2):182-189, and PCT/US 11/67725, filed Dec. 29, 2011, incorporated herein by reference. For example, biotinylated RNA baits can be produced by obtaining a pool of synthetic long oligonucleotides, originally synthesized on a microarray, and amplifying the oligonucleotides to produce the bait sequences. In some embodiments, the baits are produced by adding an RNA polymerase promoter sequence at one end of the bait sequences, and synthesizing RNA sequences using RNA polymerase. In one embodiment, libraries of synthetic oligodeoxynucleotides can be obtained from commercial suppliers, such as Agilent Technologies, Inc., and amplified using known nucleic acid amplification methods.

Each bait sequence can include a target-specific (e.g., a member-specific) bait sequence and universal tails on each end. As used herein, the term "bait sequence" can refer to the target-specific bait sequence or the entire oligonucleotide including the target-specific "bait sequence" and other nucleotides of the oligonucleotide. In one embodiment, a target-specific bait hybridizes to a nucleic acid sequence comprising a nucleic acid sequence in certain exons of a gene, e.g., a cell cycle gene.

In one embodiment, the bait is an oligonucleotide about 200 nucleotides in length, of which 170 nucleotides are target-specific "bait sequence." The other 30 nucleotides (e.g., 15 nucleotides on each end) are universal arbitrary tails used for PCR amplification. The tails can be any sequence selected by the user. For example, the pool of synthetic oligonucleotides can include oligonucleotides of the sequence of 5'-ATCGCACCAGCGTGTN$_{170}$CACTGCGGCTCCTCA-3' (SEQ ID NO:1) with N$_{170}$ indicating the target-specific bait sequences.

The bait sequences described herein can be used for selection of exons and short target sequences. In one embodiment, the bait is between about 100 nucleotides and 300 nucleotides in length. In another embodiment, the bait is between about 130 nucleotides and 230 nucleotides in length. In yet another embodiment, the bait is between about 150 nucleotides and 200 nucleotides in length. The target-specific sequences in the baits, e.g., for selection of exons and short target sequences, are between about 40 nucleotides and 1000 nucleotides in length. In one embodiment, the target-specific sequence is between about 70 nucleotides and 300 nucleotides in length. In another embodiment, the target-specific sequence is between about 100 nucleotides and 200 nucleotides in length. In yet another embodiment, the target-specific sequence is between about 120 nucleotides and 170 nucleotides in length.

Sequencing

The invention also includes methods of sequencing nucleic acids. In one embodiment, any of a variety of sequencing reactions known in the art can be used to directly sequence at least a portion of a mutant gene. In one embodiment, the mutant gene sequence is compared to a corresponding reference (control) sequence.

In one embodiment, the sequence of the mutant nucleic acid molecule is determined by a method that includes one or more of: hybridizing an oligonucleotide, e.g., an allele specific oligonucleotide for one alteration described herein to said nucleic acid; hybridizing a primer, or a primer set (e.g., a primer pair), that amplifies a region comprising the mutation or a fusion junction of the allele; amplifying, e.g., specifically amplifying, a region comprising the mutation or a fusion junction of the allele; attaching an adapter oligonucleotide to one end of a nucleic acid that comprises the mutation or a fusion junction of the allele; generating an optical, e.g., a colorimetric signal, specific to the presence of the one of the mutation or fusion junction; hybridizing a nucleic acid comprising the mutation or fusion junction to a second nucleic acid, e.g., a second nucleic acid attached to a substrate; generating a signal, e.g., an electrical or fluorescent signal, specific to the presence of the mutation or fusion junction; and incorporating a nucleotide into an oligonucleotide that is hybridized to a nucleic acid that contains the mutation or fusion junction.

In another embodiment, the sequence is determined by a method that comprises one or more of: determining the nucleotide sequence from an individual nucleic acid molecule, e.g., where a signal corresponding to the sequence is derived from a single molecule as opposed, e.g., from a sum of signals from a plurality of clonally expanded molecules; determining the nucleotide sequence of clonally expanded proxies for individual nucleic acid molecules; massively parallel short-read sequencing; template-based sequencing; pyrosequencing; real-time sequencing comprising imaging the continuous incorporation of dye-labeling nucleotides during DNA synthesis; nanopore sequencing; sequencing by hybridization; nano-transistor array based sequencing; polony sequencing; scanning tunneling microscopy (STM) based sequencing; or nanowire-molecule sensor based sequencing.

Any method of sequencing known in the art can be used. Exemplary sequencing reactions include those based on techniques developed by Maxam and Gilbert (*Proc. Natl Acad Sci USA* (1977) 74:560) or Sanger (Sanger et al. (1977) *Proc. Nat. Acad. Sci* 74:5463). Any of a variety of automated sequencing procedures can be utilized when performing the assays (*Biotechniques* (1995) 19:448), including sequencing by mass spectrometry (see, for example, U.S. Pat. No. 5,547,835 and international patent application Publication Number WO 94/16101, entitled *DNA Sequencing by Mass Spectrometry* by H. Köster; U.S. Pat. No. 5,547,835 and international patent application Publication Number WO 94/21822 entitled *DNA Sequencing by Mass Spectrometry Via Exonuclease Degradation* by H. Köster), and U.S. Pat. No. 5,605,798 and International Patent Application No. PCT/US96/03651 entitled *DNA Diagnostics Based on Mass Spectrometry* by H. Köster; Cohen et al. (1996) *Adv Chromatogr* 36:127-162; and Griffin et al. (1993) *Appl Biochem Biotechnol* 38:147-159).

Sequencing of nucleic acid molecules can also be carried out using next-generation sequencing (NGS). Next-generation sequencing includes any sequencing method that determines the nucleotide sequence of either individual nucleic acid molecules or clonally expanded proxies for individual nucleic acid molecules in a highly parallel fashion (e.g., greater than $10^5$ molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. (2010) *Nature Biotechnology Reviews* 11:31-46, incorporated herein by reference.

In one embodiment, the next-generation sequencing allows for the determination of the nucleotide sequence of an individual nucleic acid molecule (e.g., Helicos BioSciences' HeliScope Gene Sequencing system, and Pacific Biosciences' PacBio RS system). In other embodiments, the sequencing method determines the nucleotide sequence of clonally expanded proxies for individual nucleic acid molecules (e.g., the Solexa sequencer, Illumina Inc., San Diego, Calif; 454 Life Sciences (Branford, Conn.), and Ion Torrent). e.g., massively parallel short-read sequencing (e.g., the Solexa sequencer, Illumina Inc., San Diego, Calif.), which generates more bases of sequence per sequencing unit than other sequencing methods that generate fewer but longer reads. Other methods or machines for next-generation sequencing include, but are not limited to, the sequencers provided by 454 Life Sciences (Branford, Conn.), Applied Biosystems (Foster City, Calif.; SOLiD sequencer), and Helicos BioSciences Corporation (Cambridge, Mass.).

Platforms for next-generation sequencing include, but are not limited to, Roche/454's Genome Sequencer (GS) FLX System, Illumina/Solexa's Genome Analyzer (GA), Life/APG's Support Oligonucleotide Ligation Detection (SOLiD) system, Polonator's G.007 system, Helicos BioSciences' HeliScope Gene Sequencing system, and Pacific Biosciences' PacBio RS system.

NGS technologies can include one or more of steps, e.g., template preparation, sequencing and imaging, and data analysis.

Template Preparation

Methods for template preparation can include steps such as randomly breaking nucleic acids (e.g., genomic DNA or cDNA) into smaller sizes and generating sequencing templates (e.g., fragment templates or mate-pair templates). The spatially separated templates can be attached or immobilized to a solid surface or support, allowing massive amounts of sequencing reactions to be performed simultaneously. Types of templates that can be used for NGS reactions include, e.g., clonally amplified templates originating from single DNA molecules, and single DNA molecule templates.

Methods for preparing clonally amplified templates include, e.g., emulsion PCR (emPCR) and solid-phase amplification.

EmPCR can be used to prepare templates for NGS. Typically, a library of nucleic acid fragments is generated, and adapters containing universal priming sites are ligated to the ends of the fragment. The fragments are then denatured into single strands and captured by beads. Each bead captures a single nucleic acid molecule. After amplification and enrichment of emPCR beads, a large amount of templates can be attached or immobilized in a polyacrylamide gel on a standard microscope slide (e.g., Polonator), chemically crosslinked to an amino-coated glass surface (e.g., Life/APG; Polonator), or deposited into individual PicoTiterPlate (PTP) wells (e.g., Roche/454), in which the NGS reaction can be performed.

Solid-phase amplification can also be used to produce templates for NGS. Typically, forward and reverse primers are covalently attached to a solid support. The surface density of the amplified fragments is defined by the ratio of the primers to the templates on the support. Solid-phase amplification can produce hundreds of millions spatially separated template clusters (e.g., Illumina/Solexa). The ends of the template clusters can be hybridized to universal sequencing primers for NGS reactions.

Other methods for preparing clonally amplified templates also include, e.g., Multiple Displacement Amplification (MDA) (Lasken R. S. *Curr Opin Microbiol.* 2007; 10(5): 510-6). MDA is a non-PCR based DNA amplification technique. The reaction involves annealing random hexamer primers to the template and DNA synthesis by high fidelity enzyme, typically Φ29 at a constant temperature. MDA can generate large sized products with lower error frequency.

Template amplification methods such as PCR can be coupled with NGS platforms to target or enrich specific regions of the genome (e.g., exons). Exemplary template enrichment methods include, e.g., microdroplet PCR technology (Tewhey R. et al., *Nature Biotech.* 2009, 27:1025-1031), custom-designed oligonucleotide microarrays (e.g., Roche/NimbleGen oligonucleotide microarrays), and solution-based hybridization methods (e.g., molecular inversion probes (MIPs) (Porreca G. J. et al., *Nature Methods,* 2007, 4:931-936; Krishnakumar S. et al., *Proc. Natl. Acad. Sci. USA,* 2008, 105:9296-9310; Turner E. H. et al., *Nature Methods,* 2009, 6:315-316), and biotinylated RNA capture sequences (Gnirke A. et al., *Nat. Biotechnol.* 2009; 27(2): 182-9)

Single-molecule templates are another type of templates that can be used for NGS reaction. Spatially separated single molecule templates can be immobilized on solid supports by various methods. In one approach, individual primer molecules are covalently attached to the solid support. Adapters are added to the templates and templates are then hybridized to the immobilized primers. In another approach, single-molecule templates are covalently attached to the solid support by priming and extending single-stranded, single-molecule templates from immobilized primers. Universal primers are then hybridized to the templates. In yet another approach, single polymerase molecules are attached to the solid support, to which primed templates are bound.

Sequencing and Imaging

Exemplary sequencing and imaging methods for NGS include, but are not limited to, cyclic reversible termination (CRT), sequencing by ligation (SBL), single-molecule addition (pyrosequencing), and real-time sequencing.

CRT uses reversible terminators in a cyclic method that minimally includes the steps of nucleotide incorporation, fluorescence imaging, and cleavage. Typically, a DNA polymerase incorporates a single fluorescently modified nucleotide corresponding to the complementary nucleotide of the template base to the primer. DNA synthesis is terminated after the addition of a single nucleotide and the unincorporated nucleotides are washed away. Imaging is performed to determine the identity of the incorporated labeled nucleotide. Then in the cleavage step, the terminating/inhibiting group and the fluorescent dye are removed. Exemplary NGS platforms using the CRT method include, but are not limited to, Illumina/Solexa Genome Analyzer (GA), which uses the clonally amplified template method coupled with the four-color CRT method detected by total internal reflection fluorescence (TIRF); and Helicos BioSciences/HeliScope, which uses the single-molecule template method coupled with the one-color CRT method detected by TIRF.

SBL uses DNA ligase and either one-base-encoded probes or two-base-encoded probes for sequencing. Typically, a fluorescently labeled probe is hybridized to its complementary sequence adjacent to the primed template. DNA ligase is used to ligate the dye-labeled probe to the primer. Fluorescence imaging is performed to determine the identity of the ligated probe after non-ligated probes are washed away. The fluorescent dye can be removed by using cleavable probes to regenerate a 5'-$PO_4$ group for subsequent ligation cycles. Alternatively, a new primer can be hybridized to the template after the old primer is removed. Exemplary SBL platforms include, but are not limited to, Life/APG/SOLiD (support oligonucleotide ligation detection), which uses two-base-encoded probes.

Pyrosequencing method is based on detecting the activity of DNA polymerase with another chemiluminescent enzyme. Typically, the method allows sequencing of a single strand of DNA by synthesizing the complementary strand along it, one base pair at a time, and detecting which base was actually added at each step. The template DNA is immobile, and solutions of A, C, G, and T nucleotides are sequentially added and removed from the reaction. Light is produced only when the nucleotide solution complements the first unpaired base of the template. The sequence of solutions which produce chemiluminescent signals allows the determination of the sequence of the template. Exemplary pyrosequencing platforms include, but are not limited to, Roche/454, which uses DNA templates prepared by emPCR with 1-2 million beads deposited into PTP wells.

Real-time sequencing involves imaging the continuous incorporation of dye-labeled nucleotides during DNA synthesis. Exemplary real-time sequencing platforms include, but are not limited to, Pacific Biosciences platform, which uses DNA polymerase molecules attached to the surface of individual zero-mode waveguide (ZMW) detectors to obtain sequence information when phospholinked nucleotides are being incorporated into the growing primer strand; Life/VisiGen platform, which uses an engineered DNA polymerase with an attached fluorescent dye to generate an enhanced signal after nucleotide incorporation by fluorescence resonance energy transfer (FRET); and LI-COR Biosciences platform, which uses dye-quencher nucleotides in the sequencing reaction.

Other sequencing methods for NGS include, but are not limited to, nanopore sequencing, sequencing by hybridization, nano-transistor array based sequencing, polony sequencing, scanning tunneling microscopy (STM) based sequencing, and nanowire-molecule sensor based sequencing.

Nanopore sequencing involves electrophoresis of nucleic acid molecules in solution through a nano-scale pore which provides a highly confined space within which single-nucleic acid polymers can be analyzed. Exemplary methods of nanopore sequencing are described, e.g., in Branton D. et al., *Nat Biotechnol.* 2008; 26(10):1146-53.

Sequencing by hybridization is a non-enzymatic method that uses a DNA microarray. Typically, a single pool of DNA is fluorescently labeled and hybridized to an array containing known sequences. Hybridization signals from a given spot on the array can identify the DNA sequence. The binding of one strand of DNA to its complementary strand in the DNA double-helix is sensitive to even single-base mismatches when the hybrid region is short or is specialized mismatch detection proteins are present. Exemplary methods of sequencing by hybridization are described, e.g., in Hanna G. J. et al., *J. Clin. Microbiol.* 2000; 38 (7): 2715-21; and Edwards J. R. et al., *Mut. Res.* 2005; 573 (1-2): 3-12.

Polony sequencing is based on polony amplification and sequencing-by-synthesis via multiple single-base-extensions (FISSEQ). Polony amplification is a method to amplify DNA in situ on a polyacrylamide film. Exemplary polony sequencing methods are described, e.g., in US Patent Application Publication No. 2007/0087362.

Nano-transistor array based devices, such as Carbon NanoTube Field Effect Transistor (CNTFET), can also be used for NGS. For example, DNA molecules are stretched and driven over nanotubes by micro-fabricated electrodes. DNA molecules sequentially come into contact with the carbon nanotube surface, and the difference in current flow from each base is produced due to charge transfer between the DNA molecule and the nanotubes. DNA is sequenced by recording these differences. Exemplary Nano-transistor array based sequencing methods are described, e.g., in U.S. Patent Application Publication No. 2006/0246497.

Scanning tunneling microscopy (STM) can also be used for NGS. STM uses a piezo-electric-controlled probe that performs a raster scan of a specimen to form images of its surface. STM can be used to image the physical properties of single DNA molecules, e.g., generating coherent electron tunneling imaging and spectroscopy by integrating scanning tunneling microscope with an actuator-driven flexible gap. Exemplary sequencing methods using STM are described, e.g., in U.S. Patent Application Publication No. 2007/0194225.

A molecular-analysis device which is comprised of a nanowire-molecule sensor can also be used for NGS. Such device can detect the interactions of the nitrogenous material disposed on the nanowires and nucleic acid molecules such as DNA. A molecule guide is configured for guiding a molecule near the molecule sensor, allowing an interaction and subsequent detection. Exemplary sequencing methods using nanowire-molecule sensor are described, e.g., in U.S. Patent Application Publication No. 2006/0275779.

Double ended sequencing methods can be used for NGS. Double ended sequencing uses blocked and unblocked primers to sequence both the sense and antisense strands of DNA. Typically, these methods include the steps of annealing an unblocked primer to a first strand of nucleic acid; annealing a second blocked primer to a second strand of nucleic acid; elongating the nucleic acid along the first strand with a polymerase; terminating the first sequencing primer; deblocking the second primer; and elongating the nucleic acid along the second strand. Exemplary double ended sequencing methods are described, e.g., in U.S. Pat. No. 7,244,567.

Data Analysis

After NGS reads have been generated, they can be aligned to a known reference sequence or assembled de novo.

For example, identifying genetic variations such as single-nucleotide polymorphism and structural variants in a sample (e.g., a tumor sample) can be accomplished by aligning NGS reads to a reference sequence (e.g., a wild-type sequence). Methods of sequence alignment for NGS are described e.g., in Trapnell C. and Salzberg S. L. *Nature Biotech.*, 2009, 27:455-457.

Examples of de novo assemblies are described, e.g., in Warren R. et al., *Bioinformatics,* 2007, 23:500-501; Butler J. et al., *Genome Res.,* 2008, 18:810-820; and Zerbino D. R. and Birney E., *Genome Res.,* 2008, 18:821-829.

Sequence alignment or assembly can be performed using read data from one or more NGS platforms, e.g., mixing Roche/454 and Illumina/Solexa read data.

Algorithms and methods for data analysis are described in U.S. Ser. No. 61/428,568, filed Dec. 30, 2010, incorporated herein by reference.

Screening Methods

In another aspect, the invention features a method, or assay, for screening for agents that modulate, e.g., inhibit, the expression or activity of a mutant gene, e.g., a mutant cell cycle gene, such as CDKN2A, CDKN2B or CCND1 as described herein. The method includes contacting a mutant polypeptide, or a cell expressing a mutant gene, with a candidate agent; and detecting a change in a parameter associated with the mutant gene, e.g., a change in the expression or an activity of the mutant gene. The method can, optionally, include comparing the treated parameter to a reference value, e.g., a control sample (e.g., comparing a parameter obtained from a sample with the candidate agent to a parameter obtained from a sample without the candidate agent). In one embodiment, if a decrease in expression or activity of the mutant gene is detected, the candidate agent is identified as an inhibitor. In another embodiment, if an increase in expression or activity of the mutant gene is detected, the candidate agent is identified as an activator. In certain embodiments, the mutant gene is a nucleic acid molecule or a polypeptide as described herein.

In one embodiment, the contacting step is effected in a cell-free system, e.g., a cell lysate or in a reconstituted system. In other embodiments, the contacting step is effected in a cell in culture, e.g., a cell expressing a mutant gene, such as a mutant cell cycle gene (e.g., a mammalian cell, a tumor cell or cell line, a recombinant cell). In yet other embodiments, the contacting step is effected in a cell in vivo (a mutant gene-expressing cell present in a subject, e.g., an animal subject (e.g., an in vivo animal model).

Exemplary parameters evaluated include one or more of:

(i) a change in binding activity, e.g., direct binding of the candidate agent to a mutant polypeptide; a binding competition between a known ligand and the candidate agent to a mutant polypeptide;

(ii) a change in transcriptional activation activity or DNA binding activity as measured, for example, by fusing a response element to a reporter gene; DNA binding activity can also be measure by gel-shift assay;

(iii) a change in an activity of a cell containing a mutant gene (e.g., a tumor cell or a recombinant cell), e.g., a change in proliferation, morphology or tumorigenicity of the cell;

(iv) a change in tumor present in an animal subject, e.g., size, appearance, proliferation, of the tumor; or (v) a change in the level, e.g., expression level, of a mutant polypeptide or nucleic acid molecule.

EXAMPLES

Example 1

Massively Parallel Sequencing Assays to Identify Novel Alterations

The following exemplifies the use of massively parallel sequencing assays to identify mutations in biopsy samples from patients with HNSCC (Head and Neck Squamous Cell Carcinoma).

Massively parallel sequencing technology was used to examine formalin fixed paraffin embedded (FFPE) samples of HNSCC. This assay can identify all classes of DNA alterations (e.g., base substitutions, insertions and deletions, copy number alterations and rearrangements) in a single diagnostic test. Patient samples were analyzed according to whether the patient was positive for human papillomavirus (HPV[+]) or negative for HPV (HPV[−]).

FIG. 1 is a summary of the result of the sequencing analysis. Most of the mutant genes identified carried either point mutations or mutations that resulted in copy number alterations. Samples contained point mutations in certain genes or mutations that resulted in copy number alterations (CNA). In some HPV+ patients, both types of mutations were identified in the PIK3CA gene.

The summary of mutations observed is shown in Tables 1 and 4.

TABLE 1

Summary of mutations observed in HPV+ and HPV− patients

| | HPV+ | | HPV− | |
|---|---|---|---|---|
| Gene | Mutation type | % samples carrying mutation | Mutation Type | % samples carrying mutation |
| PIK3CA[a] | Point mutations and/or CNA | ~33% | Point mutations or CNA | ~22% |
| FBXW7 | Point mutations | ~19% | CNA | ~5% |
| PTEN[a] | Point mutations or CNA | ~19% | Point mutations | ~6% |
| SOX2 | CNA | ~16% | CNA | ~6% |
| BCL2L1 | CNA | ~12% | — | 0% |
| KRAS | Point mutations | ~12% | — | 0% |
| NF1 | Point mutations | ~8% | — | 0% |
| RB1 | Point mutations | ~4% | — | 0% |
| STK11[a] | Point mutations | ~4% | — | 0% |
| NOTCH1 | Point mutations | ~4% | Point mutations | ~5% |
| RICTOR | CNA | ~4% | CNA | ~5% |
| FGFR1 | — | 0% | CNA | ~5% |
| MCL1 | — | 0% | CNA | ~5% |
| MYC | — | 0% | CNA | ~5% |
| FGFR3 | — | 0% | Point mutations | ~5% |
| KDM6A | — | 0% | Point mutations | ~5% |
| LRP1B | — | 0% | Point mutations | ~5% |
| PKHD1 | — | 0% | Point mutations | ~5% |
| SUFU | — | 0% | Point mutations | ~5% |
| TET2 | — | 0% | Point mutations | ~5% |
| MDM2 | — | 0% | CNA | ~12% |
| EGFR | — | 0% | CNA | ~16% |
| CDKN2A[b] | — | 0% | Point mutations or CNA | ~50% |
| CCND1[b] | CNA | ~4% | CNA | ~65% |
| TP53 | Point mutations | ~6% | Point mutations | ~100% |

[a]PI3K pathway gene
[b]cell cycle gene

Materials and Methods

Sample Collection, p16 staining and DNA Extraction. Twenty HPV+ and twenty HPV− oropharyngeal carcinomas were selected, all formalin fixed paraffin-embedded (Table 2). HPV status was confirmed by p16 staining, and by quantitative PCR for HPV-16 E6, having been shown to have 97% sensitivity, 94% specificity and to be the best discriminator of favourable outcome. Sequencing demonstrated 100% concordance of HPV status. All samples were laser-captured microdissected (LCM) to separate tumor epithelial from surrounding stromal tissues, enriching tumor DNA for further analyses. These were processed as 10 μm thick unstained slides which were reviewed by an expert pathologist who had marked the slides for tumor subtype enrichment in a corresponding H&E stained section. LCM was carried out on P.A.L.M. MembraneSlide 1.0 PEN slides (Zeiss Microimaging, Munich, Germany) using the Zeiss Palm Microbeam™ system. Tissue was collected into extraction tubes and processed using the QIAamp DNA FFPE Tissue Kit (Qiagen, Hilden, Germany). Extracted DNA was quantified using a standardized PicoGreen fluorescence assay (LifeTechnologies, Carlsbad, Calif.).

TABLE 2

Demographics of twenty HPV+ and twenty HPV− oropharyngeal carcinomas selected for analysis.

| 0 | HPV+ (n = 20) | HPV− (n = 20) |
|---|---|---|
| Median Age (range) | 56.5 years (42-81) | 58 years (45-77) |
| Tumor Site | Oropharynx: 20 | Oropharynx: 20 |
| Tumor Grade | Well diff: 1 | Well diff: 0 |
| | Mod diff: 9 | Mod diff: 16 |
| | Poorly diff: 10 | Poorly diff: 4 |
| Tumor Stage (T) | T1: 5 | T1: 1 |
| | T2: 8 | T2: 4 |
| | T3: 3 | T3: 5 |
| | T4: 3 | T4: 10 |
| | N/a: 1 | N/a: 0 |
| Cervical Lymph Node Involvement | Yes: 16 | Yes: 13 |
| | No: 2 | No: 6 |
| | N/a: 2 | N/a: 1 |
| Smoking | Ever: 9 | Ever: 15 |
| | Never: 8 | Never: 0 |
| | N/a: 3 | N/a: 5 |
| Alcohol | Heavy Drinker (>20 U/w): 2 | Heavy Drinker (>20 U/w): 12 |
| | Occ alcohol: 5 | Occ alcohol: 3 |
| | Never: 4 | Never: 0 |
| | N/a: 9 | N/a: 5 |

DNA Library Construction and Hybrid Capture. Molecular barcode-indexed ligation-based sequencing libraries were constructed using 50-200 ng of total genomic DNA recovered from the sample. Libraries were hybridization captured with custom biotinylated RNA oligo pools (custom SureSelect kit, Agilent) representing 3,230 exons in 182 cancer-related genes plus 37 introns from 14 genes often rearranged in cancer (FIGS. 2A and 2B).

Sequencing and Analysis. Paired end sequencing (49×49 cycles) was performed using the HiSeq2000 (Illumina). Sequence data from gDNA, available from 18 HPV+ and 16 HPV− samples, were mapped to the reference human genome (hg19) using the BWA aligner (Li et al. Bioinformatics 25:2078-9) and processed using publicly available SAMtools (Li et al., Bioinformatics 25:2078-9, 2009), Picard (online at picard.sourceforge.net) and GATK (McKenna et al., Genome Res. 20-1297-303, 2010). Genomic base substitutions and indels were detected using custom tools optimized for mutation calling in heterogeneous tumor samples, based on statistical modeling of sequence quality scores and local sequence assembly. Variations were filtered using dbSNP_135_ENREF_1 (online at ncbi.nlm.nih.gov/projects/SNP/) and a custom artifact database, then annotated for known and likely somatic mutations using the COSMIC (Forbes et al., Nucl. Acids Res. 39:D945-50, 2011). Copy number alterations were detected by comparing targeted genomic DNA sequence coverage with a process-matched normal control sample. Genomic rearrangements were detected by clustering chimeric reads mapping to targeted introns.

Validation of selected mutations by Sequenom Onco-Carta. DNA extracted from FFPE samples were sent to Sequenom (Hamburg, Germany) for blind testing and analysis, using Sequenom OncoCarta panels v1.0 and v3.0, as previously described (Fumagalli et al., BMC Cancer 10:101, 2010).

Confirmation of copy number changes by Infinium CNV Profiling. Using previously obtained Infinium HumanMethylation450 BeadChip methylation data on sequenced samples (manuscript submitted), the Bioconductor package 'DNAcopy' (online at bioc.ism.ac.jp/2.10/bioc/html/DNAcopy.html) was applied to calculate the copy number of the majority of sequenced samples.

Immunohistochemistry and interpretation of results. All sequenced HNSCC samples were stained for PTEN and for Cyclin D1. Antibody 04-409 (Millipore-Merck KGaA, Darmstadt, Germany) was used for PTEN staining and antibody P2D11F11 (Novocastra) was used for Cyclin D1 staining of 10 μm thick slides. The stained slides were examined and scored as previously described (Djordjevic et al., Mod. Pathol. 25:699-708, 2012), by two experienced histopathologists.

Results

Figure 7A:
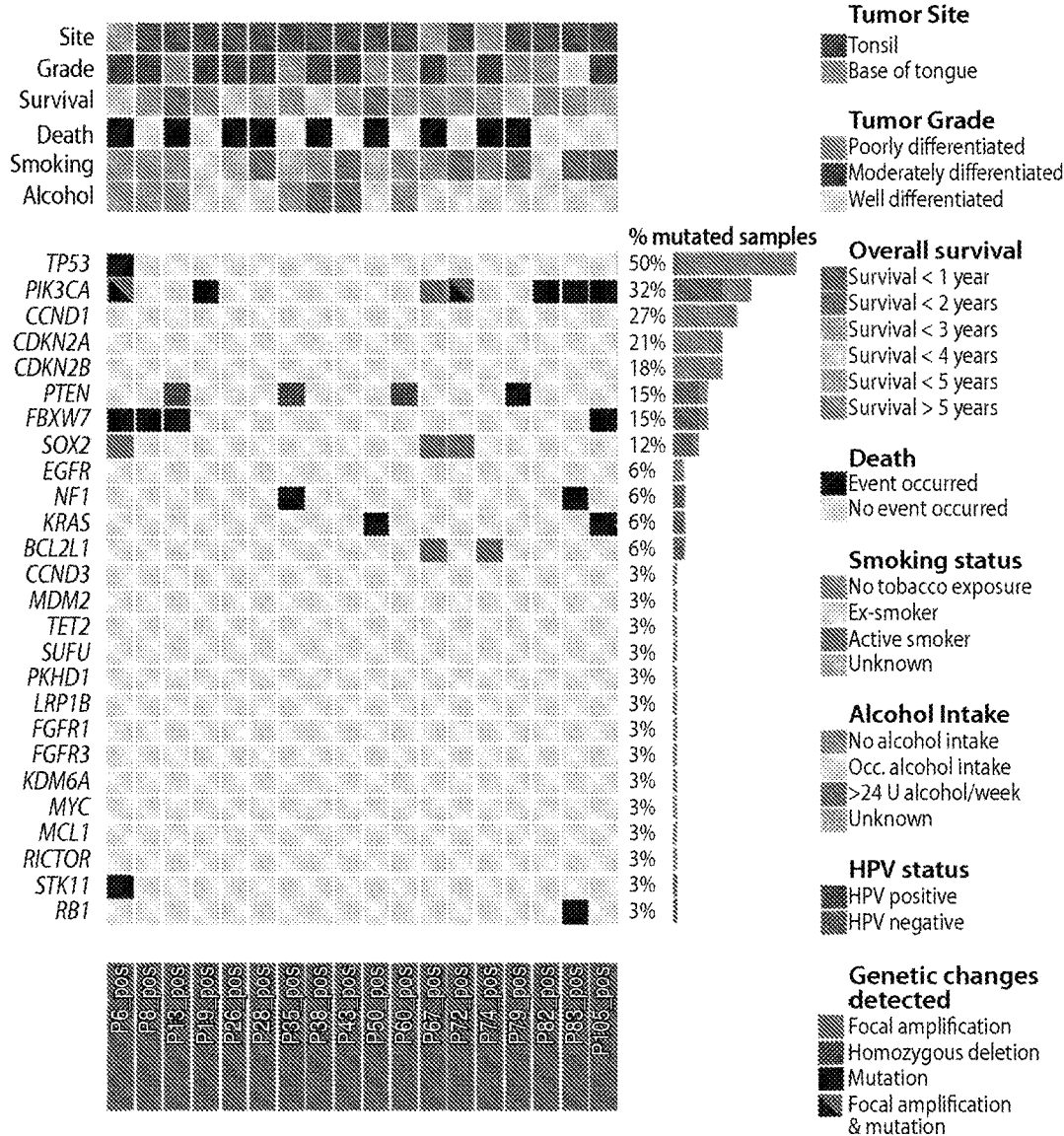
FIGS. 7A and 7B are heat maps of genomic changes associated with patient characteristics and observed changes. Demographic and histologic data are described above the heatmap.
Figure 7B:
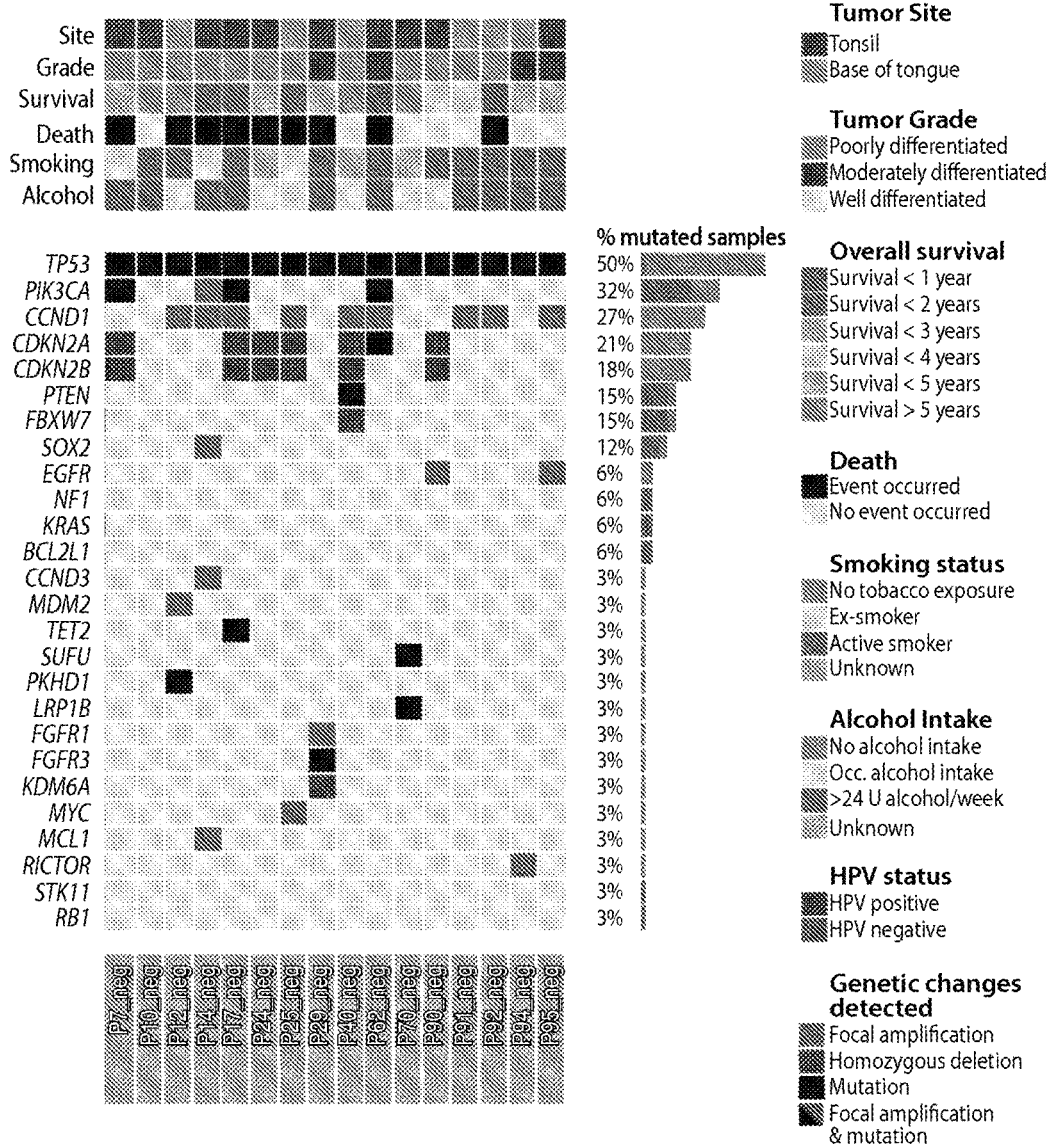

Patient demographic data. The median age was slightly higher in the HPV− group (58 vs. 56.5 years) (Table 2). Male to female ratio was similar between the Groups, and the majority of cases show moderately or poorly differentiated histology with evidence of lymph nodal involvement at presentation. The vast majority of HPV− cases were in active smokers and/or heavy alcohol users (FIGS. 7A and 7B).

Figure 3A:
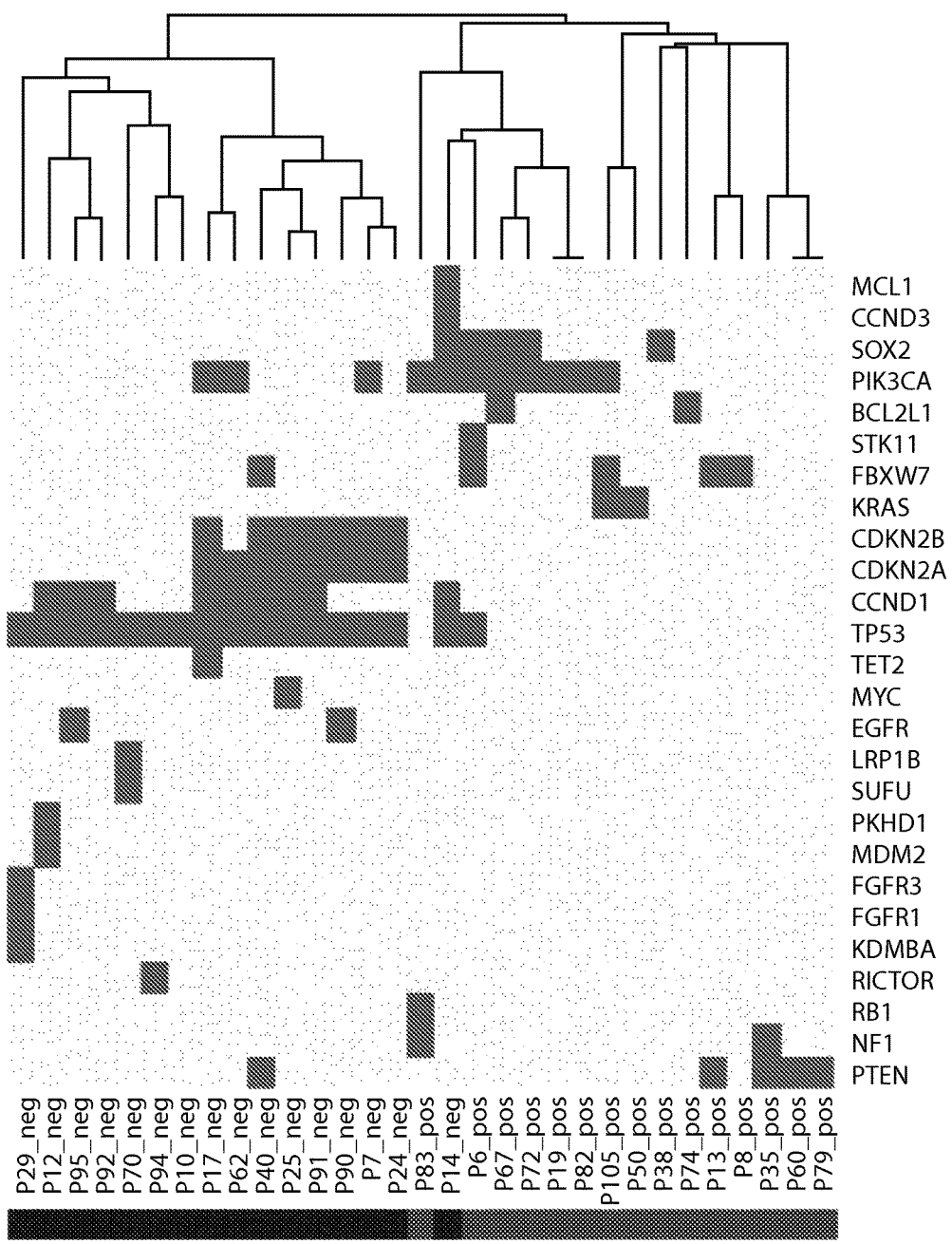
FIGS. 3A and 3B are representations of hierarchical clustering of HPV+ and HPV− HNSCC samples using all detected genetic changes (FIG. 3A) or excluding mutations within TP53 (FIG. 3B).
Figure 3B:
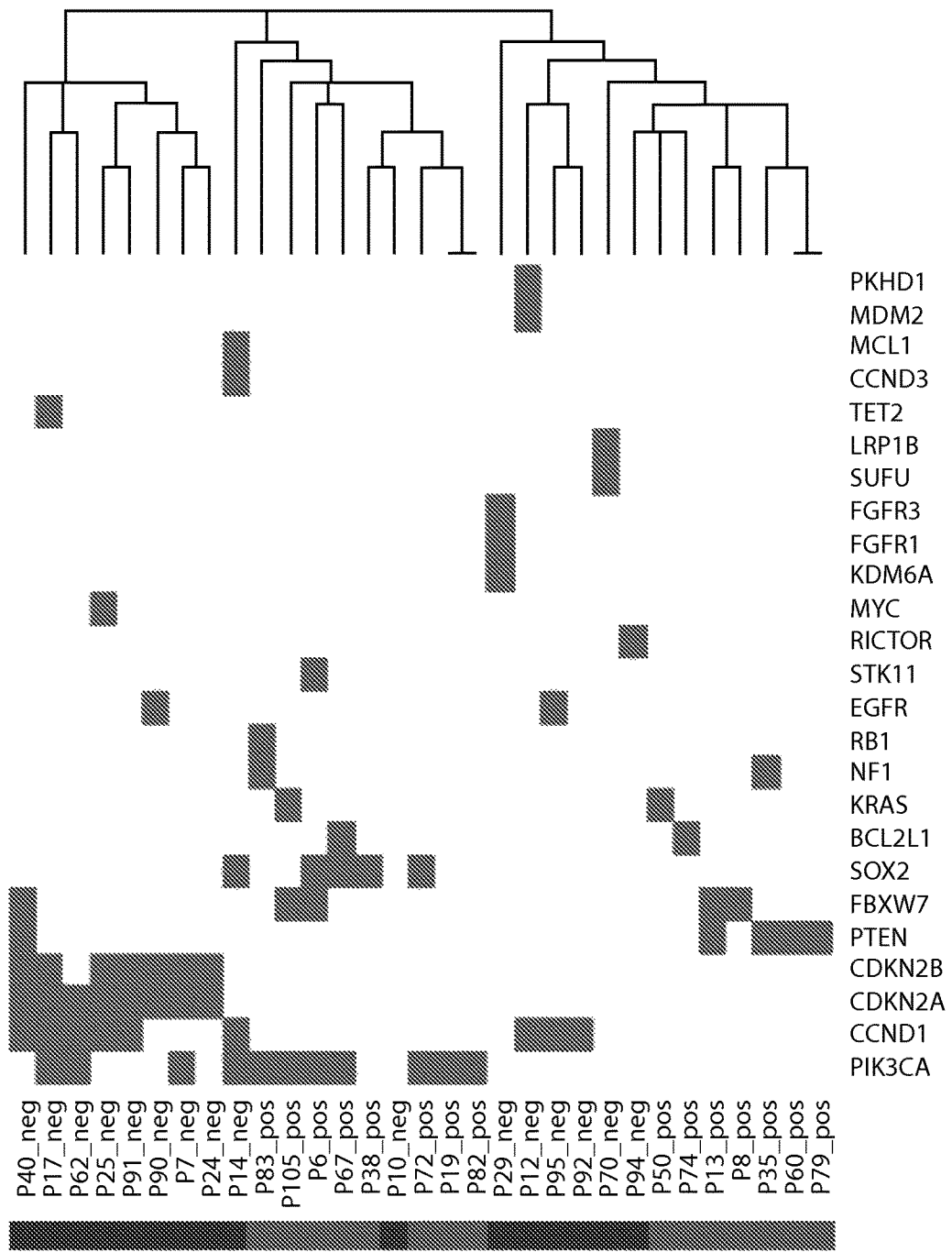

Next generation sequencing. Sequence analysis revealed that HPV+ and HPV− oropharyngeal carcinomas cluster into two distinct subgroups, with few overlapping genetic alterations (FIG. 3A). TP53 mutations were detected in 100% of HPV− samples. The list of observed TP53 mutations is illustrated in Table 3. Samples did not cluster into two distinct subgroups after exclusion of the TP53 mutation data (FIG. 3B). Copy number alterations in CCND1 amplification and CDKN2A/B deletions were exclusively detected in HPV− cases (in around 55% and 40% of cases respectively). PIK3CA mutation or amplification, and PTEN inactivation by gene copy loss or mutation were seen in over 60% of HPV+ tumors, and in 31% HPV− tumors. FBXW7 alterations were present in over 15% of all samples, and SOX2 amplifications were observed in 12% of cases.

TABLE 3

TP53 Mutations Observed

| Sample Name | TP53 Mutations |
| --- | --- |
| P6_pos | R290C |
| P8_pos | None |
| P13_pos | None |
| P19_pos | None |
| P26_pos | None |
| P28_pos | None |
| P35_pos | None |
| P38_pos | None |
| P43_pos | None |
| P50_pos | None |
| P60_pos | None |
| P67_pos | None |
| P72_pos | None |
| P74_pos | None |
| P79_pos | None |
| P82_pos | None |
| P83_pos | None |
| P105_pos | None |
| P7_pos | R175H |
| P10_pos | Y234H |
| P12_pos | Y220S |
| P14_pos | R273L |
| P17_pos | G154fs |
| P24_pos | L130fs |
| P25_pos | Q165 |
| P29_pos | Y236 |
| P40_pos | R306 |
| P62_pos | Y220C |
| P70_pos | Q104 |
| P90_pos | L114fs, L330fs |
| P91_pos | R337L |
| P92_pos | R335L, G334V |
| P94_pos | T155P |
| P95_pos | 920-1C > T splice |

Figure 4:
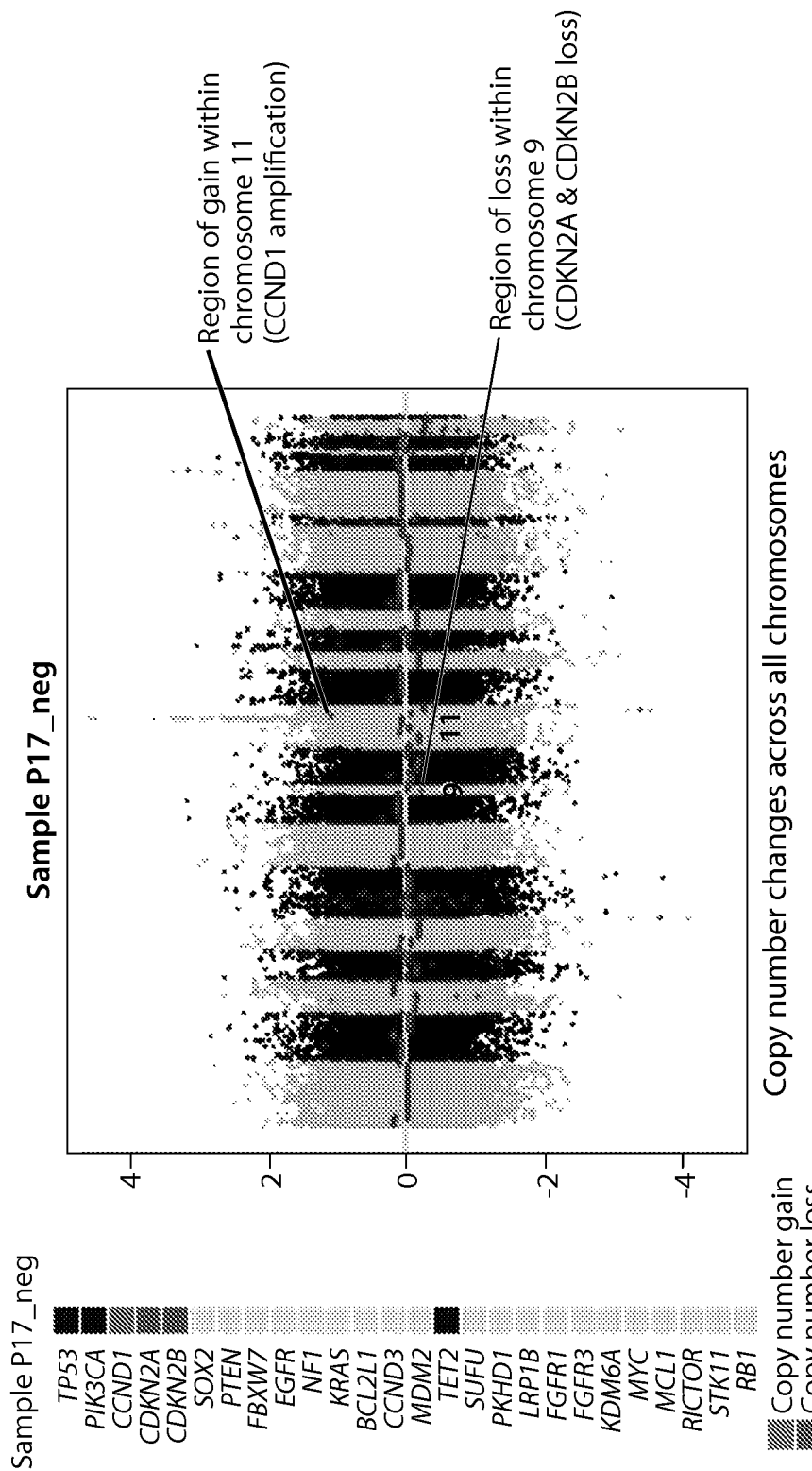
FIG. 4 is a graph depicting that genetic changes in sample "P17_neg" detected by NGS.
Figure 5:
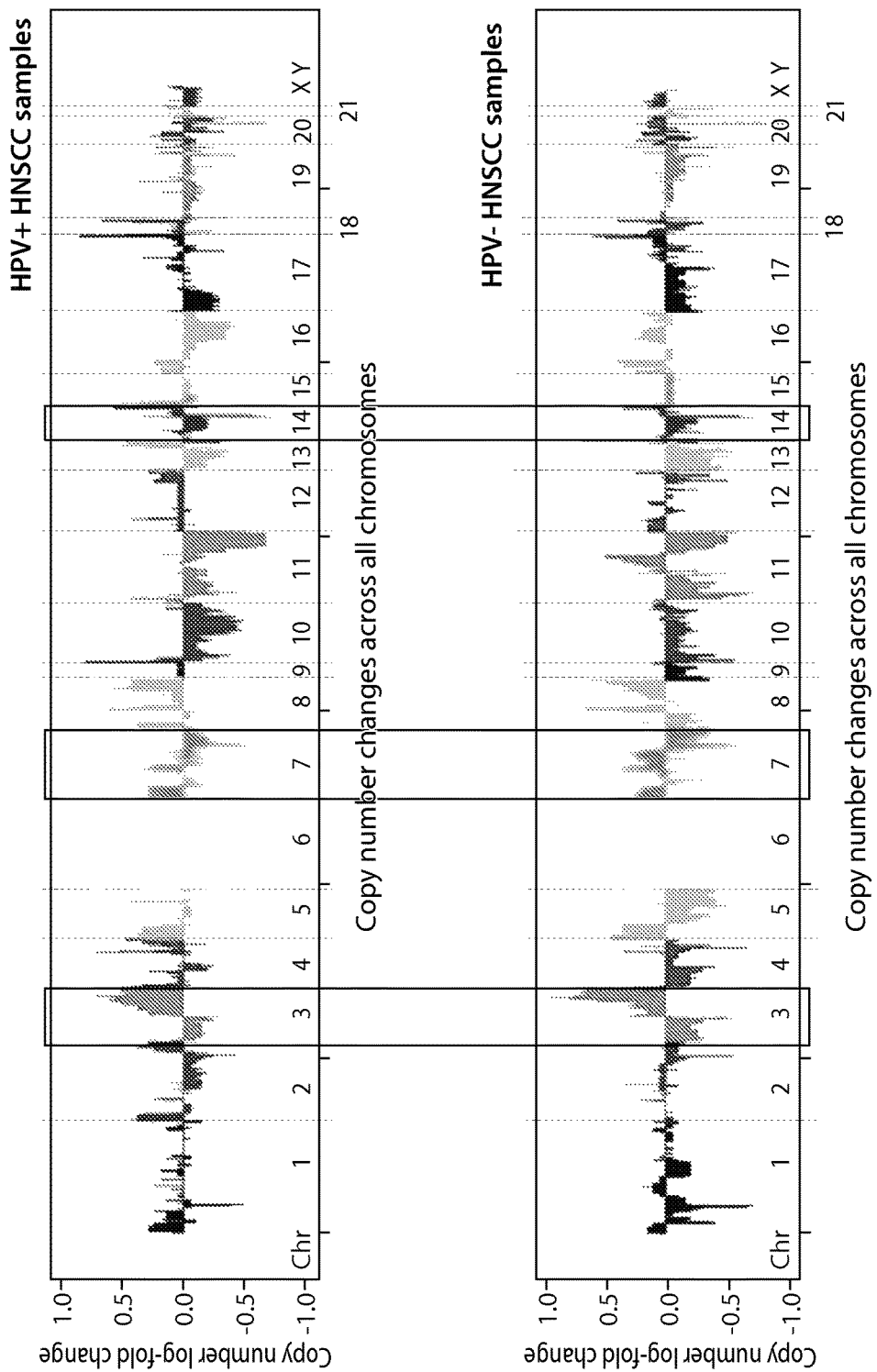
FIG. 5 is Infinium CNV profiling of HPV+ and HPV− HNSCC samples.

Validation of obtained results. Copy number gains and losses detected by NGS were interrogated by Infinium CNV profiling. 42 of 44 (95%) copy number alterations detected by sequencing were confirmed (FIG. 4). In order to obtain a global picture, copy number alterations were detected by Infinium CNV profiling. Comparing the obtained genome-wide copy number alteration profiles between HPV+ and HPV− cancers revealed that overall, similar genomic regions harbor concordant copy number changes in both groups (in particular in chromosomes 3, 7 and 14). Amplification of 3q seemed to be a particular target in both HPV+ and HPV− HNSCC lesions (FIG. 5).

The mutations detected by NGS were validated by Sequenom OncoCarta panels v1.0 and v3.0. As the NGS exome sequencing targeted the whole gene sequence, and the Sequenom OncoCarta panels targeted only specific mutational hotspots of certain genes, the majority of NGS detected mutations were not included in the Sequenom analysis. Eight out of 9 mutations that were detected by NGS were also confirmed by Sequenom. One PIK3CA mutation in sample P72_pos was called at 1% allele frequency by NGS, and this mutation was therefore unlikely to be detected by Sequenom analysis.

For CCND1 and PTEN the findings were also validated by immunohistochemistry. Genomic alterations in CCND1 were confirmed by Cyclin D1 immunochemistry with strong expression of Cyclin D1 protein in 8 of 9 CCND1 amplified cases (and intermediate expression in the remaining case). PTEN loss and mutation was validated by immunohistochemistry. PTEN staining was negative in all cases in which deep sequencing revealed a homozygous deletion or mutation. Four additional samples displayed low PTEN protein expression. In three of these cases a heterozygous deletion/single copy loss of PTEN was present, as detected by NGS. In the remaining sample other mechanisms may explain the loss of expression, such as an epigenetic alteration or changes in the posttranscriptional regulation of PTEN.

Figure 6:
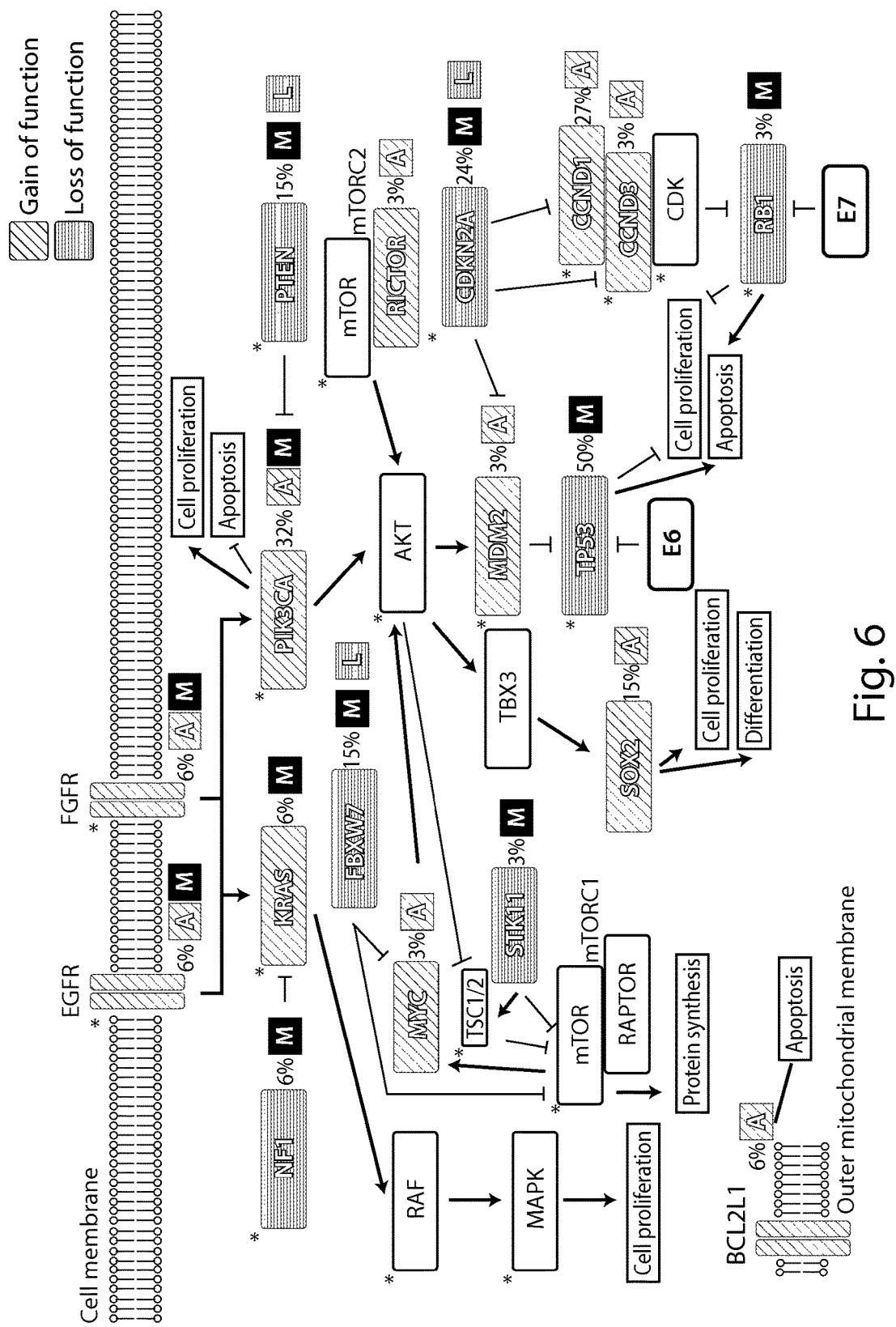
FIG. 6 is a comparison of mutated pathways in HNSCC and lung adenocarcinoma.

Integration with mutation data from lung cancer. Genetic changes described in lung adenocarcinoma in previous studies (Ding et al., Nature 455:1069-75, 2008) were compared to our data from HPV− HNSCC (FIG. 6).

We discovered that HPV⁻ HNSCC patients are more likely to carry mutations in cell cycle genes, such as CDKN2A or CDKN2B, or CCND1, than are HPV patients, and that HPV HNSCC patients are more likely to carry mutations in genes in the phosphatidylinositol-3 kinase (PI3K) family, such as PIK3CA, PTEN and STK11. Thus, an HNSCC patient diagnosed as HPV⁻ can be administered cell cycle inhibitors, such as cdk (cyclin-dependent kinase) inhibitors.

Overall, sequence analysis revealed that HPV+ and HPV− oropharyngeal carcinomas cluster into two distinct subgroups, with few overlapping genetic alterations. These data concur with epidemiological and clinical data, indicating that HPV+ HNSCC is a distinct disease entity.

The fact that targeted deep next generation sequencing revealed that TP53 is mutated in 100% of HPV− samples indicates that TP53 is likely to be a ubiquitous early event in the pathogenesis of oropharyngeal HNSCC caused by smoking, and/or alcohol use. In HPV+ disease, E6 leads to TP53 functional inactivation. Consistent with this, only one TP53 mutation was identified in an HPV+ tumor. Furthermore, this mutation (R290C, Table 3) caused only a 40% decrease in TP53 function.

The data for HPV− oropharyngeal cancer indicated that the frequency of CCND1 amplifications (in around 55% of cases) and CDKN2A/B deletions (in around 40% of cases) were higher than previously reported. In HPV+ cancer, the oncoprotein E7 leads to cell cycle dysregulation by substituting for cyclin D gain-of-function and cyclin dependent kinase inhibitor loss-of-function activities. Overall, this indicates that direct dysregulation of the cell cycle is a key mechanism for oropharyngeal tumors to evolve.

We demonstrated for the first time inactivating mutations in NF1 and STK11 in HPV+ HNSCC.

Overall, our data strongly support a causal role for HPV in oropharyngeal carcinogenesis by overcoming the requirement for genetic lesions in the TP53 and RB 1 tumor suppressor pathways evident in the HPV− tumors.

TABLE 4

| Tissue type | HPV status | Column 3 somatic mutations[1] (mutant allele frequency/coverage depth) | Column 4 somatic mutations[2] | Amplification of genes known to be amplified in cancer (CN level, exon span) | Deletions of genes known to be deleted in cancer |
|---|---|---|---|---|---|
| Oropharynx (base of tongue) | pos | FBXW7_c.1436G > A_p.R479Q(0.10, 1868), FBXW7_c.1513C > T_p.R505C(0.12, 2417), FBXW7_c.1514G > A_p.R505H(0.08, 2429), PIK3CA_c.1624G > A_p.E542K(0.26, 3391), STK11_c.971C > T_p.P324L(0.03, 711), TP53_c.868C > T_p.R290C(0.06, 762) | none | PIK3CA_gain(6, PIK3CA_target_6-20); SOX2_gain(6, SOX2_target_1-1) | none |
| — | — | FBXW7_c.1436G > A_p.R479Q(0.10, 535), FBXW7_c.1513C > T_p.R505C(0.13, 625), FBXW7_c.1514G > A_p.R505H(0.08, 625), PIK3CA_c.1624G > A_p.E542K(0.27, 990), TP53_c.868C > T_p.R290C(0.10, 225) | none | PIK3CA_gain(5, PIK3CA_target_6-20); SOX2_gain(5, SOX2_target_1-1) | none |
| Oropharynx (tonsil) | neg | PIK3CA_c.1035T > A_p.N345K(0.38, 1356), TP53_c.524G > A_p.R175H(0.27, 535) | none | none | CDKN2A_loss(0, CDKN2A_target_3-4); CDKN2B_loss(0, CDKN2B_target_1-2) |
| Oropharynx (tonsil) | pos | FBXW7_c.1436G > A_p.R479Q(0.41, 630) | none | none | none |
| Oropharynx (tonsil) | neg | TP53_c.700T > C_p.Y234H(0.16, 221) | none | none | none |
| Oropharynx (base of tongue) | neg | PKHD1_c.3241C > T_p.R1081C(0.62, 406), TP53_c.659A > C_p.Y220S(0.84, 420) | none | CCND1_gain(7, CCND1_target_1-5); MDM2_gain(7, MDM2_target_1-11) | none |
| Oropharynx (tonsil) | pos | FBXW7_c.1513C > T_p.R505C(0.35, 402) | none | none | PTEN_loss(0, PTEN_target_1-9) |
| Oropharynx (tonsil) | neg | TP53_c.818G > T_p.R273L(0.65, 390) | none | CCND1_gain(12, CCND1_target_1-5); CCND3_gain(14, CCND3_target_1-5); | none |

TABLE 4-continued

| Tissue type | HPV status | Column 3 somatic mutations[1] (mutant allele frequency/ coverage depth) | Column 4 somatic mutations[2] | Amplification of genes known to be amplified in cancer (CN level, exon span) | Deletions of genes known to be deleted in cancer |
|---|---|---|---|---|---|
| | | | | MCL1_gain(12, MCL1_target_1-3); PIK3CA_gain(7, PIK3CA_target_1-20); SOX2_gain(7, SOX2_target_1-1) | |
| Oropharynx (tonsil) | neg | PIK3CA_c.1633G > A_p.E545K(0.28, 1699), TP53_c.456delG_p. G154fs*16(0.65, 594) | TET2_c.4333C > T_p. Q1445*(0.04, 984) | CCND1_gain(13, CCND1_target_1-5) | CDKN2A_loss(0, CDKN2A_target_1-4); CDKN2B_loss(0, CDKN2B_target_1-2) |
| Oropharynx (tonsil) | pos | PIK3CA_c.1624G > A_p.E542K(0.07, 933) | none | none | none |
| Oropharynx (tonsil) | neg | none | TP53:NM_000546: c.388_392delTTGAG_p. L130fs*17:frameshift (0.70, 183) | none | CDKN2A_loss(0, CDKN2A_target_1-4); CDKN2B_loss(0, CDKN2B_target_1-2) |
| Oropharynx (base of tongue) | neg | TP53_c.493C > T_p. Q165*(0.69, 617) | none | CCND1_gain(16, CCND1_target_1-5); MYC_gain(8, MYC_target_1-3) | CDKN2A_loss(0, CDKN2A_target_1-4); CDKN2B_loss(0, CDKN2B_target_1-2) |
| Oropharynx (tonsil/base of tongue) | pos | none | none | none | none |
| Oropharynx (tonsil/base of tongue) | pos | none | none | none | none |
| Oropharynx (tonsil/base of tongue) | neg | FGFR3_c.746C > G_p. S249C(0.15, 550), TP53_c.708C > A_p. Y236*(0.64, 294) | none | FGFR1_gain(10, FGFR1_target_1-17) | KDM6A_loss(0, KDM6A_target_1-29) |
| Oropharynx (tonsil) | pos | NF1_c.3721C > T_p. R1241*(0.02, 1429), NF1_c.4600C > T_p. R1534*(0.01, 1911) | none | none | PTEN_loss(0, PTEN_target_1-9) |
| Oropharynx (tonsil) | pos | none | none | none | none |
| Oropharynx (base of tongue) | neg | TP53_c.916C > T_p. R306*(0.84, 710) | PTEN:NM_000314: c.79 + 1G > T:splice (0.81, 782) | CCND1_gain(8, CCND1_target_1-5) | CDKN2A_loss(0, CDKN2A_target_1-4); CDKN2B_loss(0, CDKN2B_target_1-2); FBXW7_loss(0, FBXW7_target_1-13) |
| Oropharynx (tonsil) | pos | none | none | none | none |
| Oropharynx (tonsil/base of tongue) | pos | KRAS_c.35G > A_p. G12D(0.25, 513) | none | none | none |
| Oropharynx (tonsil) | pos | none | none | none | PTEN_loss(0, PTEN_target_1-9) |
| Oropharynx (tonsil) | neg | TP53_c.659A > G_p. Y220C(0.55, 112) | CDKN2A:NM_000077: c.458 – 1C > T:splice(0.46, 91), PIK3CA_c.3085G > C_p.D1029H(0.18, 184) | CCND1_gain(15, CCND1_target_1-5) | none |
| Oropharynx (base of tongue) | pos | none | none | BCL2L1_gain(11, BCL2L1_target_1-1); PIK3CA_gain(8, PIK3CA_target_6-20); SOX2_gain(8, SOX2_target_1-1) | none |
| Oropharynx (tonsil) | neg | TP53_c.310C > T_p. Q104*(0.67, 479) | LRP1B:NM_018557: c.7154_7155insT_p. I2387fs*2:frameshift (0.17, 364), SUFU:NM_016169: c.30_30delC_p. G11fs*85:frameshift (0.34, 822) | none | none |
| Oropharynx (tonsil) | pos | PIK3CA_c.1633G > A_p.E545K(0.01, 1853) | none | PIK3CA_gain(6, PIK3CA_target_1-20); SOX2_gain(6, SOX2_target_1-1) | none |

TABLE 4-continued

| Tissue type | HPV status | Column 3 somatic mutations[1] (mutant allele frequency/ coverage depth) | Column 4 somatic mutations[2] | Amplification of genes known to be amplified in cancer (CN level, exon span) | Deletions of genes known to be deleted in cancer |
|---|---|---|---|---|---|
| Oropharynx (base of tongue) | pos | none | none | BCL2L1_gain(11, BCL2L1_target_1-1) | none |
| Oropharynx (tonsil) | pos | PTEN_c.733C > T_p.Q245*(0.38, 393) | none | none | none |
| Oropharynx (tonsil) | pos | PIK3CA_c.3140A > T_p.H1047L(0.24, 695) | none | none | none |
| Oropharynx (tonsil) | pos | NF1_c.3721C > T_p.R1241*(0.06, 493), RB1_c.1735C > T_p.R579*(0.41, 288) | NF1:NM_001042492:c.4700C > A_p.S1567*(0.06, 580), PIK3CA_c.2176G > A_p.E726K(0.49, 420) | none | none |
| Oropharynx (tonsil) | neg | none | TP53:NM_000546:c.339_340insA_p.L114fs*35:frameshift(0.60, 306) | EGFR_gain(7, EGFR_target_1-29) | CDKN2A_loss(0, CDKN2A_target_1-4); CDKN2B_loss(0, CDKN2B_target_1-2) |
| Oropharynx (base of tongue) | neg | TP53_c.1010G > T_p.R337L(0.29, 127) | TP53:NM_000546:c.986_986delG_p.L330fs*15:frameshift(0.18, 197) | CCND1_gain(16, CCND1_target_1-5) | none |
| Oropharynx (base of tongue) | neg | TP53_c.1001G > T_p.G334V(0.73, 95), TP53_c.1004G > T_p.R335L(0.74, 92) | none | CCND1_gain(7, CCND1_target_1-5) | none |
| Oropharynx (base of tongue) | neg | TP53_c.463A > C_p.T155P(0.62, 121) | none | RICTOR_gain(7, RICTOR_target_1-39) | none |
| Oropharynx (tonsil) | neg | none | TP53:NM_000546:c.920 – 1C > T:splice(0.43, 225) | CCND1_gain(8, CCND1_target_1-5); EGFR_gain(13, EGFR_target_1-29) | none |
| Oropharynx (tonsil) | pos | FBXW7_c.1099C > T_p.R367*(0.22, 1380), KRAS_c.35G > A_p.G12D(0.25, 1892), PIK3CA_c.1633G > A_p.E545K(0.32, 2759) | none | none | none |
| Cell line | pos | none | none | none | none |
| Cell line | pos | none | NOTCH1:NM_017617:c.574G > T_p.G192*(0.96, 330) | RICTOR_gain(7, RICTOR_target_1-39) | none |
| Cell line | pos | TP53_c.770T > G_p.L257R(0.50, 787) | none | CCND1_gain(13, CCND1_target_1-5) | none |
| Cell line | — | CDKN2A_c.220G > A_p.D74N(0.99, 144), TP53_c.583A > T_p.I195F(1.00, 1340) | none | CCND1_gain(12, CCND1_target_1-5); MDM2_gain(8, MDM2_target_1-11) | none |
| Cell line | neg | none | NOTCH1:NM_017617:c.158_158delA_p.V53fs*47:frameshift(0.99, 181), TP53:NM_000546:c.450_451insG_p.P153fs*28:frameshift(0.84, 351) | CCND1_gain(12, CCND1_target_1-5); EGFR_gain(16+, EGFR_target_1-29) | none |
| — | — | none | none | none | none |
| — | — | none | none | none | PTEN_loss(0, PTEN_target_1-9) |
| — | — | none | none | none | none |
| — | — | none | none | BCL2L1_gain(9, BCL2L1_target_1-1) | none |
| — | — | PIK3CA_c.3140A > T_p.H1047L(0.25, 434) | none | none | none |
| — | — | FBXW7_c.1099C > T_p.R367*(0.24, 940), KRAS_c.35G > A_p.G12D(0.23, 1288), | none | none | none |

TABLE 4-continued

| Tissue type | HPV status | Column 3 somatic mutations[1] (mutant allele frequency/ coverage depth) | Column 4 somatic mutations[2] | Amplification of genes known to be amplified in cancer (CN level, exon span) | Deletions of genes known to be deleted in cancer |
|---|---|---|---|---|---|
| | | PIK3CA_c.1633G > A_p.E545K(0.33, 1980) | | | |

[1]The "column 3 somatic mutations" include non-synonymous, nonsense, conserved splice site, small indel, large deletion, or large amplification mutations.
[2]The "column 4 somatic mutations" are mutations that are not reported in the public databases or literature; they include a truncating mutation, such as a nonsense, conserved splice site, frameshift small indel, or large deletion) in known tumor suppressor genes.

Example 2

Methods

The following exemplifies certain embodiments of the methods and experimental conditions used to identify the mutation described in Table 1. Additional screening can be done using, e.g., qRT-PCR analysis of cDNA prepared from a pre-selected tumor sample.

Massively parallel DNA sequencing was done on hybridization captured, adaptor ligation-based libraries using DNA isolated from archived fixed paraffin-embedded tissue. A combination of analysis tools were used to analyze the data and assign DNA alteration calls.

Genomic DNA Sequencing

Sequencing of cancer genes was done using DNA from archived formalin fixed paraffin embedded (FFPE) tumor specimens from HNSCC patients. Sequencing libraries were constructed by the adapter ligation method using genomic DNA followed by hybridization selection with optimized RNA hybridization capture probes (Agilent SureSelect custom kit). Sequencing on the HiSeq2000 instrument (Illumina) was done using 49×49 paired reads to an average depth of 514×. Data processing and mutation assignments for base substitutions, indels, copy number alterations and genomic rearrangements were done using a combination of tools optimized for mutation calling from tumor tissue.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by the COSMIC database, available on the worldwide web at sanger.ac.uk/genetics/CGP/cosmia; and the Institute for Genomic Research (TIGR) on the world wide web at tigr.org and/or the National Center for Biotechnology Information (NCBI) on the world wide web at ncbi.nlm.nih.gov.

EQUIVALENTS

Those skilled in the art will recognize, or be able to ascertain using no more than routine experimentation, many equivalents to the specific embodiments described herein. Such equivalents are intended to be encompassed by the following claims.

We claim:

1. A method of treating a subject having a squamous cell carcinoma of the head and neck (HNSCC), the method comprising:
   acquiring knowledge that the subject has a mutation in a cell-cycle gene; and
   administering to the subject a cyclin dependent kinase (CDK) inhibitor that inhibits one or both of cyclin dependent kinase 4 (CDK4) or cyclin dependent kinase 6(CDK6),
   thereby treating the HNSCC in the subject.

2. The method of claim 1, wherein the cell-cycle gene is chosen from a cyclin dependent kinase inhibitor 2A (CDKN2A) gene, a cyclin dependent kinase inhibitor 2B (CDKN2B) gene, a Cyclin E1(CCNE1) gene, a Cyclin D1(CCND1) gene, a Cyclin D2 (CCND2) gene, a Cyclin D3 (CCND3) gene, a CDK4 gene, a CDK6 gene, or a gene described in Table 1 or Table 4.

3. The method of claim 1, wherein the subject has one or more of:
   (i) a loss-of-function mutation in a CDKN2A gene;
   (ii) a gain-of-function mutation in a CCND1 gene;
   (iii) a mutation or a mutant polypeptide described in Table 1 or 4; or
   (iv) a mutant CDKN2A, CDKN2B, or CCND1 polypeptide.

4. The method of claim 1, wherein the mutation in the cell-cycle gene is detected in a nucleic acid molecule by one or more of: sequencing, a nucleic acid hybridization assay, an amplification-based assay, a PCR-RFLP assay, real-time PCR, screening analysis, FISH, spectral karyotyping, MFISH, comparative genomic hybridization, in situ hybridization, SSP, HPLC, or mass-spectrometric genotyping.

5. The method of claim 1, wherein the knowledge that the subject has a mutation in a cell-cycle gene is obtained from a sample isolated from the subject, wherein the sample is a blood sample, a serum sample, a urine sample, a tissue sample, or a buccal swab, or comprises a cell from a tumor biopsy or a circulating tumor cell.

6. The method of claim 5, wherein the sample is positive for CCND1 by immunohistochemistry.

7. The method of claim 1, wherein the CDK inhibitor inhibits both CDK4 and CDK6.

8. The method of claim 1, wherein the CDK inhibitor is chosen from LEE011, LY-2835219, or PD 0332991.

9. The method of claim 8, wherein the CDK inhibitor is LEE011.

10. The method of claim 8, wherein the CDK inhibitor is LY-2835219.

11. The method of claim 8, wherein the CDK inhibitor is PD 0332991.

12. The method of claim 1, further comprising administering a radiation therapy to the subject, performing a surgery on the subject, or both.

13. The method of claim 1, wherein the HNSCC is localized.

14. The method of claim 1, wherein the subject has metastatic cancer.

15. A method of treating a subject having an HNSCC, the method comprising:
   selecting a subject having a mutation in a cell-cycle gene; and
   administering to the selected subject a CDK inhibitor chosen from LEE011, LY-2835219, PD 0332991, Indisulam, AZD5438, SNS-032, SCH 727965, JNJ-7706621, indirubin, or Seliciclib,
   thereby treating the HNSCC in the subject.

16. The method of claim 15 further comprising acquiring knowledge of whether the subject has a mutation in a cell-cycle gene.

17. The method of claim 15, wherein the cell-cycle gene is chosen from a cyclin dependent kinase inhibitor 2A (CDKN2A) gene, a cyclin dependent kinase inhibitor 2B (CDKN2B) gene, a Cyclin E1 (CCNE1) gene, a Cyclin D1 (CCND1) gene, a Cyclin D2 (CCND2) gene, a Cyclin D3 (CCND3) gene, a cyclin dependent kinase 4 (CDK4) gene, a cyclin dependent kinase 6 (CDK6) gene, or a gene described in Table 1 or Table 4.

18. The method of claim 15, wherein said mutation is chosen from:
   (i) a loss-of-function mutation in a CDKN2A gene;
   (ii) a gain-of-function mutation in a CCND1 gene;
   (iii) a mutation or a mutant polypeptide described in Table 1 or 4; or
   (iv) a mutant CDKN2A, CDKN2B or CCND1 polypeptide.

19. The method of claim 15, wherein the CDK inhibitor is chosen from LEE011, LY-2835219, or PD 0332991.

20. A method for generating a personalized cancer treatment report, the method comprising:
   acquiring a sample from a subject having an HNSCC;
   determining whether the subject has a mutation in a cell-cycle gene;
   selecting a CDK inhibitor that inhibits one or both of CDK4 or CDK6 as a treatment, if the subject has a mutation in a cell-cycle gene; and
   generating a personalized cancer treatment report to memorialize the presence or absence of a mutation in a cell cycle gene in the subject.

21. The method of claim 20, wherein the cancer treatment report comprises one or more of the following:
   (i) information on prognosis, resistance, or potential therapeutic options;
   (ii) information on the likely effectiveness of a therapeutic option;
   (iii) the acceptability of a therapeutic option, or the advisability of applying the therapeutic option to the subject; or
   (iv) information on the administration of a drug.

22. The method of claim 20, wherein the CDK inhibitor is chosen from LEE011, LY-2835219, or PD 0332991.

* * * * *

SEQUENCE LISTING

```
<160> NUMBER OF SEQ ID NOS: 1

<210> SEQ ID NO 1
<211> LENGTH: 200
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (16)..(185)
<223> OTHER INFORMATION: n = a, c, t, g, unknown or other

<400> SEQUENCE: 1
atcgcaccag cgtgtnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnncactg cggctcctca                                                  200
```